(12) United States Patent
Cavanagh et al.

(10) Patent No.: US 10,174,071 B2
(45) Date of Patent: Jan. 8, 2019

(54) PREPARATIONS OF HYDROPHOBIC THERAPEUTIC AGENTS, METHODS OF MANUFACTURE AND USE THEREOF

(71) Applicant: NICOX OPHTHALMICS, INC., Fort Worth, TX (US)

(72) Inventors: Thomas Cavanagh, New Canaan, CT (US); Shikha P. Barman, Bedford, MA (US); Tian Hao, Acton, MA (US); Thomas B. Leland, Bolton, MA (US); Ritesh V. Thekkedath, Dombivli (IN)

(73) Assignee: NICOX OPHTHALMICS, INC., Fort Worth, TX (US)

( * ) Notice: Subject to any disclaimer, the term of this patent is extended or adjusted under 35 U.S.C. 154(b) by 0 days.

(21) Appl. No.: 15/660,470

(22) Filed: Jul. 26, 2017

(65) Prior Publication Data

US 2018/0022775 A1 Jan. 25, 2018

Related U.S. Application Data

(63) Continuation of application No. 14/399,780, filed as application No. PCT/US2013/039694 on May 6, 2013, now Pat. No. 9,822,142, which is a continuation of application No. 13/735,973, filed on Jan. 7, 2013, now Pat. No. 8,765,725.

(60) Provisional application No. 61/644,105, filed on May 8, 2012, provisional application No. 61/657,239, filed on Jun. 8, 2012, provisional application No. 61/692,487, filed on Aug. 23, 2012, provisional application No. 61/763,770, filed on Feb. 12, 2013, provisional application No. 61/788,519, filed on Mar. 15, 2013.

(51) Int. Cl.
| | |
|---|---|
| *A61K 31/56* | (2006.01) |
| *C07J 3/00* | (2006.01) |
| *C07J 7/00* | (2006.01) |
| *C07J 31/00* | (2006.01) |
| *C07J 71/00* | (2006.01) |

(52) U.S. Cl.
CPC .............. *C07J 7/009* (2013.01); *C07J 3/005* (2013.01); *C07J 31/006* (2013.01); *C07J 71/0005* (2013.01); *C07J 71/0031* (2013.01); *C07B 2200/13* (2013.01); *Y10T 428/2982* (2015.01)

(58) Field of Classification Search
CPC ...... C07J 3/005; C07J 31/006; C07J 71/0031; C07B 2200/13
USPC .......................................... 514/180; 552/610
See application file for complete search history.

(56) References Cited

U.S. PATENT DOCUMENTS

| | | |
|---|---|---|
| 4,407,791 A | 10/1983 | Stark |
| 5,510,118 A | 4/1996 | Bosch et al. |
| 5,560,932 A | 10/1996 | Bagchi et al. |
| 5,662,883 A | 9/1997 | Bagchi et al. |
| 5,665,331 A | 9/1997 | Bagchi et al. |
| 5,993,781 A | 11/1999 | Snell et al. |
| 6,267,989 B1 | 7/2001 | Liversidge et al. |
| 6,406,718 B1 | 6/2002 | Cooper |
| 6,479,035 B1 | 11/2002 | Cripps et al. |
| 6,482,438 B1 | 11/2002 | Singh et al. |
| 6,630,129 B2 | 10/2003 | Cripps et al. |
| 6,875,449 B1 | 4/2005 | Marriott et al. |
| 7,060,712 B2 | 6/2006 | Axt et al. |
| 7,220,403 B2 | 5/2007 | Cripps et al. |
| 7,384,478 B2 | 6/2008 | Singh |
| 7,387,794 B2 | 6/2008 | Yang |
| 7,462,366 B2 | 12/2008 | Lanphere et al. |
| 7,592,329 B2 | 9/2009 | Biggadike et al. |
| 7,737,414 B2 | 6/2010 | Kuo et al. |
| 7,972,626 B2 | 7/2011 | Chaudry |
| 8,003,127 B2 | 8/2011 | Liversidge et al. |
| 8,062,657 B2 | 11/2011 | Edelman et al. |
| 8,148,353 B2 | 4/2012 | Macdonald et al. |
| 2002/0022629 A1 | 2/2002 | Cagle et al. |
| 2003/0032632 A1 | 2/2003 | Crispps et al. |
| 2003/0086876 A1 | 5/2003 | Cripps et al. |
| 2003/0181432 A1 | 9/2003 | Lancaster et al. |
| 2004/0037783 A1 | 2/2004 | Cripps et al. |
| 2004/0045805 A1 | 3/2004 | Lancaster et al. |
| 2004/0141925 A1 | 7/2004 | Bosch et al. |
| 2004/0157815 A1 | 8/2004 | Cripps et al. |
| 2004/0208833 A1 | 10/2004 | Hovey et al. |
| 2004/0224982 A1 | 11/2004 | Axt et al. |
| 2004/0258756 A1 | 12/2004 | McLoughlin |
| 2005/0043284 A1 | 2/2005 | Biggadike et al. |
| 2005/0075271 A1 | 4/2005 | Linsell et al. |
| 2005/0090675 A1 | 4/2005 | Vetturini et al. |

(Continued)

FOREIGN PATENT DOCUMENTS

| | | |
|---|---|---|
| EP | 0 995 435 A1 | 4/2000 |
| EP | 0760649 | 10/2001 |

(Continued)

OTHER PUBLICATIONS

"Advair Diskus.RTM . . . " Physicians' Desk Reference. New Jersey: Thomson PDR, 57th ed. pp. 1433-1439 (2003).
Balbach, S. et al., "Pharmaceutical evaluation of early development candidates: The 100 mg-approach'", International Journal of Phamaceutics, 275:1-12 (2004).

(Continued)

*Primary Examiner* — Barbara P Badio
(74) *Attorney, Agent, or Firm* — Arent Fox LLP

(57) ABSTRACT

The present invention further provides method of preparing nanocrystals of a hydrophobic therapeutic agent such as fluticasone or triamcinolone, pharmaceutical compositions (e.g., topical or intranasal compositions) thereof and methods for treating and/or preventing the signs and/or symptoms of disorders such as blepharitis, meibomian gland dysfunction or skin inflammation or a respiratory disease (e.g., asthma).

20 Claims, 39 Drawing Sheets

(56) References Cited

U.S. PATENT DOCUMENTS

| | | |
|---|---|---|
| 2005/0123608 A1 | 6/2005 | Yang |
| 2005/0222107 A1 | 10/2005 | Coote et al. |
| 2005/0222108 A1 | 10/2005 | Bhatarah et al. |
| 2005/0232998 A1 | 10/2005 | Bulsara et al. |
| 2006/0009435 A1 | 1/2006 | Kaspi et al. |
| 2006/0019937 A1 | 1/2006 | Adin et al. |
| 2006/0045850 A1 | 3/2006 | Namburi et al. |
| 2006/0096522 A1 | 5/2006 | Singh |
| 2007/0020298 A1 | 1/2007 | Pipkin et al. |
| 2007/0020330 A1 | 1/2007 | Dang et al. |
| 2007/0020684 A1 | 1/2007 | Bledsoe et al. |
| 2007/0065372 A1 | 3/2007 | Price et al. |
| 2007/0065374 A1 | 3/2007 | Liversidge et al. |
| 2007/0088014 A1 | 4/2007 | Edelman et al. |
| 2007/0178166 A1 | 8/2007 | Bernstein et al. |
| 2008/0312194 A1 | 12/2008 | Ousler, III et al. |
| 2009/0082321 A1 | 3/2009 | Edelman et al. |
| 2009/0177001 A1 | 7/2009 | Gore et al. |
| 2009/0233891 A1 | 9/2009 | Sen et al. |
| 2009/0312724 A1 | 12/2009 | Pipkin et al. |
| 2010/0018853 A1 | 1/2010 | Robinson et al. |
| 2010/0119609 A1 | 5/2010 | Dobak |
| 2010/0130458 A1 | 5/2010 | MacDonald et al. |
| 2010/0190760 A1 | 7/2010 | Ruecroft et al. |
| 2010/0197646 A1 | 8/2010 | Bhatarah et al. |
| 2010/0227842 A1 | 9/2010 | Bowman et al. |
| 2010/0240625 A1 | 9/2010 | Abelson et al. |
| 2010/0240629 A1 | 9/2010 | Kovacsne-Mezei et al. |
| 2011/0003803 A1 | 1/2011 | Stroman et al. |
| 2011/0077229 A1 | 3/2011 | Edelman et al. |
| 2011/0081411 A1 | 4/2011 | Perrett et al. |
| 2011/0105450 A1 | 5/2011 | Chapin et al. |
| 2011/0144071 A1 | 6/2011 | Grawe et al. |
| 2011/0224176 A1 | 9/2011 | Dobak et al. |
| 2011/0257136 A1 | 10/2011 | Abelson et al. |
| 2012/0065178 A1 | 3/2012 | Edelman et al. |
| 2012/0255544 A1 | 10/2012 | Padilla et al. |

FOREIGN PATENT DOCUMENTS

| | | |
|---|---|---|
| EP | 1067903 | 6/2002 |
| EP | 0937100 | 5/2003 |
| EP | 1225875 | 7/2004 |
| EP | 1294360 | 10/2005 |
| EP | 1469938 | 12/2005 |
| EP | 1438023 | 3/2006 |
| EP | 1294359 | 4/2006 |
| EP | 1143930 | 10/2006 |
| EP | 1476201 | 12/2008 |
| EP | 1474436 | 10/2009 |
| EP | 1622875 | 12/2009 |
| EP | 1472272 | 3/2010 |
| EP | 2044099 | 5/2012 |
| EP | 2077830 | 11/2012 |
| GB | 2088877 | 6/1982 |
| JP | H11-029463 A | 2/1999 |
| JP | 2010-535796 A | 11/2010 |
| JP | 2011-503073 A | 1/2011 |
| RU | 2003111926 A | 10/2004 |
| WO | WO 1995/031964 | 11/1995 |
| WO | WO 1998/017676 | 4/1998 |
| WO | WO 1999/048475 | 9/1999 |
| WO | WO 00/38811 A1 | 7/2000 |
| WO | WO 2000/038811 | 7/2000 |
| WO | WO 2001/019342 | 3/2001 |
| WO | WO 2001/032125 | 5/2001 |
| WO | WO 2002/000198 | 1/2002 |
| WO | WO 2002/000199 | 1/2002 |
| WO | WO 2003/035035 | 5/2003 |
| WO | WO 2003/061816 | 7/2003 |
| WO | WO 2003/066653 | 8/2003 |
| WO | WO 2003/066656 | 8/2003 |
| WO | WO 2003/070285 | 8/2003 |
| WO | WO 2003/088944 | 10/2003 |
| WO | WO 2003/099290 | 12/2003 |
| WO | WO 2004/011416 | 2/2004 |
| WO | WO 2004/069225 | 8/2004 |
| WO | WO 2004/101525 | 11/2004 |
| WO | WO 2005/065649 | 7/2005 |
| WO | WO 2005/074942 | 8/2005 |
| WO | WO 2006/011148 | 2/2006 |
| WO | WO 2006/026083 | 3/2006 |
| WO | WO 2006/099591 | 9/2006 |
| WO | WO 2007/047607 | 4/2007 |
| WO | WO 2007/070851 | 6/2007 |
| WO | WO 2007/144668 | 12/2007 |
| WO | WO 2008/005692 | 1/2008 |
| WO | WO 2008/048770 | 4/2008 |
| WO | WO 2008/155570 | 12/2008 |
| WO | WO 2009/023471 A2 | 2/2009 |
| WO | WO 2009/039262 | 3/2009 |
| WO | WO 2009/064457 A2 | 5/2009 |
| WO | WO 2010/007446 | 1/2010 |
| WO | WO 2010/016931 | 2/2010 |
| WO | WO 2010/052896 | 5/2010 |
| WO | WO 2010/107689 | 9/2010 |
| WO | WO 2010/108107 | 9/2010 |
| WO | WO 2010/141834 | 12/2010 |
| WO | WO 2011/041509 | 4/2011 |
| WO | WO 2011/069197 | 6/2011 |
| WO | WO 2011/088413 | 7/2011 |
| WO | WO 2011/093811 | 8/2011 |
| WO | WO 2011/093813 | 8/2011 |
| WO | WO 2011/093818 | 8/2011 |
| WO | WO 2011/093820 | 8/2011 |
| WO | WO 2011/096909 | 8/2011 |
| WO | WO 2011/105975 | 9/2011 |
| WO | WO 2011/116020 | 9/2011 |
| WO | WO 2011/136753 | 11/2011 |
| WO | WO 2011/145109 | 11/2011 |
| WO | WO 2012/029077 A2 | 3/2012 |
| WO | WO 2012/094283 | 7/2012 |
| WO | WO 2012/107765 | 8/2012 |
| WO | WO 2013/009591 A1 | 1/2013 |

OTHER PUBLICATIONS

Bikiaris, "Solid Dispersions, Part I: Recent Evolutions and Future Opportunities in Manufacturing Methods for Dissolution Rate Enhancement of Poorly Water-Soluble Drugs", Expert Opin. Drug Deliv., 8(11):1501-1519 (20110.

Čejka et al., "Crystal Structure of Fluticasone Propionate", Z. Kristallogr. NCS., 220:143-144 (2005).

Chen et al., "Nanonization Strategies for Poorly Water-Soluble Drugs", Drug Discov. Today, 16(7-8):354-360 (2011).

Dahan et al., "Provisional BCS Classification of the Leading Oral Drugs on the Global Market", Burger's Medicinal Chemistry, Drug Discovery and Development, Abraham et al., eds. New Jersey: John Wiley & Sons, Inc., pp. 353-366 (2010).

Elgart et al., "Lipospheres and Pro-Nano Liposheres for Delivery of Poorly Water Soluble Compounds", Chem. Phys. Lipids., 165(34):438-453 (2012).

Feeley et al., "Determination of Surface Properties and Flow Characteristics of Salbutamol Sulphate, Before and After Micronisation", Int. J. Pharm., 172(1-2):89-96 (1998).

He et al., "Microemulsions as Drug Delivery Systems to Improve the Solubility and the Bioavailability of Poorly Water-Soluble Drugs", Expert Opin. Drug Deliv., 7(4):445-460 (2010).

Kariuki et al., "Structure Determination of a Steroid Directly from Powder Diffraction Data." Chem. Commun., 17:1677-1678 (1999).

Kasim et al., "Molecular Properties of WHO Essential Drugs & Provisional Biopharmaceutical Classification", MoL Pharm. 1(1):85-96 (2004).

Kawabata et al., "Formulation Design for Poorly Water-Soluble Drugs Based on Biopharmaceutics Classification System: Basic Approaches and Practical Applications", Int. J. Pharm., 420(1):1-10 (2011).

Kleberg et al., "Characterising the Behaviour of Poorly Water Soluble Drugs in the Intestine: Application of Biorelevant Media for Solubility, Dissolution and Transport Studies", J. Pharm. Pharmacol, 62(11):1656-1668 (2010).

(56) References Cited

OTHER PUBLICATIONS

Kubavat et al., "Investigation into the Influence of Primary Crystallization Conditions on the Mechanical Properties and Secondary Processing Behaviour of Fluticasone Propionate for Carrier Based Dry Powder Inhaler Formulations", Pharm. Res., 29(4):994-1006 (2012).

Lindenberg et al., "Classification of Orally Administered Drugs on the World Health Organization Model List of Essential Medicines According to the Biopharmaceutics Classification System", Eur. J. Pharm. Biopharm., 58:265-278 (2004).

Linn et al., "Soluplus.RTM. as an Effective Absorption Enhancer of Poorly Soluble Drugs in vitro and in vivo", Eur. J. Pharm. Sci., 45(3):336-343 (2012).

Louey et al., "Aerosol Dispersion of Respirable Particles in Narrow Size Distributions Using Drug-Alone and Lactose-Blend Formulations", Pharm. Res. 21(7):1207-1213 (2004).

Matysova et al., "Determination of Methylparaben, Propylparaben, Triamcinolone Acetonide and its Degradation Product in a Topical Cream by RP-HPLC", Anal. Bioanal Chem., 376(4):440-443 (2003).

Morissette, S.L. et al., "High-throughput crystallization: polymorphs, salts, co-crystals and solvates of pharmaceutical solids", Adv. Drug. Deliv. Rev., 56:275-300 (2004).

Murnane et al., "Crystallization and Crystallinity of Fluticasone Propionate," Cryst. Growth Des., 8(8):2753-2764 (2008).

Parhi et al., "Preparation and Characterization of Solid Lipid Nanoparticles—A Review", Curr. Drug Discov. Technol., 9(1):2-16 (2012).

Rasenack et al., "Dissolution Rate Enhancement by in situ Micronization of Poorly Water-Soluble Drugs", Pharm. Res., 19(12):1894-1900 (2002).

Sacchetti et al. "Spray-Drying and Supercritical Fluid Particle Generation Techniques", Inhalation Aerosols, Hickey, ed. New York: Marcel Dekker, Inc., pp. 337-384 (1996).

Salústio et al. "Advanced Technologies for Oral Controlled Release: Cyclodextrins for Oral Controlled Release", AAPS PharmSciTech., 12(4):1276-1292 (2011).

Singh et al. "Oral Formulation Strategies to Improve Solubility of Poorly Water-Soluble Drugs", Expert. Opin. Drug. Deliv., 8(10):1361-1378 (2011).

Singhal, D. et al "Drug Polymorphism and Dosage Form Design: A practical perspective", Advanced Drug Delivery Reviews, 56:335-347 (2004).

Srinarong et al., "Improved Dissolution Behavior of Lipophilic Drugs by Solid Dispersions: The Production Process as Starting Point for Formulation Considerations", Expert Opin. Drug Deliv., 8(9):1121-1140 (2011).

Steckel et al, "Metered-Dose Inhaler Formulation of Fluticasone-17-Propionate Micronized with Supercritical Carbon Dioxide Using the Alternative Propellant HFA-227", Int. J. Pharmaceutics., 173(1-2):25-33 (1998).

Steckel et al., "In Vitro Characterization of Jet-Milled and in-situ-Micronized Fluticasone-17-Propionate", Int. J. Pharm., 258(1-2):65-75 (2003).

Steckel et al., "Micronizing of Steroids for Pulmonary Delivery by Supercritical Carbon Dioxide", Int.J. Pharm., 152:99-110 (1997).

Tran et al., "Controlled Release Systems Containing Solid Dispersions: Strategies and Mechanisms", Pharm. Res., 28(10):2353-2378 (2011).

Van Hoogevest et al., "Drug Delivery Strategies for Poorly Water-Soluble Drugs: The Industrial Perspective", Expert Opin. Drug Deilv.. 8(11):1481-1500 (2011).

Vehring, "Pharmaceutical Particle Engineering via Spray Drying", Pharm. Res., 25(5):999-1022 (2008).

Verma et al., "A Comparative Study of Top-Down and Bottom-Up Approaches for the Preparation of Micro/Nanosuspensions", Int. J. Pharmaceutics., 380(1-2):216-222 (2009).

Weers et al., "Design of Fine Particles for Pulmonary Drug Delivery", Expert Opin. Drug Deliv., 4(3):297-313 (2007).

El-Gendy et al., "Nanoparticle agglomerates of fluticasone propionate in combination with albuterol sulfate as dry powder aerosols," European Journal of Pharmaceutical Sciences, 2011, pp. 522-533, vol. 44, Elesevier.
Extended European Search Report issued in European Patent Application No. 13787795.7 dated Oct. 14, 2015.
Hirayama, "Organic Compound Crystal Production Handbook: Principle and Know-how," pp. 57-58, Maruzen Co., Ltd., Jul. 25, 2008, English translation needed.
Murnane et al., "Comparison of salmeterol xinafoate microparticle production by conventional and novel antisolvent crystallization," European Journal of Pharmaceutics and Biopharmaceutics, May 1, 2008, pp. 94-105, vol. 69, No. 1, Elsevier Science Pub.
Murnane, "Investigations into the Formulation of Metered Dose Inhalers of Salmeterol Xinafoate and Fluticasone Propionate Microcrystals," Pharmaceutical Research, Oct. 2008, pp. 2283-2291, vol. 25, No. 10, Springer Science + Business Media, LLC, 2008.
Shioji, "Manufacture Technology of Solid Tablet," p. 12, CMC Publishing Co., Ltd. 2003, English translation needed.

Physico-Chemical Characteristics of Fluticasone Propionate

Chemical Structure of Fluticasone Propionate

| Properties | |
|---|---|
| API λmax | 240 nm |
| M.W. | 500.57 Daltons |
| Log P | 3.72 |
| Pk$_a$ | 14.48 |
| Melting Point | 272-273 C (DSC/TGA) |
| Decomposition Point | Decomposes right after melting |
| Photolabile | No |
| Polymorphic forms | I and II |
| Molecular Formula | $C_{25}H_{31}F_3O_5S$ |

PREPARATIONS OF HYDROPHOBIC THERAPEUTIC AGENTS, METHODS OF MANUFACTURE AND USE THEREOF

RELATED APPLICATIONS

This application is a continuation of U.S. Non-provisional application Ser. No. 14/399,780, filed Nov. 7, 2014, which is a national stage application, filed under 35 U.S.C. § 371, of PCT/US2013/039694, filed on May 6, 2013, which claims priority to, and the benefit of, U.S. provisional application Nos. 61/644,105, filed May 8, 2012; 61/657,239, filed Jun. 8, 2012; 61/692,487, filed Aug. 23, 2012, 61/763,770, filed Feb. 12, 2013; and 61/788,519, filed Mar. 15, 2013, and U.S. Non-provisional application Ser. No. 13/735,973, filed Jan. 7, 2013, now U.S. Pat. No. 8,765,725, issued Jul. 1, 2014. The contents of each of these applications are hereby incorporated by reference in their entireties.

FIELD OF THE INVENTION

The present invention provides a method of manufacture of sterile nanocrystals of hydrophobic therapeutic agents (such as fluticasone propionate and triamcinolone acetonide) that are optimized to meet pharmaceutical standards of administration (e.g., topical or intranasal administration).

BACKGROUND OF THE INVENTION

Fluticasone Propionate [(6α,11β,16α,17α)-6,9,-difluoro-11-hydroxy-16-methyl-3-oxo-17-(1-oxopropoxy) androsta-1,4-diene-17-carbothioic acid, S-fluoromethyl ester], a synthetic fluorinated corticosteroid. The corticosteroids constitute a class of primarily synthetic steroids used as anti-inflammatory and antipruritic agents. Fluticasone Propionate (FP) has been commercialized as a corticosteroid to treat inflammation associated diseases such as allergic rhinitis, asthma and atopic dermatitis. The PK/PD properties of this molecule have been well-established by its long standing use in humans.

Chemically, fluticasone propionate is $C_{25}H_{31}F_3O_5S$. Fluticasone propionate has a molecular weight of 500.6. It is a white to off-white powder and is insoluble in water. Like other topical corticosteroids, fluticasone propionate has anti-inflammatory, antipruritic and vasoconstrictive properties. The mechanism of the anti-inflammatory activity of the topical steroids, in general, is unclear. However, corticosteroids are thought to act by the induction of phospholipase $A_2$ inhibitory proteins, collectively called lipocortins. It is postulated that these proteins control the biosynthesis of potent mediators of inflammation such as prostaglandins and leukotrienes by inhibiting the release of their common precursor, arachidonic acid. Arachidonic acid is released from membrane phospholipids by phospholipase $A_2$. The compound has potent anti-inflammatory activity and is particularly useful for the treatment of respiratory disorders, particularly asthma. In vitro assays using human lung cytosol preparations have established fluticasone propionate as a human glucocorticoid receptor agonist with an affinity 18 times greater than dexamethasone, and almost twice that of beclomethasone-17-monopropionate (BMP), the active metabolite of budesonide.

Adverse reactions from the current marketed forms of fluticasone propionate include lymphatic signs and symptoms; cardiovascular palpitations; hypersensitivity reactions, including angioedema, skin rash, edema of the face and tongue, pruritus, urticaria, bronchospasm, wheezing, dyspnea, and anaphylaxis/anaphylactoid reactions; otitis media; tonsillitis; rhinorrhea/postnasal drip/nasal discharge; earache; cough; laryngitis; hoarseness/dysphonia; epistaxis; tonsillitis; nasal signs and symptoms; unspecified oropharyngeal plaques; ear, nose, and throat polyps; sneezing; pain in nasal sinuses; rhinitis; throat constriction; allergic ear, nose, and throat disorders; alteration or loss of sense of taste and/or smell; nasal septal perforation; blood in nasal mucosa; nasal ulcer; voice changes; fluid disturbances; weight gain; goiter; disorders of uric acid metabolism; appetite disturbances; irritation of the eyes; blurred vision; glaucoma; increased intraocular pressure and cataracts; keratitis and conjunctivitis; blepharoconjunctivitis; nausea and vomiting; abdominal pain; viral gastroenteritis; gastroenteritis/colitis; gastrointestinal infections; abdominal discomfort; diarrhea; constipation; appendicitis; dyspepsia and stomach disorder; abnormal liver function; injury; fever; tooth decay; dental problems; mouth irritation; mouth and tongue disorders; cholecystitis; lower respiratory infections; pneumonia; arthralgia and articular rheumatism; muscle cramps and spasms; fractures; wounds and lacerations; contusions and hematomas; burns; musculoskeletal inflammation; bone and cartilage disorders; pain in joint; sprain/strain; disorder/symptoms of neck; muscular soreness/pain; aches and pains; pain in limb; dizziness/giddiness; tremors; hypnagogic effects; compressed nerve syndromes; sleep disorders; paralysis of cranial nerves; migraine; nervousness; bronchitis; chest congestion and/or symptoms; malaise and fatigue; pain; edema and swelling; bacterial infections; fungal infections; mobility disorders; cysts, lumps, and masses; mood disorders; acute nasopharyngitis; dyspnea; irritation due to inhalant; urticaria; rash/skin eruption; disorders of sweat and sebum; sweating; photodermatitis; dermatitis and dermatosis; viral skin infections; eczema; fungal skin infections; pruritus; acne and folliculitis; burning; hypertrichosis; increased erythema; hives; folliculitis; hypopigmentation; perioral dermatitis; skin atrophy; striae; miliaria; pustular psoriasis; urinary infections; bacterial reproductive infections; dysmenorrhea; candidiasis of vagina; pelvic inflammatory disease; vaginitis/vulvovaginitis; and irregular menstrual cycle.

The mechanism of action of Fluticasone of all commercial and investigative products is identical; penetration of the plasma membrane of the cell and subsequent binding of the molecule to the cytosolic glucocorticoid receptors, represented by two separate receptors GR-α and GR-β transcribed by a single gene. Of the two receptors, GR-α is implicated in the generation of anti-inflammatory responses. Other mechanisms of regulating inflammation are via protein—protein sequestration via binding to other pro-inflammatory transcription factors such as activator protein (AP-1), leading to the inhibition of the transcription of inflammatory genes. The GC-GR complex can also act indirectly via the induction of inhibitory proteins, for example IκB that suppresses NF-κB activity. Thus, anti-inflammatory effects also affect the immunological pathway, leading to immunosuppression, one of side effects observed with the drug. Other side effects that are relevant are ophthalmic effects such as increase of intraocular pressure (glaucoma) and the growth of cataracts. However, these side effects are correlated to the concentration of the drug and the route of administration.

A need exists for topical preparations of Fluticasone that are suitable for ophthalmic use.

SUMMARY OF THE INVENTION

The invention is based upon the discovery of a process to prepare sterile stable nanocrystals of hydrophobic drugs such as fluticasone propionate nanocrystals or triamcinolone acetonide nanocrystals. The process of the invention allows suspensions of the hydrophobic drug (e.g., fluticasone propionate and triamcinolone acetonide) nanocrystals to be concentrated form 0.0001% to 10% while maintaining size, purity, shape (rod or plate), pH, and osmolality. This process allows the production of topical formulation at higher tolerable concentrations then has been previously achieved for the treatment of ophthalmic and dermatologic inflammatory disorders. This process also allows production of more crystalline hydrophobic drugs and control of the sizes and size distributions of nanocrystals of the hydrophobic drugs. The control of size and size distribution may be achieved by selecting specific conditions of the process such as temperature, pH and/or viscosity of the component solutions for the process, type, molecular weight, and/or viscosity of the stabilizer, annealing duration, sonication output energy, batch size, and flow rates.

In one aspect, the invention provides a morphic form of fluticasone propionate (Form A) characterized by an X-ray powder diffraction pattern including peaks at about 7.8, 15.7, 20.8, 23.7, 24.5, and 32.5 degrees 2θ.

The invention also provides a plurality of nanoplates of fluticasone propionate having an average size of about 10-10000 nm, (e.g., 100-1000 nm or 300-600 nm).

The invention further provides a crystalline form of purified fluticasone propionate, characterized by a tap density of no less than 0.35 g/cm$^3$ (e.g., no less than 0.40 g/cm$^3$, no less than 0.45 g/cm$^3$, no less than 0.50 g/cm$^3$, or no less than 0.55 g/cm$^3$).

The morphic form, crystal form, and/or nanocrystals described herein may include one or more of the following features.

The morphic form is further characterized by an X-ray powder diffraction pattern further including peaks at about 9.9, 13.0, 14.6, 16.0, 16.9, 18.1, and 34.3 degrees 2θ.

The morphic form is characterized by an X-ray powder diffraction pattern substantially similar to that set forth in FIG. 31A.

The morphic form has a purity of greater than 80% by weight (e.g., >85%, >90%, >95%, >97%, >98%, or >99%).

The morphic form is further characterized by a tap density of no less than 0.35 g/cm$^3$, (e.g., no less than 0.40 g/cm$^3$, no less than 0.45 g/cm$^3$, no less than 0.50 g/cm$^3$, or no less than 0.55 g/cm$^3$).

The morphic form is further characterized by a melting point of 299.5° C. with a melting range of 10° C.

The morphic form is further characterized by a dissolution rate in water of about 1 μg/g/day in water at room temperature.

The morphic form comprises fluticasone propionate nanoplates with an average size of about 10-10000 nm, (e.g., 100-1000 nm, 300-600 nm, 400-800 nm, or 500-700 nm).

The morphic form comprises fluticasone propionate nanoplates with a narrow range of size distribution. In other words, the nanoplates are substantially uniform in size.

The morphic form comprises fluticasone propionate nanoplates with a size distribution of 50-100 nm, of 100-300 nm, of 300-600 nm, of 400-600 nm, of 400-800 nm, of 800-2000 nm, of 1000-2000 nm, of 1000-5000 nm, of 2000-5000 nm, of 2000-3000 nm, of 3000-5000 nm, or of 5000-10000 nm.

The nanoplates each have a thickness between 5 nm and 500 nm (e.g., 5-400 nm, 5-200 nm, 10-150 nm or 30-100 nm).

The nanoplates have the [001] crystallographic axis substantially normal to the surfaces that define the thickness of the nanoplates.

The plurality of nanoplates is characterized by a tap density of no less than 0.35 g/cm$^3$ (e.g., no less than 0.40 g/cm$^3$, no less than 0.45 g/cm$^3$, no less than 0.50 g/cm$^3$, or no less than 0.55 g/cm$^3$).

The plurality of nanoplates is characterized by a melting point of 299.5° C. with a melting range of 10° C.

The plurality of nanoplates is characterized by a dissolution rate in water of about 1 μg/g/day in water at room temperature.

The plurality of nanoplates is characterized by an X-ray powder diffraction pattern including peaks at about 7.8, 15.7, 20.8, 23.7, 24.5, and 32.5 degrees 2θ.

The plurality of nanoplates is further characterized by an X-ray powder diffraction pattern further including peaks at about 9.9, 13.0, 14.6, 16.0, 16.9, 18.1, and 34.3 degrees 2θ.

The plurality of nanoplates is characterized by an X-ray powder diffraction pattern substantially similar to that set forth in FIG. 31A.

The plurality of nanoplates has a purity of greater than 80% by weight (e.g., >85%, >90%, >95%, >97%, >98%, or >99%).

The crystalline form is further characterized by a melting point of 299.5° C. with a melting range of 10° C.

The crystalline form is further characterized by a dissolution rate in water of about 1 μg/g/day in water at room temperature.

The crystalline form is further characterized by an X-ray powder diffraction pattern including peaks at about 7.8, 15.7, 20.8, 23.7, 24.5, and 32.5 degrees 2θ.

The crystalline form is further characterized by an X-ray powder diffraction pattern further including peaks at about 9.9, 13.0, 14.6, 16.0, 16.9, 18.1, and 34.3 degrees 2θ.

The crystalline form is characterized by an X-ray powder diffraction pattern substantially similar to that set forth in FIG. 31A.

The crystalline form has a purity of greater than 80% by weight (e.g., >85%, >90%, >95%, >97%, >98%, or >99%).

In another aspect, this invention provides a novel morphic form of triamcinolone acetonide, i.e., Form B, which is characterized by an X-ray powder diffraction pattern including peaks at about 11.9, 13.5, 14.6, 15.0, 16.0, 17.7, and 24.8 degrees 2θ.

Form B is further characterized by an X-ray powder diffraction pattern including additional peaks at about 7.5, 12.4, 13.8, 17.2, 18.1, 19.9, 27.0 and 30.3 degrees 2θ.

Form B is characterized by an X-ray powder diffraction pattern substantially similar to the profile in red in FIG. 39.

Form B is substantially free of impurities.

Form B has a purity of greater than 85%, greater than 90%, greater than 92%, greater than 95%, greater than 96%, greater than 97%, greater than 98%, or greater than 99%.

The invention also provides a method of manufacturing the plurality of nanoplates described above. The method comprises:

providing a phase I solution (e.g., a sterile solution) comprising fluticasone propionate and a solvent for fluticasone propionate;

providing a phase II solution (e.g., a sterile solution) comprising at least one surface stabilizer and an antisolvent for fluticasone propionate, wherein the at least one surface stabilizer comprises a cellulosic surface stabilizer;

mixing the phase I solution and the phase II solution to obtain a phase III mixture, wherein sonication is applied when mixing the two solutions and the mixing is performed at a first temperature not greater than 25° C.; and annealing the phase III mixture at a second temperature that is greater than the first temperature for a period of time ($T_1$) such as to produce a phase III suspension comprising a plurality of nanoplates of fluticasone propionate.

In another aspect, the invention provides a method of manufacturing purified, stable, sterile nanocrystals of a hydrophobic therapeutic agent. The method includes:

providing a phase I solution (e.g., a sterile solution) comprising a hydrophobic therapeutic agent and a solvent for the hydrophobic therapeutic agent;

providing a phase II solution (e.g., a sterile solution) comprising at least one surface stabilizer and an antisolvent for the hydrophobic therapeutic agent;

mixing the phase I solution and the phase II solution to obtain a phase III mixture, wherein the mixing is performed at a first temperature not greater than 25° C.; and annealing the phase III mixture at a second temperature that is greater than the first temperature for a period of time ($T_1$) such as to produce a phase III suspension comprising a plurality of nanocrystals of the hydrophobic therapeutic agent.

The methods described herein may include one or more of the following features.

The hydrophobic therapeutic agent is a steroidal drug such as corticosteroid.

The hydrophobic therapeutic agent is fluticasone or an ester thereof or triamcinolone acetonide.

The hydrophobic therapeutic agent is fluticasone propionate.

Sonication (e.g., with power of 10-75 W or about 50-70 W) is applied when mixing the sterile phase I solution and the sterile phase II solution.

The first temperature is a temperature between −10° C. and 30° C., between −10° C. and 25° C. (e.g., 22° C. or not greater than 20° C.), or between −5° C. and 10° C., or between 0° C. and 5° C., or between 0° C. and 2° C., or between 2° C. and 4° C., or between 2° C. and 8° C.

The second temperature is a temperature between 4° C. and 60° C., or between 10° C. and 40° C., or between 15° C. and 25° C.

$T_1$ is at least 8 hours.

At least one surface stabilizer in the phase II solution comprises a cellulosic surface stabilizer.

The cellulosic surface stabilizer is methylcellulose with a molecular weight of not greater than 100 kDa.

The methyl cellulose is at a concentration of about 0.1% to 0.5% in the phase III suspension.

The cellulosic surface stabilizer used for the phase II solution is an aqueous solution.

The aqueous solution of the cellulosic surface stabilizer has a viscosity of not greater than 4000 cP (e.g., not greater than 2000 cP, not greater than 1000 cP, not greater than 500 cP, not greater than 100 cP, not greater than 50 cP, not greater than 30 cP, or not greater than 15 cP).

The aqueous solution of the cellulosic surface stabilizer has a viscosity of about 4 cP to 50 cP and the cellulosic surface stabilizer is methylcellulose.

The antisolvent comprises water (e.g., distilled water).

The at least one surface stabilizer in the phase II solution further comprises benzalkonium chloride.

The benzalkonium chloride concentration in phase II solution is about 0.005% to 0.15% (e.g., about 0.01%-0.12% or 0.02%-0.08%).

The pH value of phase II solution is not greater than 6.5, or not greater than 6.0, or not greater than 5.5.

The solvent of phase I solution comprises a polyether.

The polyether is selected from polyethylene glycol (PEG), polypropylene glycol (PPG), and a mixture thereof.

The polyether is selected from PEG400, PPG400, and a mixture thereof.

The PEG 400 is at a concentration of about 20 to 35% in the phase I solution.

The PPG 400 is at a concentration of about 65% to 75% in the phase I solution.

The solvent of phase I solution comprises one or more polyols such as monomeric polyols (e.g., glycerol, propylene glycol, and ethylene glycol) and polymeric polyols (e.g., polyethylene glycol).

The phase I solution further comprises a surface stabilizer.

The surface stabilizer in the phase I solution is TWEEN 80® (polysorbate 80), e.g., at a concentration of about 7.0% to 15% in the phase I solution.

The volume ratio of the phase I solution to phase II solution ranges from 1:10 to 10:1 (e.g., 1:3 to 3:1, or 1:2 to 2:1, or about 1:1).

The cellulosic surface stabilizer is methylcellulose with a molecular weight of not greater than 100 kDa, the first temperature is a temperature between 0° C. and 5° C., the second temperature is a temperature between 10° C. and 40° C., and $T_1$ is at least 8 hours.

The method further comprises purification of the plurality of nanocrystals of the hydrophobic therapeutic agent by tangential flow filtration or by continuous flow centrifugation. The method may further comprise drying the plurality of nanocrystals of the hydrophobic therapeutic agent by, e.g., filtration, vacuum drying, or centrifugation. The method may further comparing, after purifying the nanocrystals by, e.g., centrifugation, mixing the purified nanocrystals with a suitable aqueous solution to which additional excipients can be added to form a final formulation that meets FDA criteria for ophthalmic or dermatologic administration. For example, the mixing is performed in a mixer (e.g., a SILVERSON® Lab Mixer) at room temperature at 6000 RPM for about 60 mins or longer.

Purified, stable, sterile nanocrystals of fluticasone by mixing a sterile phase I solution of fluticasone with a sterile phase II solution comprising benzalkonium chloride, methyl cellulose, and distilled water such as to produce a phase III suspension containing a suspension of fluticasone nanocrystals. The nanocrystals are between 400-800 nm. To purify, i.e., to remove and or reduce the concentration of crystallization solvents of the phase I and phase II solution, the fluticasone nanocrystals are washed and exchanged into a suitable aqueous solution. The exchanging is performed for example by using tangential flow filtration (TFF) or hollow fiber filter cartridge. In some aspects the nanocrystals are exchange into a formulation that meets FDA criteria for ophthalmic or dermatologic administration. Alternatively the nanocrystals are exchanged into a sterile aqueous solution to which additional excipients are added to form a final formulation that meets FDA criteria for ophthalmic or dermatologic administration. The concentration of fluticasone in the final aqueous buffer solution is about between 0.0001% to 10% (w/v). In some aspects an annealing step is performed before the buffer exchanging step. The annealing step is performed at about 25-40° C. and is for a duration of between about 30 minutes to 24 hours.

Preferably, the fluticasone of the phase I solution is at a concentration of about 0.4% to 1.0% w/v. More preferably, the fluticasone of the phase I solution is at a concentration of about 0.45% w/v.

In some aspects the phase I solution further contains TWEEN 80® (polysorbate 80), polyethylene glycol (PEG) 400 and polypropylene glycol (PPG) 400. The TWEEN 80® (polysorbate 80) is at a concentration of about 7.0% to 15% w/v. The PEG 400 is at a concentration of about 20 to 35% (w/v). The PPG 400 is at a concentration of about 65% to 75% (w/v). In a preferred embodiment, the phase I solution contains fluticasone at a concentration of about 0.45% w/v, TWEEN 80® (polysorbate 80) at a concentration of about 7.44%, PEG 400 at a concentration of about 23% (w/v) and PPG 400 at a concentration of about 69.11% (w/v).

The mixing of phase I and phase II is performed at a temperature not greater than 8° C. (e.g., 0-2° C., 2-4° C., or 2-8° C.). The volume ratio of phase I to phase II is 0.15 to 0.3 or 1:1 to 1:3. The phase I solution is mixed with the phase II solution at a flow rate of 0.5 to 1.4 ml/min, wherein the phase II solution is stationary. See, e.g., FIG. 3. In other embodiments the phase III is formed in a flow reactor by combining the phase I solution at a flow rate of 0.5-900 ml/min (e.g., 0.5-2.0 ml/min, 10-900 ml/min, 12-700 ml/min, 50-400 ml/min, 100-250 ml/min, or 110-130 ml/min) and the phase II solution at a flow rate of 2.5-2100 ml/min (e.g., 2.5-10 ml/min, 10-900 ml/min, 12-700 ml/min, 50-400 ml/min, 100-250 ml/min, or 110-130 ml/min). See, e.g., FIG. 4. In some embodiments, the flow rate of phase I and that of phase II solutions are substantially the same. In other embodiments, the flow rate of phase I is less than that of phase II, e.g., volume ratio of the phase I solution to phase II solution is about 1:2 or 1:3. In some embodiments, the flow rate of the phase III suspension coming out of a flow reactor is at about 20-2800 ml/min (e.g., about 100-800 ml/min or 200-400 ml/min). Optionally, the phase III mixture is sonicated.

In some embodiments the final aqueous buffer comprising methyl cellulose, a permeation enhancer and a wetting agent. The methyl cellulose is for example at a concentration of about 0.5% (w/v).

Also included in the invention is a plurality of the nanocrystals produced by the methods of the invention and compositions (e.g., a pharmaceutical composition) containing the nanocrystals. The composition is substantially free of organic solvents. The nanocrystals have an average size ranging between 400-800 nm (e.g., 300-600 nm, 400-600 nm, or 500-700 nm). The nanocrystals do not agglomerate and do not increase in size over a period of 24 hours. The nanocrystals are nanoplates, e.g., fluticasone propionate nanoplates having the [001] crystallographic axis substantially normal to the surfaces that define the thickness of the nanoplates. The nanoplates can have a thickness ranging from about 5 nm to 100 nm. Optionally, the nanocrystals are coated with methyl cellulose.

Further provided by the invention is a sterile topical nanocrystal fluticasone formulation containing a suspension of between 0.0001%-10% w/v fluticasone nanocrystals of the invention and a pharmaceutically acceptable aqueous excipient. In some aspects the formulation has a viscosity between 10-20 cP at 20° C. The osmolality of the formulation is about 280-350 mOsm/kg. The pH of the formulation is about 6-7.5.

In another aspect the invention provides a method of treating or alleviating a symptom of an ocular disorder (e.g., blepharitis, meibomian gland dysfunction, post operative pain or post-operative ocular inflammation, dry eye, eye allergy, or uveitis) by administering, e.g., topically to the lid margin, skin, or ocular surface of, a subject in need thereof an effective amount of the formulations (e.g., topical formulations) of the invention. The formulation is administered for example by using an applicator (e.g., a brush or swab). In one embodiment, a therapeutically effective amount of the formulation is administered to a subject in need thereof for treating blepharitis, via e.g., an applicator (e.g., a brush such as LATISSE® (bimatoprost ophthalmic solution) brush or a swab such as 25-3317-U swab). In some embodiments, the formulation is a sterile topical nanocrystal fluticasone propionate formulation containing a suspension of between 0.001%-5% FP nanocrystals of the invention (e.g., 0.01-1%, or about 0.25%, 0.1%, or 0.05%), and a pharmaceutically acceptable aqueous excipient. In some embodiments, the formulation further contains about 0.002-0.01% (e.g. 50 ppm±15%) benzalkonium chloride (BKC). In some embodiments, the formulation further contains one or more coating dispersants (e.g., TYLOXAPOL® (formaldehyde, polymer with oxirane and 4-(1,1,3,3-tetrametylbutyl)phenorl), polysorbate 80, and PEG stearate such as PEG40 stearate), one or more tissue wetting agents (e.g., glycerin), one or more polymeric stabilizers (e.g., methyl cellulose 4000 cP), one or more buffering agents (e.g., dibasic sodium phosphate $Na_2HPO_4$ and monobasic sodium phosphate $NaH_2PO_4$, and/or one or more tonicity adjusting agents (e.g., sodium chloride). In some embodiments, the formulation has a viscosity between 40-50 cP at 20° C. In some embodiments, the osmolality of the formulation is about 280-350 (e.g., about 285-305) mOsm/kg. In some embodiments, the pH of the formulation is about 6.8-7.2. In some embodiments, the formulation has a viscosity between 40-50 cP at 20° C. In some embodiments, the FP nanocrystals in the formulation have a median size of 300-600 nm, a mean size of 500-700 nm, a D50 value of 300-600 nm, and/or a D90 value of less than 2 μm (e.g., less than 1.5 μm).

In yet another aspect the invention provides a method of treating or alleviating a respiratory disease (e.g., asthma or chronic obstructive pulmonary disease (COPD)), rhinitis, dermatitis, or esophagitis by administering to a subject in need thereof an effective amount of the pharmaceutical composition of the invention.

Also provided is a pharmaceutical composition comprising one or more pharmaceutically acceptable carriers or excipients and the nanocrystals of hydrophobic drugs (e.g., fluticasone propionate) produced by the methods of the invention. The composition can be in the form of dry powder/inhalers, ophthalmic preparations, sprays, ointments, creams, pills, etc.

In a further aspect the invention provides a semi-flexible polyurethane applicator comprising fluticasone nanocrystals of the invention and a pharmaceutically acceptable aqueous excipient.

In yet another aspect, the invention provides a surgical or implantable device (e.g., a stent, angioplasty balloon, catheter, shunt, access instrument, guide wire, graft system, intravascular imaging device, vascular closure device, endoscopy accessory, or other device disclosed herein) coated or impregnated with the fluticasone propionate crystals of the invention. In some embodiments, coating or embedding fluticasone propionate crystals into a surgical or implantable device modifies the release time of the drug. For example, coating or embedding fluticasone propionate crystals into a surgical or implantable device extends the release time of the drug.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Advantages of the methods of the invention include that the product (e.g., nanocrystals of the hydrophobic drug) is purer (or at least not less pure), is more crystalline, and/or is more stable than stock material of the drug. The advantages also include that the size and size distribution of the product are controllable and the product's size can be substantially uniform (which may lead to better control of drug release in vivo), and that the methods of the invention cause little or no degradation to the drug. Other features and advantages of the invention will be apparent from and encompassed by the following detailed description and claims.

BRIEF DESCRIPTIONS OF FIGURES

Figure 21B:
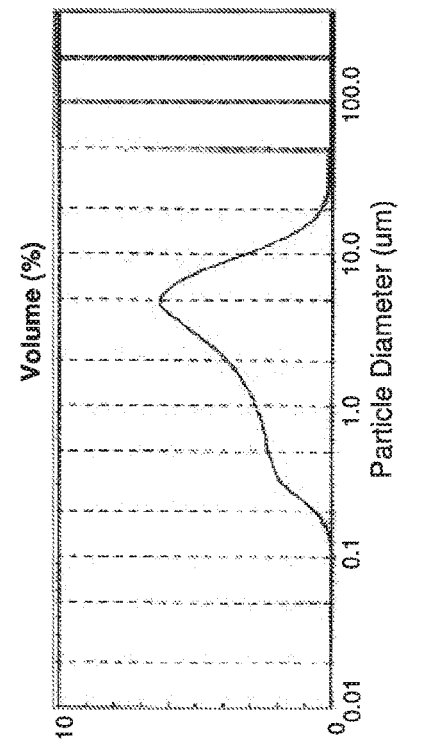
Figure 21A:
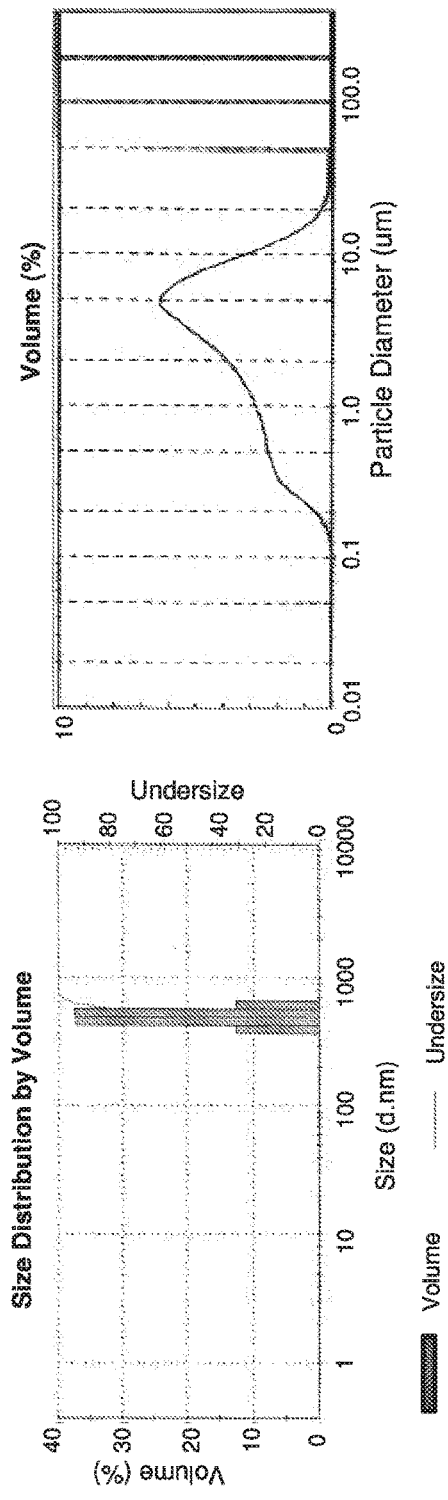
Figure 21C:
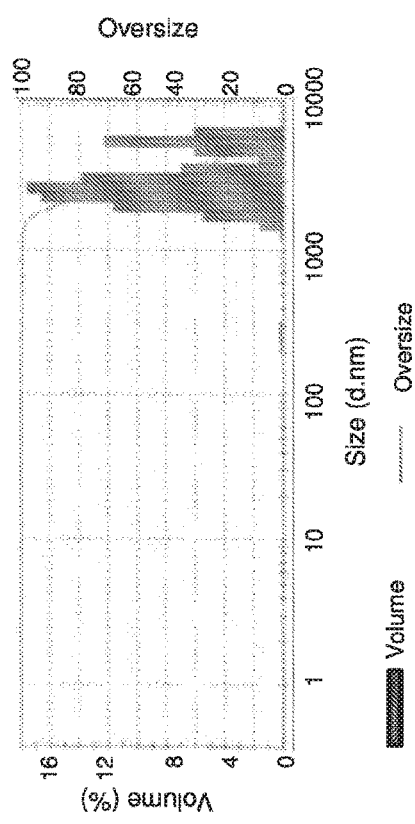
Figure 22B:
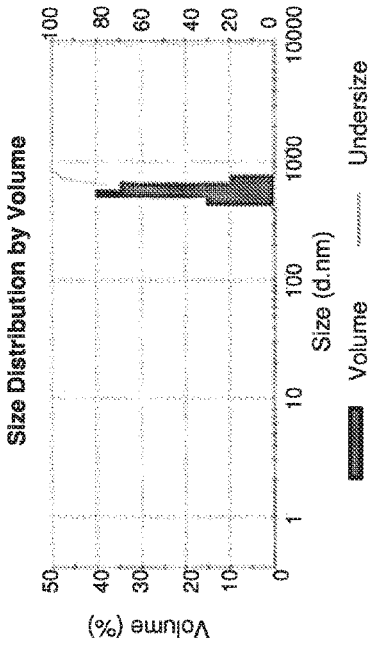
Figure 22D:
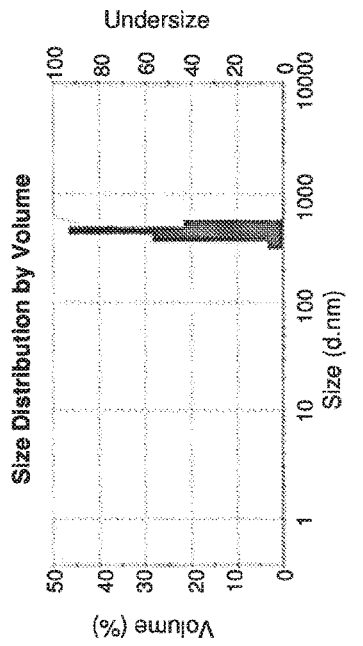
Figure 22A:
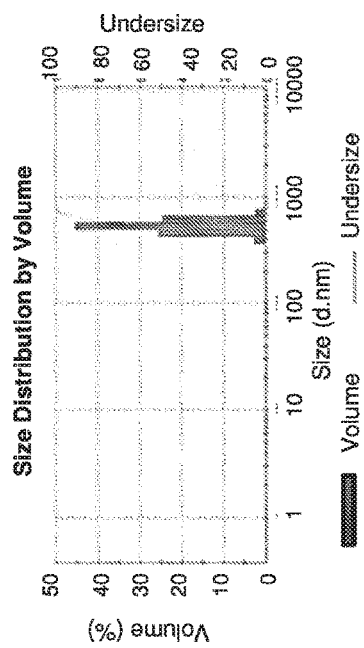
Figure 22C:
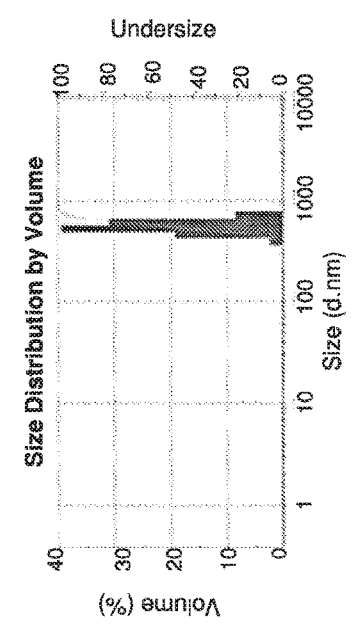

FIGS. 21A-C are plots showing particle size distributions of FP nanocrystals made by the batch process, FP particles made by homogenization, and FP stock received from manufacturer.

FIGS. 22A-D is a group of plots showing stability of particle size of the fluticasone propionate nanosuspension, at 25° C. and 40° C. for up to 75 days.

Figure 23:
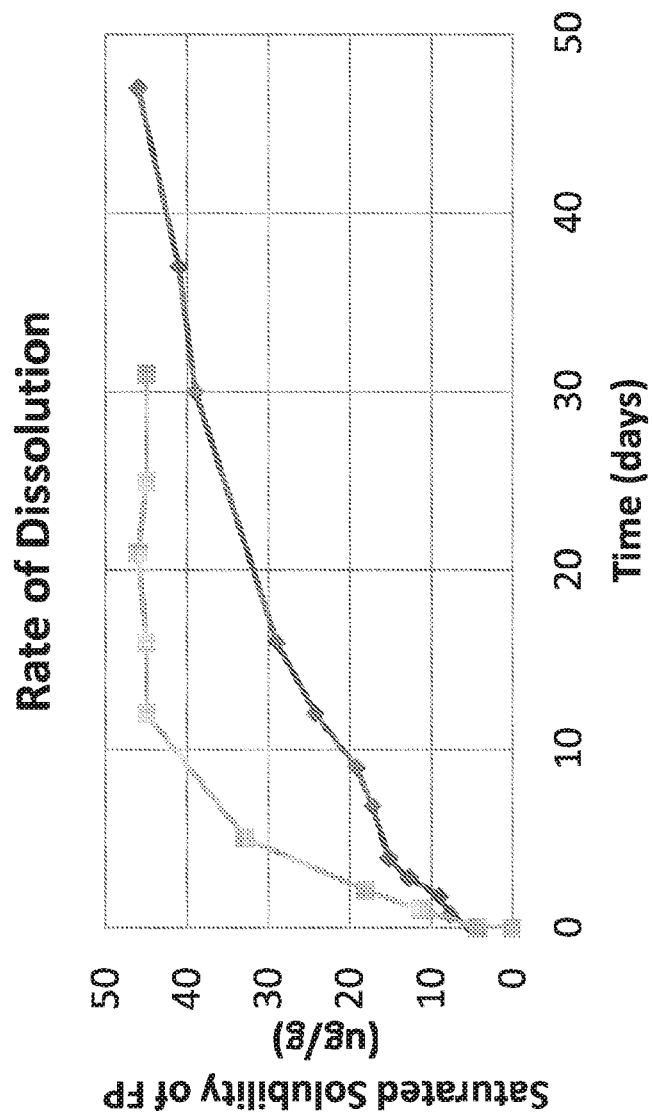

FIG. 23 is a plot showing dissolution rates of fluticasone propionate homogenized (1-5 microns, represented by grey square dots) and fluticasone propionate crystals produced by the batch process (400-600 nm, represented by black diamond dots).

Figure 24A:
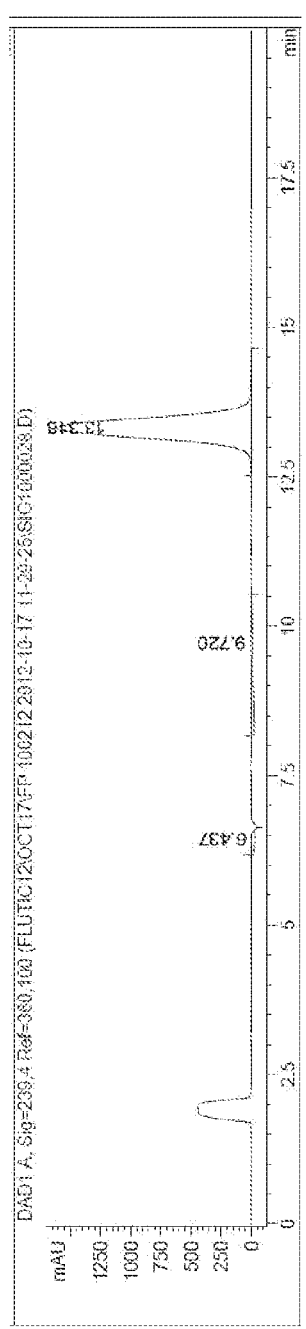
Figure 24B:
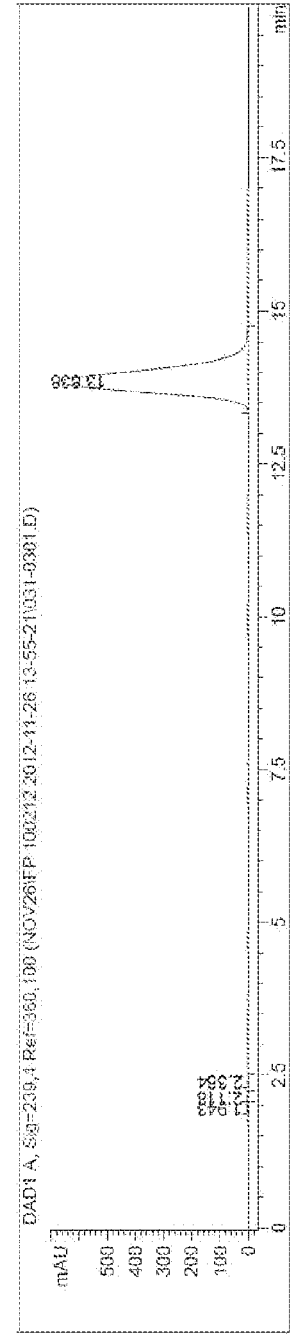

FIGS. 24A and 24B are chromatograms of fluticasone propionate stock material and nanocrystals produced by the batch process respectively.

Figure 25B:
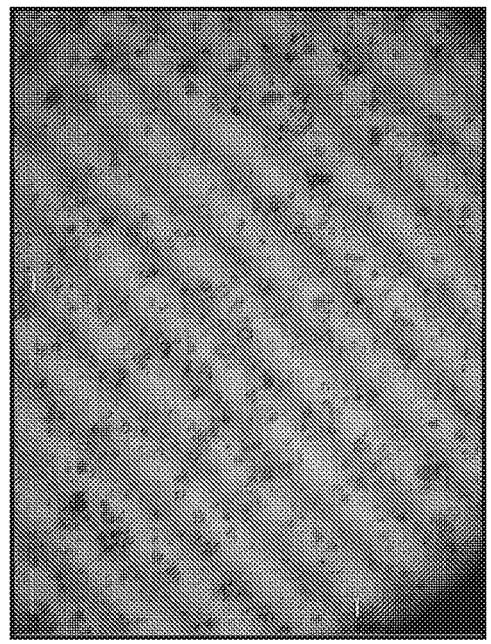
Figure 25A:
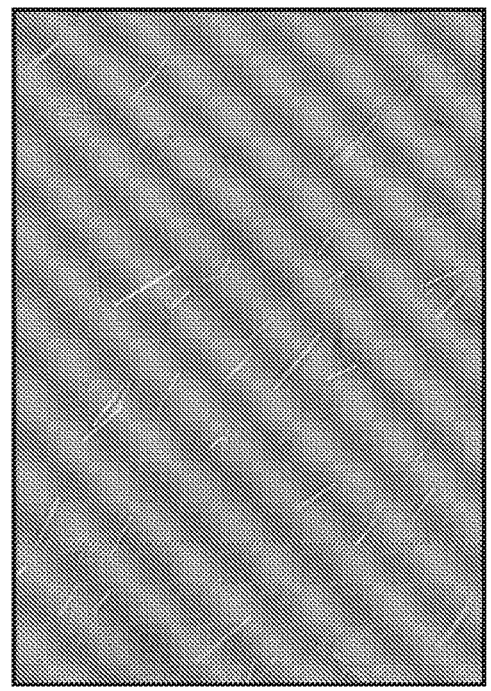

FIGS. 25A and 25B are optical micrographs (Model: OMAX, 1600×) of dried fluticasone propionate crystals prepared by the batch process and FP stock material, respectively.

Figure 26B:
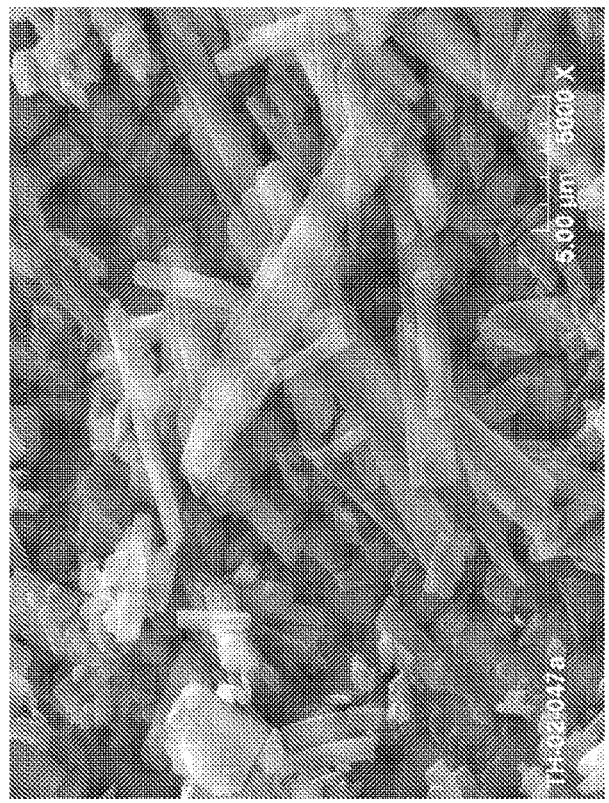
Figure 26A:
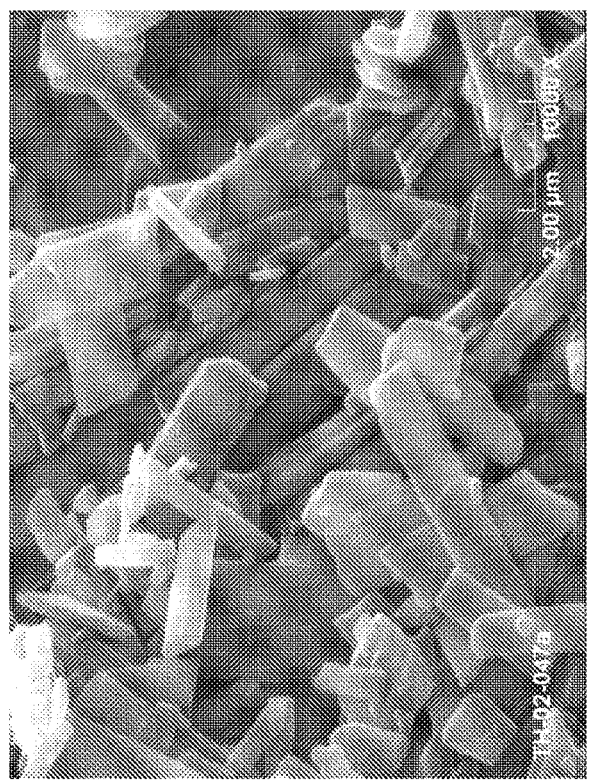

FIGS. 26A and 26B are Scanning Electron Micrographs of dried fluticasone propionate crystals prepared by the batch process.

Figure 27B:
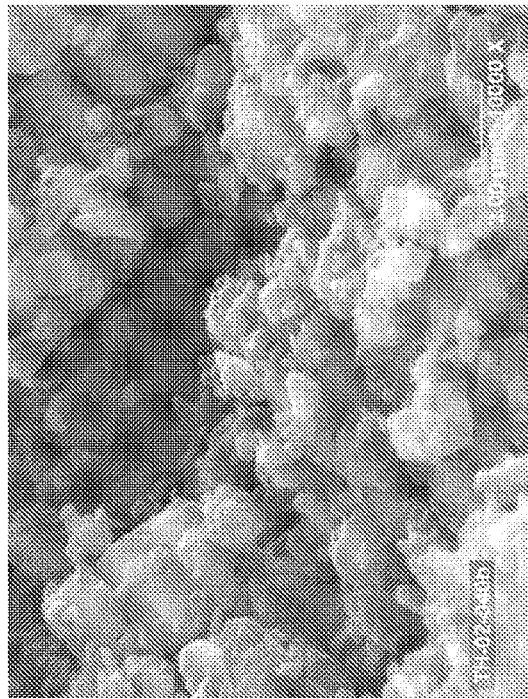
Figure 27A:
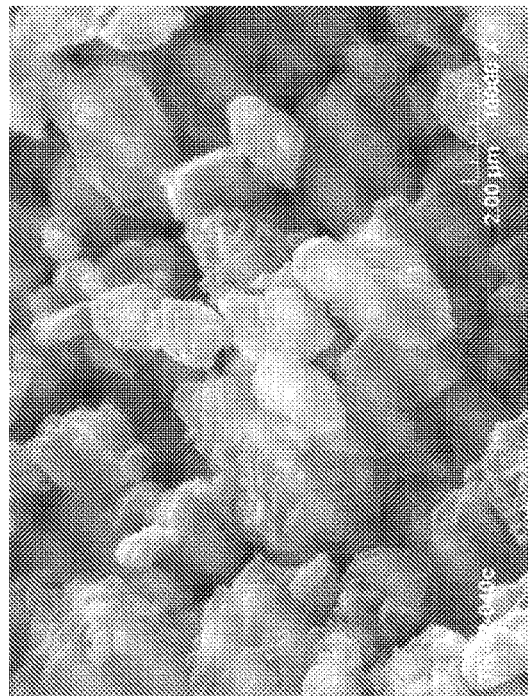

FIGS. 27A and 27B are Scanning Electron Micrographs of dried fluticasone propionate stock material and FP crystals prepared by homogenization respectively.

Figure 28A:
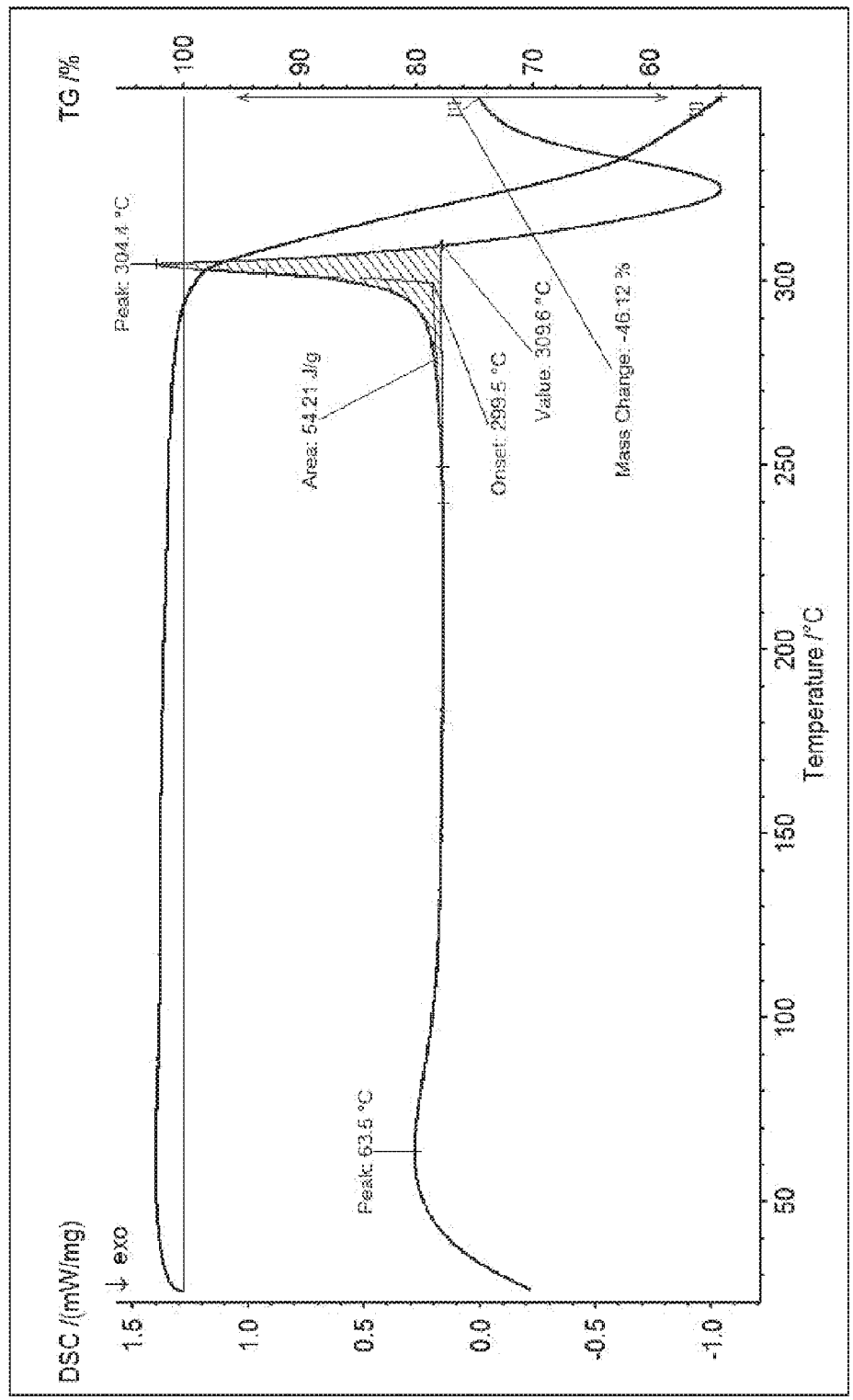
Figure 28B:
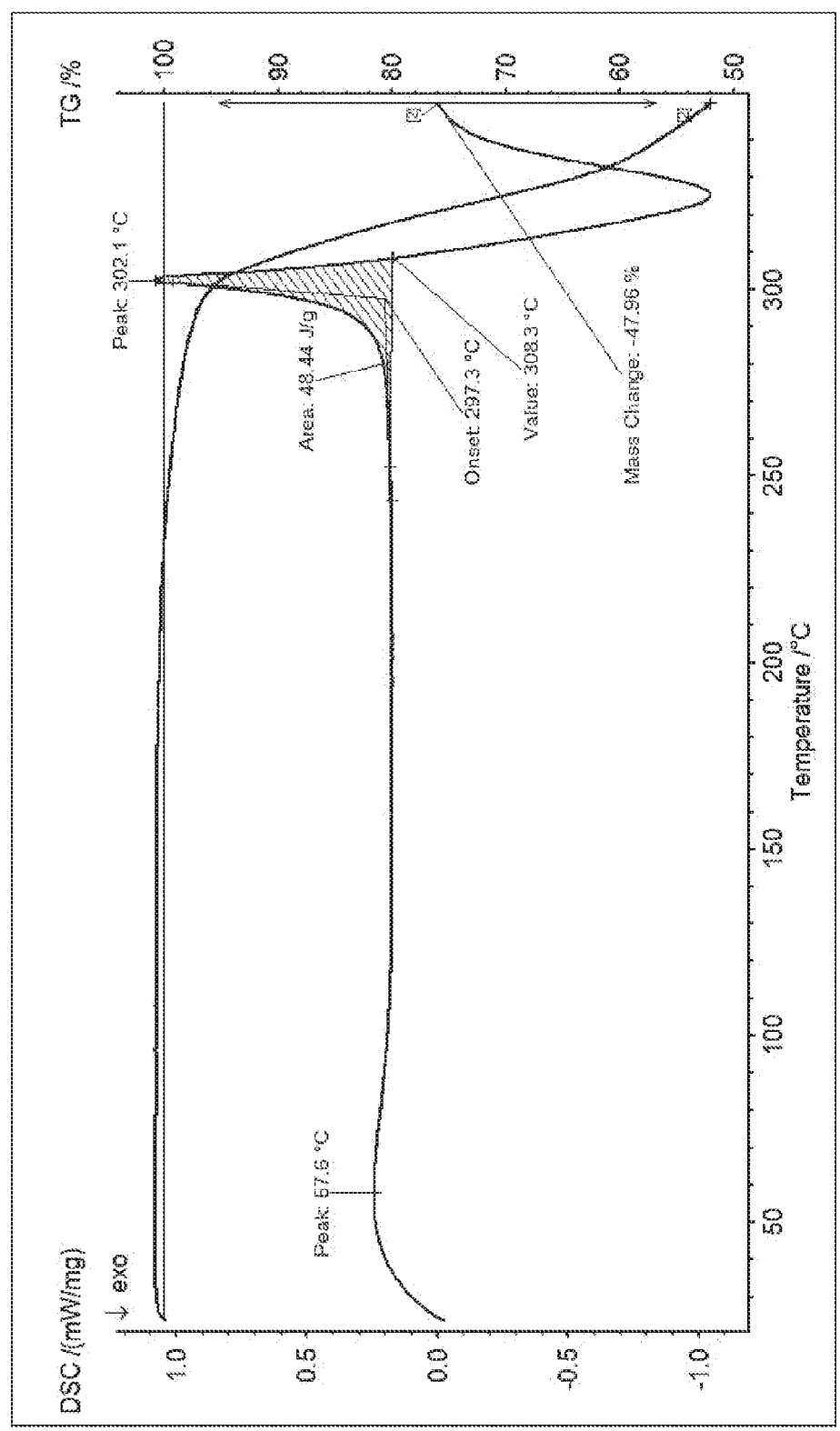

FIGS. 28A and 28B are combined DSC/TGA of fluticasone propionate nanocrystals produced by the batch process and FP stock material, respectively.

Figure 29:
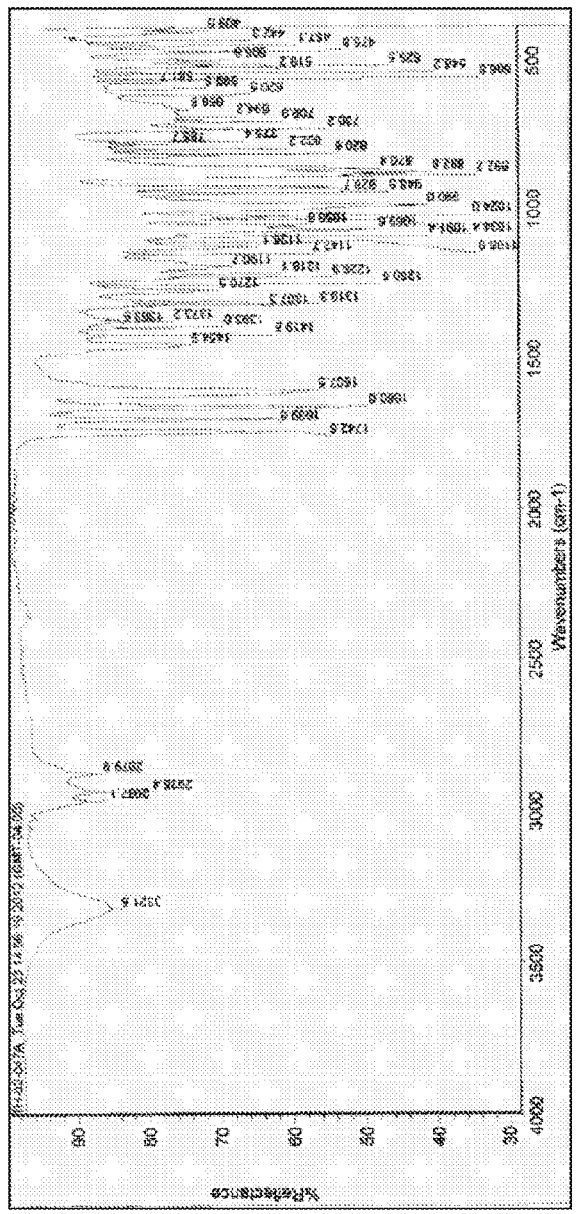

FIG. 29 is Fourier Transform Infrared Spectroscopic Scan of FP nanocrystals produced by the batch process of the invention.

Figure 30:
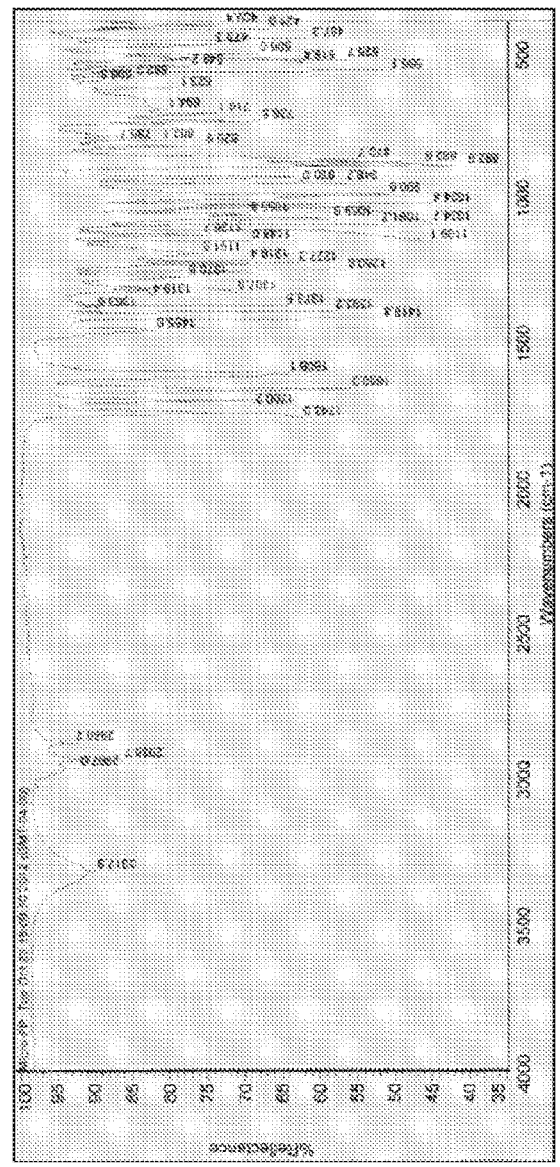

FIG. 30 is Fourier Transform Infrared Spectroscopic Scan of FP stock material.

Figure 31A:
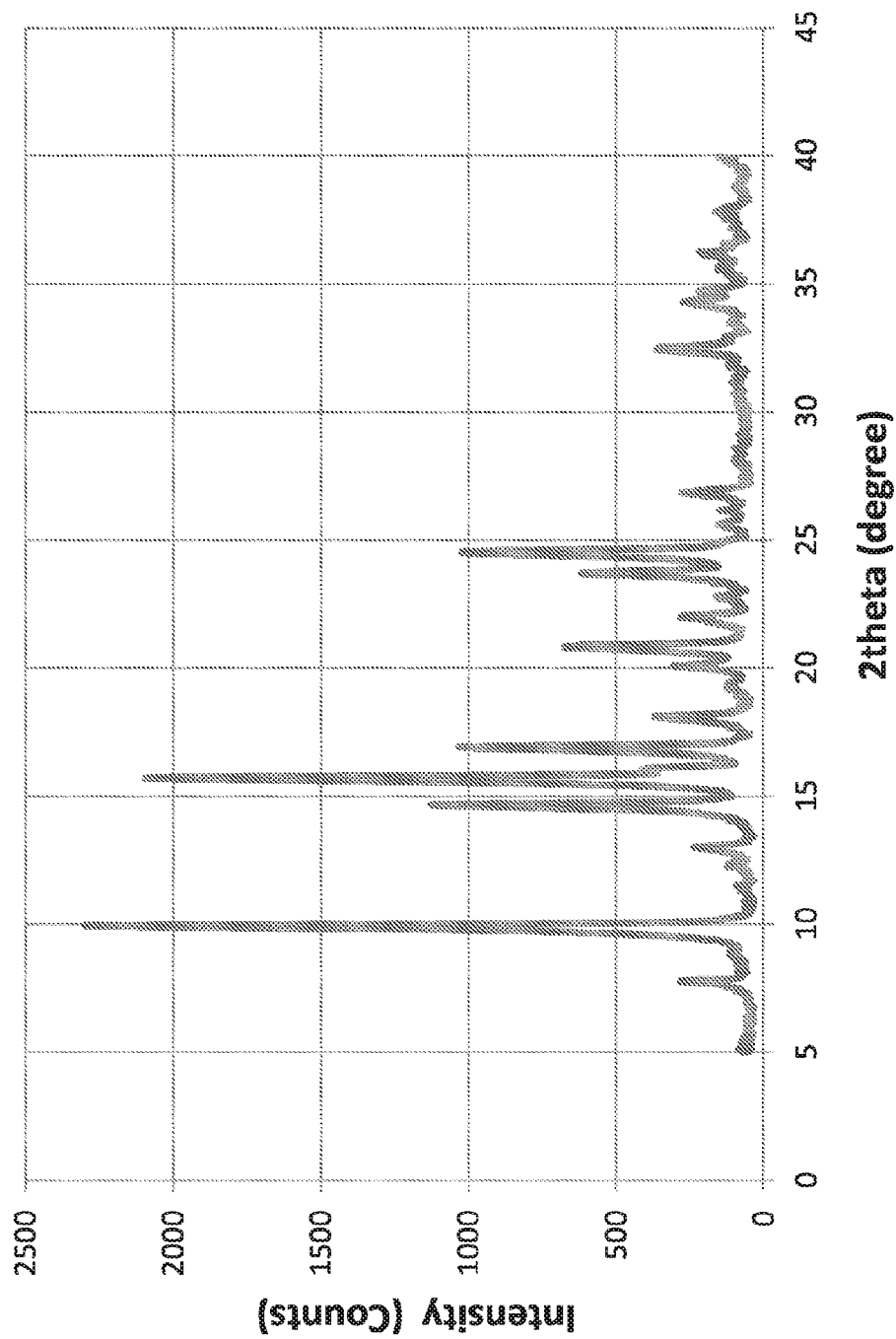

FIG. 31A is XRPD pattern of fluticasone propionate nanocrystals produced by the batch process (black).

Figure 31B:
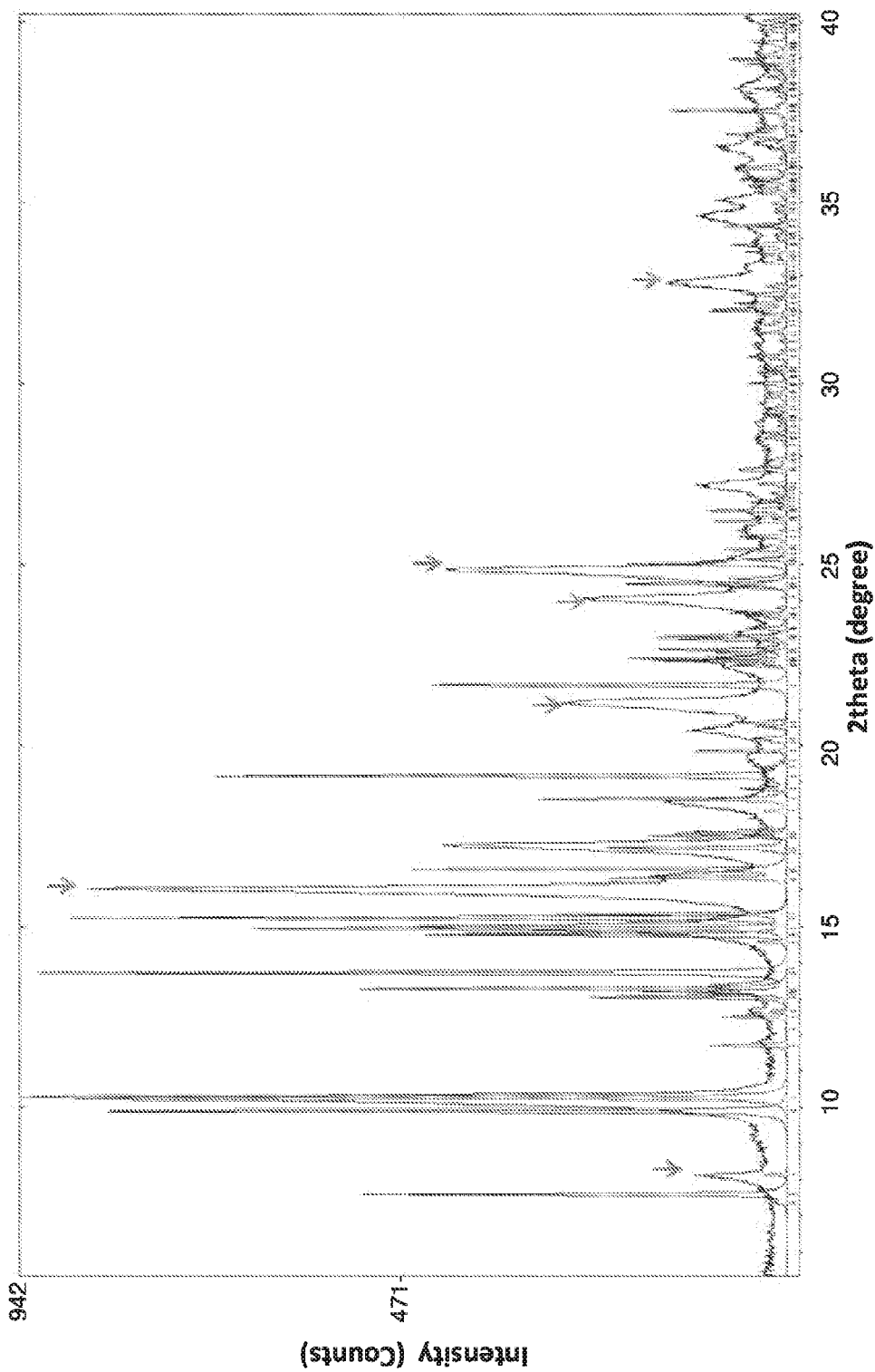

FIG. 31B is XRPD pattern of fluticasone propionate nanocrystals produced by the batch process (black) overlaid with the calculated XRPD pattern of polymorph 1 (red) and polymorph 2 (blue) overlaid. The blue arrows show some of the differences in the XRPD patterns.

Figure 32:
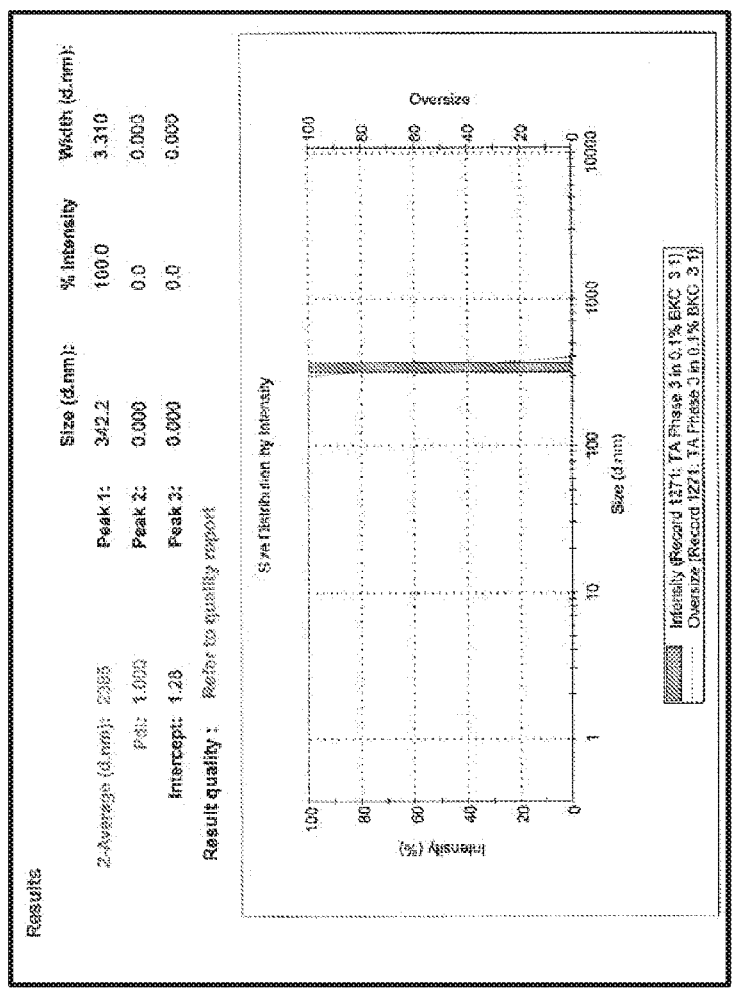

FIG. 32 is a plot showing size distribution of triamcinolone acetonide crystals produced by the methods of the invention.

Figure 33:
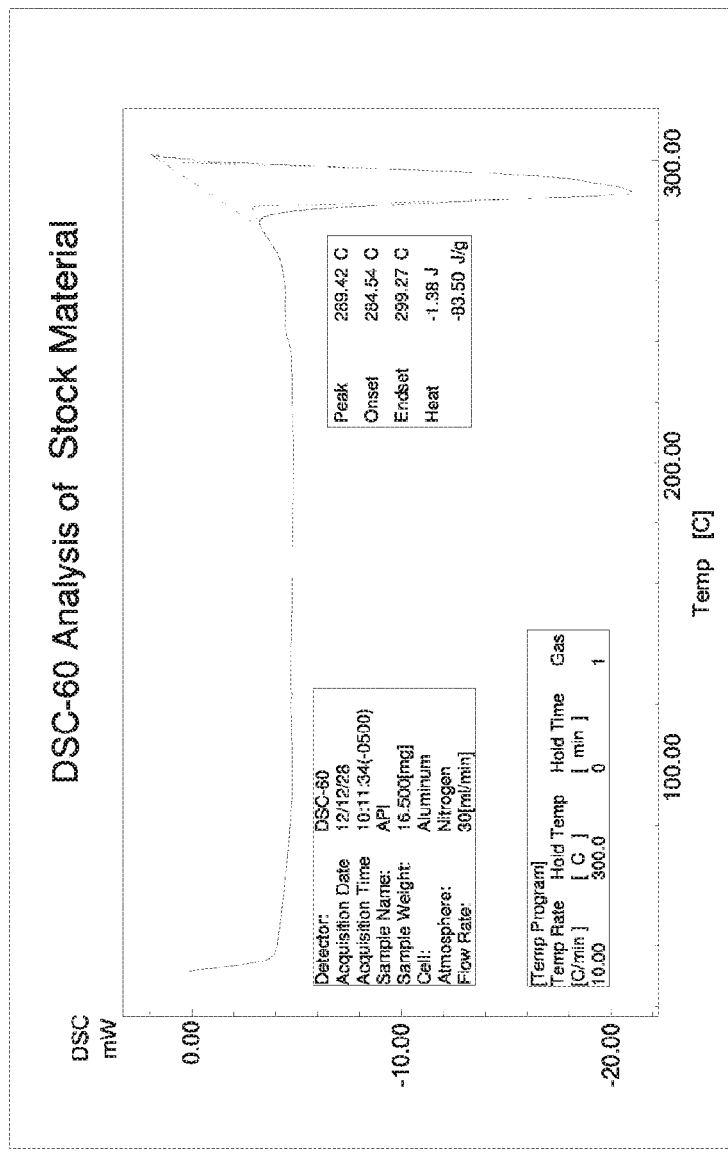

FIG. 33 is DSC scan of triamcinolone acetonide stock material.

Figure 34:
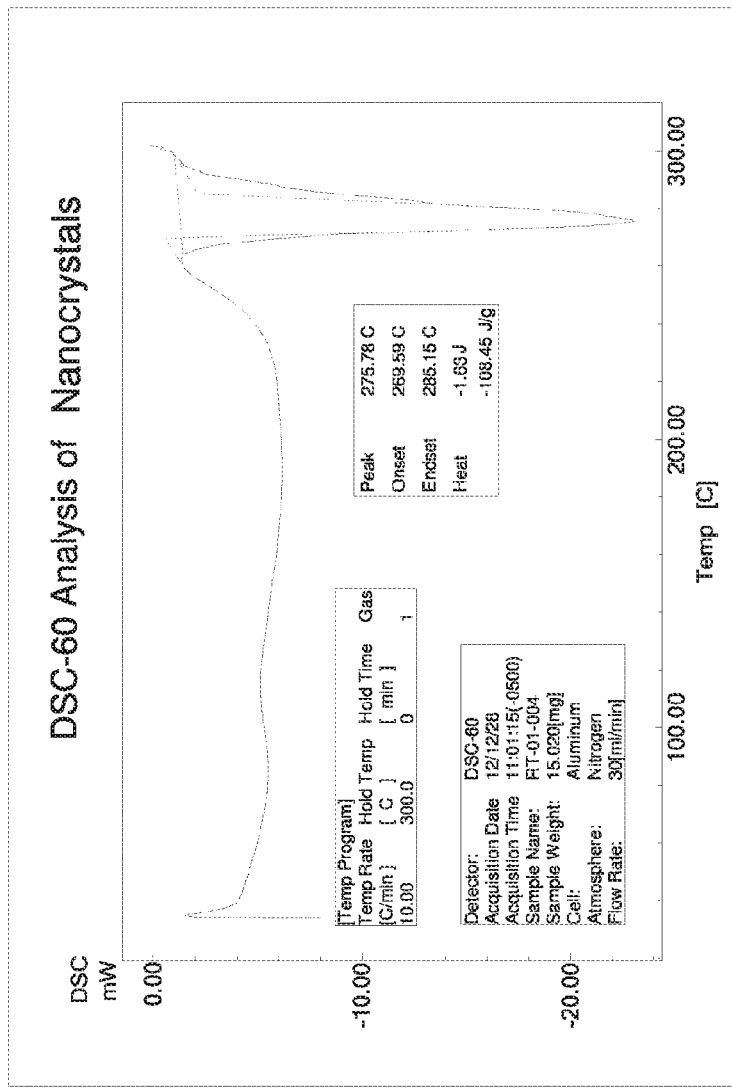

FIG. 34 is DSC scan of triamcinolone acetonide crystals produced by the methods of the invention.

Figure 35:
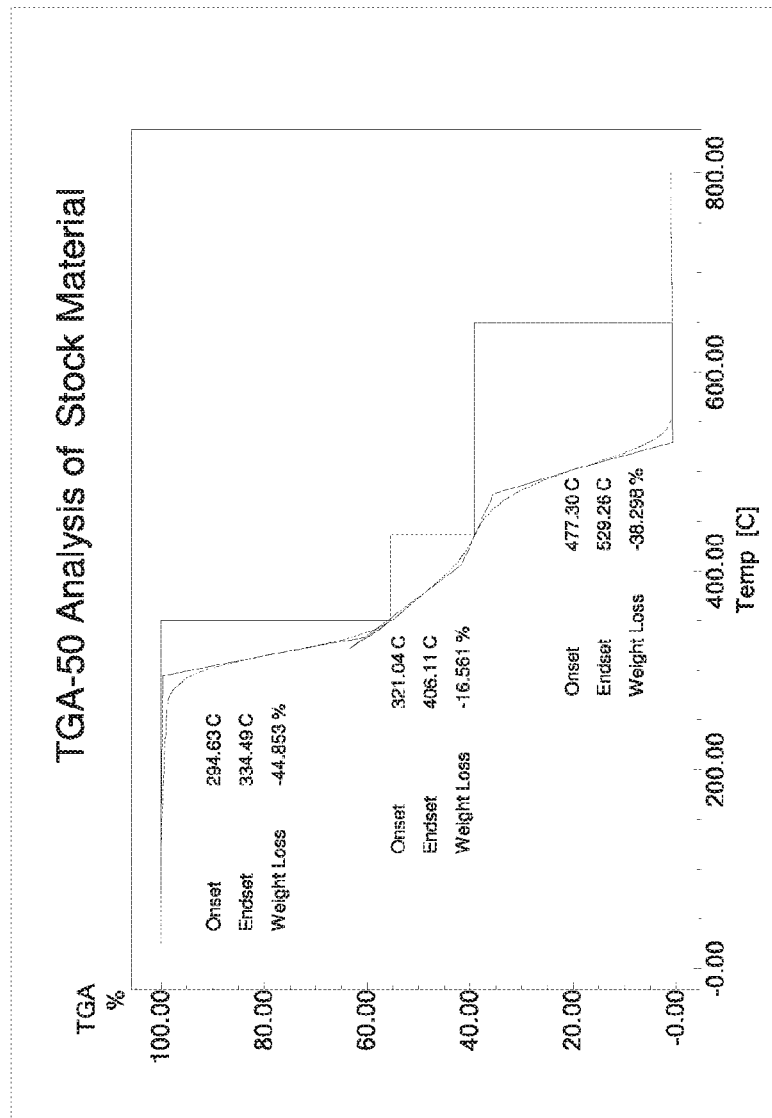

FIG. 35 is thermogravimetric analysis of triamcinolone acetonide stock material.

Figure 36:
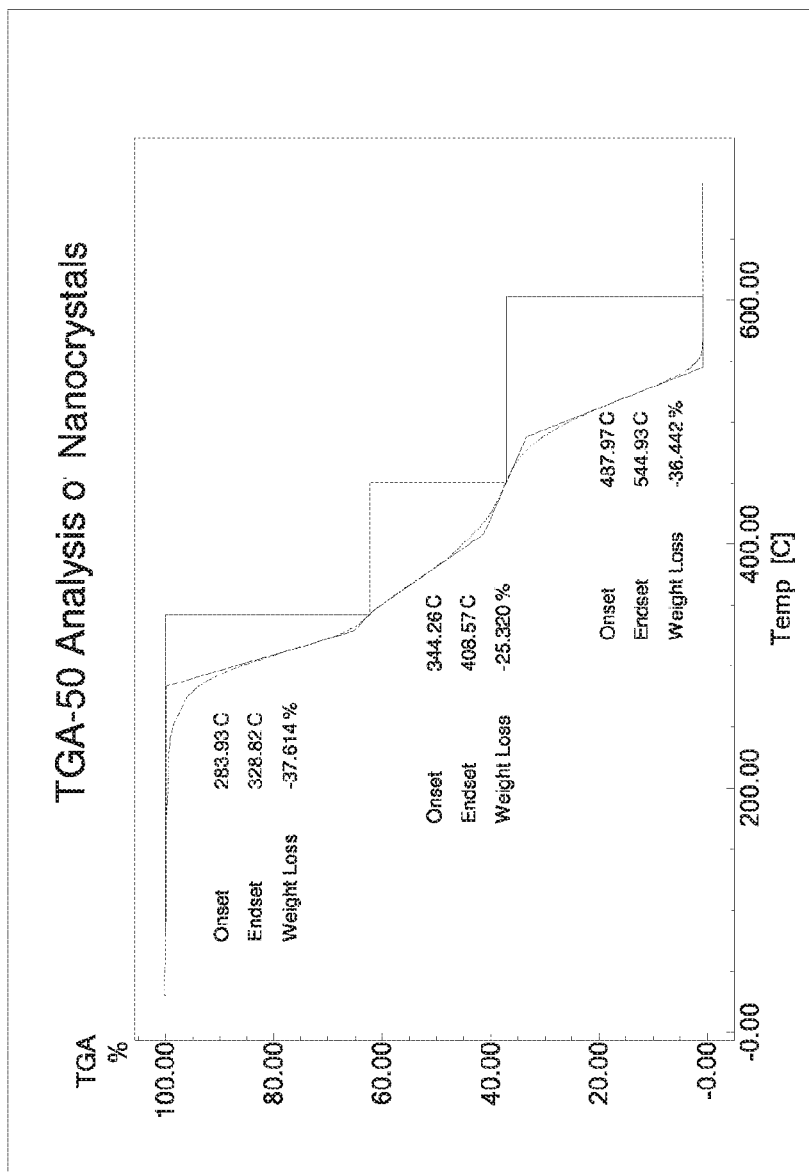

FIG. 36 is thermogravimetric analysis of triamcinolone acetonide crystals produced by the methods of the invention.

FIGS. 37A-E are Scanning Electron Micrographs of triamcinolone acetonide stock material and triamcinolone acetonide crystals prepared by the methods of the invention at different magnifications: A and B—triamcinolone acetonide stock material at 100× and 5000× magnifications respectively; C, D, and E-triamcinolone acetonide crystals produced by the methods of the invention at 100×, 5000× and 10,000× magnifications respectively.

Figure 38:
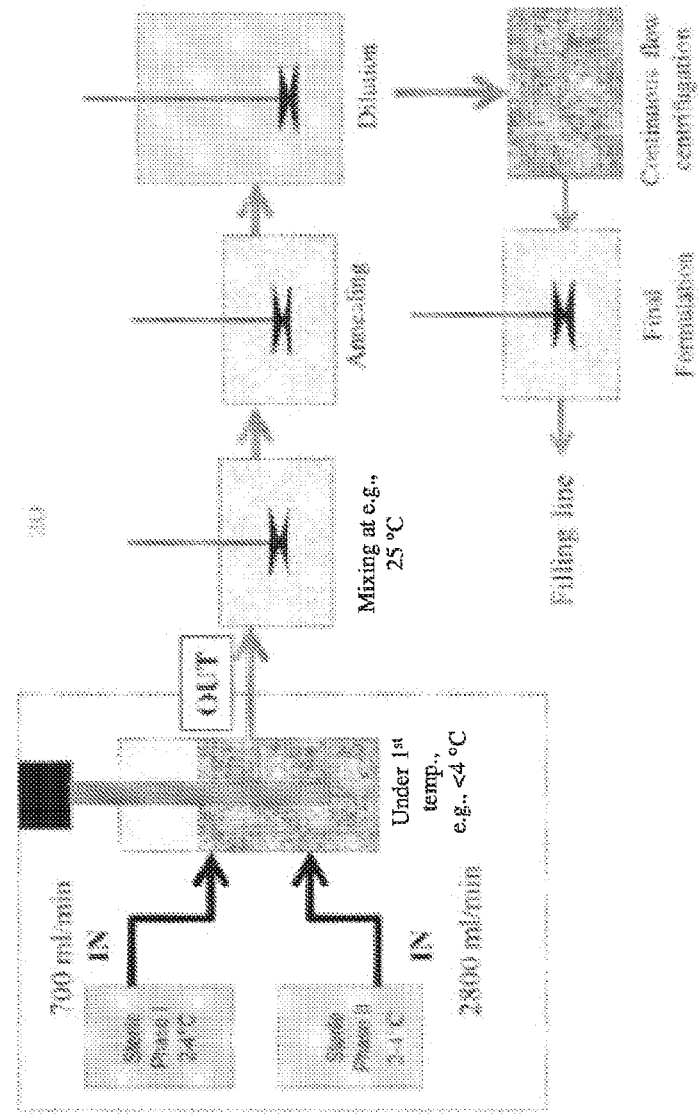

FIG. 38 is a schematic showing an embodiment of the process of the invention for production and purification process for fluticasone propionate nanocrystals.

Figure 39:
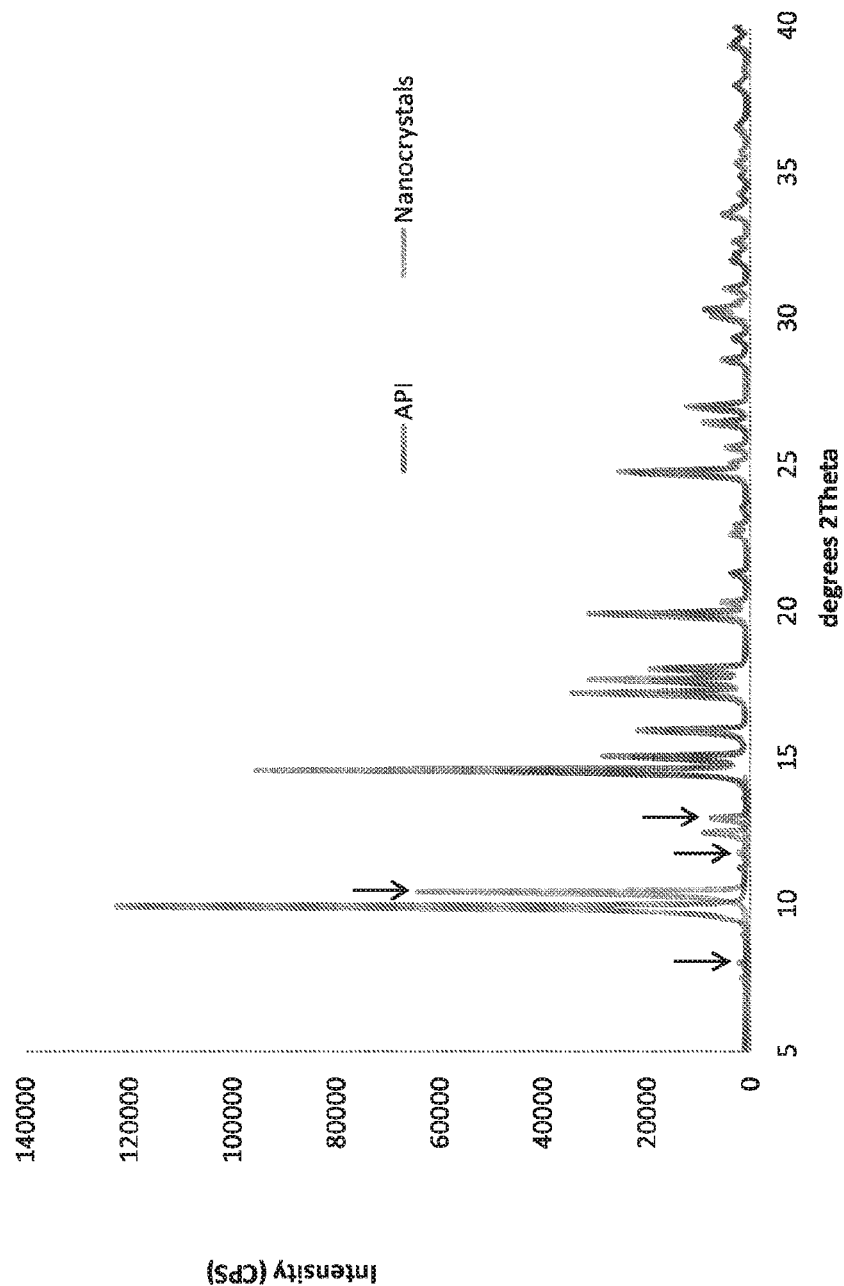

FIG. 39 is XRPD pattern of triamcinolone acetonide nanocrystals prepared by the methods of the invention (red) overlaid with the XRPD pattern of triamcinolone acetonide stock material (blue). The arrows show some of the differences in the XRPD patterns.

Figure 40:
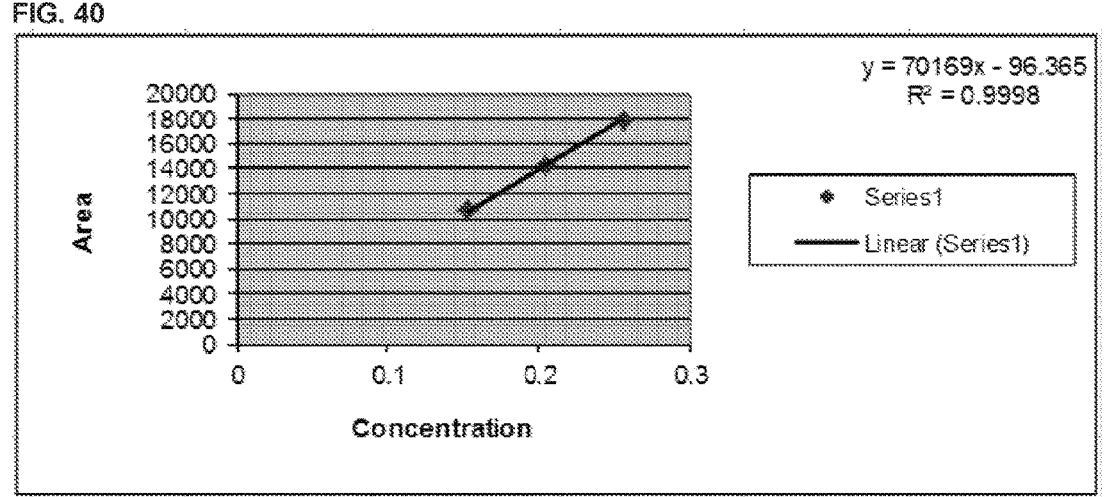

FIG. 40 is a plot showing the linearity of fluticasone propionate in formulation vehicle as set forth in Table 5.

Figure 41:
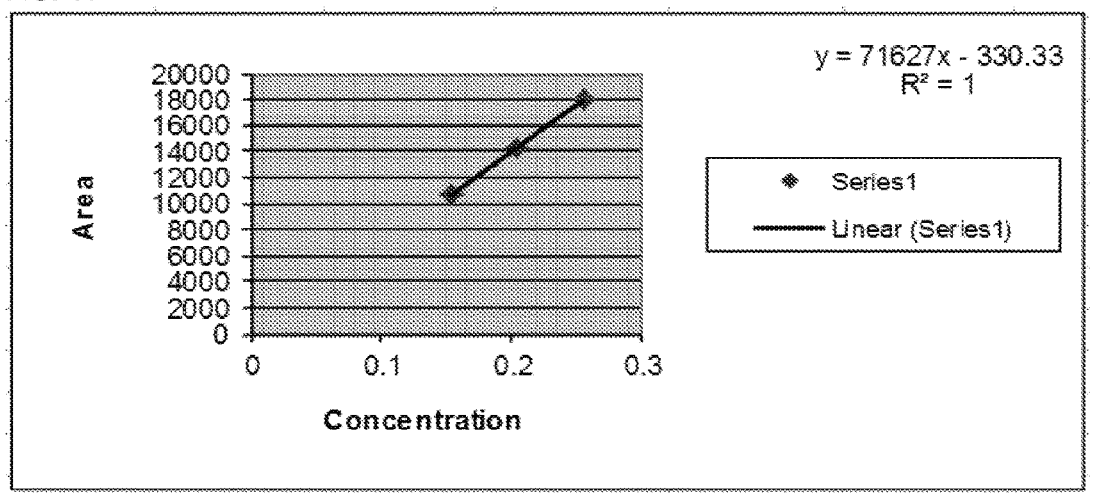

FIG. 41 is a plot showing the linearity of fluticasone propionate using mobile phase as a diluent as set forth in Table 6.

DETAILED DESCRIPTION OF THE INVENTION

The invention describes methods and compositions to produce sterile nanocrystals (optionally nanosuspensions) of hydrophobic therapeutic agents (such as fluticasone propionate) that are optimized to meet pharmaceutical standards of administration (e.g., topical or intranasal administration). The compositions produced by the methods are ideally suited for the topical treatment of inflammatory disorders such as ophthalmic disorders and dermatologic disorders. The compositions produced by the methods are also ideally suited for systemic or non-systemic treatment of disorders that the hydrophobic drugs in the compositions are used for, such as inflammatory disorders, respiratory disorders, autoimmune diseases, and cancer.

The drug nanocrystals made by the methods of the invention, when administered to a subject in need thereof, can be in various forms that are suitable for the specific route of administration, e.g. the form of eye drops, gels, ointments, dry powers, gels, aerosols, or a colloidal suspension (e.g., a liquid suspension). For example, the drug nanocrystals are the "dispersed" phase, suspended in another phase which is the "continuous" phase. A nanosuspension can be defined as colloidal dispersions of nanosized drug particles that are produced by a suitable method and stabilized by a suitable stabilizer or surface stabilizer. Unless otherwise specified, the terms "stabilizer," "surface stabilizer," and "steric stabilizer" are used interchangeably herein. In one embodiment, the drug is delivered or formulated for delivery via a systemic or local route. For example, the drug is delivered or formulated for delivery directly or via an applicator (e.g., a brush or swab). For example, the drug is delivered or formulated for delivery via a local route to a tissue, such as an ocular tissue and/or adnexa. The drug can be delivered or formulated for delivery via intraocular, intravitreal, subretinal, intracapsular, suprachoroidal, sub-tenon, subconjunctival, intracameral, intrapalpebral, cul-de-sac retrobulbar, or peribulbar injections. The drug can also be delivered or formulated for delivery via topical application to a tissue, such as an ocular tissue and/or adnexa. The drug can also be delivered or formulated for delivery via an implantable or surgical (e.g., drug delivery) device.

Nanosuspensions, such as nanocrystal suspensions, of insoluble drugs can dramatically lower its effective concentration by enhancing bioavailability. By "bioavailable" is meant dissolved drug that is molecularly available for absorption by cells.

Fluticasone propionate is almost insoluble in water with a solubility of 0.14 micrograms/ml. Since most ophthalmic suspensions are aqueous, the particle size of an insoluble drug determines its rate of dissolution into dissolved drug (or, bioavailable drug) at any given time. One way to enhance bioavailability is to ensure a completely dissolved drug solution. For insoluble drugs, the way to enhance the bioavailability of a water-insoluble drug is by utilization of micronized or nanosized dosage forms. In the case of fluticasone propionate, the rate of dissolution is dramatically enhanced by lowering the particle size. The release rate of fluticasone propionate particles of size 800-900 nm is many-fold that of that of particles>10 microns. Thus, nanosuspensions of fluticasone propionate have the potential to yield potent medications that are effective at concentrations that do not cause adverse side effects. At higher concentrations, fluticasone propionate can cause elevation of intraocular pressure leading to glaucoma and cataracts. An effective formulation of fluticasone propionate can be envisioned at lower concentrations, if the drug is nanoparticulate, or in a morphic form that is more water-soluble. For fluticasone propionate, the effective concentration in commercialized drug products range from 0.005% (e.g., CUTIVATE®) and 0.5% (e.g., FLONASE®). Thus, rendering a drug "effective" at concentrations not previously contemplated for that indication would be a surprising and unexpected result. Similarly, for triamcinolone acetonide, another hydrophobic drug (with a water solubility of 17.5 µg/mL at 28° C.), when the drug is nanoparticulate form generated e.g., via the methods of the invention, an effective formulation of TA can be obtained at unexpectedly lower concentrations of TA not previously contemplated for a particular indication.

Thus, in the design of topical medications that require immediate relief, then sustained relief, it is surmised that a nanocrystaline suspension that is also bioadhesive, will assist in enhancing the residence time of the drug, while increasing the bioavailability at the same time. In the examples described in this invention, fluticasone propionate suspensions were developed for the treatment of blepharitis, which is characterized by inflammation and infection of the eyelid. However, the fluticasone propionate compositions described herein can also be utilized for the prevention or treatment of other ophthalmic inflammatory conditions. For example, the compositions described in the invention can be used for post-operative care after surgery. For example, the composition of the invention can be used to control of pain after surgery, control of inflammation after surgery, argon laser trabceuloplasty and photorefractive procedures. Furthermore, the fluticasone propionate compositions can be used to treat other ophthalmic disorders such as ophthalmic allergies, allergic conjunctivitis, cystoid macular edema uveitis, or meibomian gland dysfunction. Additionally, the fluticasone propionate compositions can be used to treat dermatologic disorders such as atopic dermatitis, dermatologic lesion, eczema, psoriasis, or rash.

Challenges of Stable Nanocrystal Fabrication of Hydrophobic Drugs

The successful fabrication of nanosuspensions has two major challenges. The first challenge is the generation of particles that are of the desired size. For most drugs that are insoluble in water, the desired particle size is submicron, ranging from the low nm to the high (10-990 nm). The second step is maintaining particle size long-term. Both steps are challenging.

Drug suspensions are normally prepared by "top-down" techniques, by which the dispersion is mechanically broken into smaller particles. Techniques such as wet milling, sonication, microfluidization and high pressure homogenization are examples of this technique to create micronized and nanosized particles. In high pressure homogenization, the nanocrystal size resulting from the process depends not only on the hardness of the drug material but also on the homogenization pressure and cycle number. It does not, however, depend on the type of stabilizer. Thus, the efficiency of the stabilizer—whether or not it is able to prevent aggregation of the particles—is shown after processing and during storage. Accordingly, it is extremely important to understand the phenomena involved in particle formation in the particular process used.

During milling or mechanical particle size reduction methods, two opposite processes are interacting in the milling vessel: fragmentation of material into smaller particles and particle growth through inter-particle collisions. The occurrence of these two opposite phenomena is dependent on the process parameters. Often after a certain timepoint, the particle size has achieved a constant level and continuing the milling does not further decrease the particle size. In some cases an increase in grinding time may even lead to a gradual increase of particle size and heterogeneity of the material, while decreased particle sizes are achieved with decreased milling speeds. Changes in the physical form or amorphization are also possible during the milling. Mechanical pressure above certain critical pressure values increases lattice vibrations, which destabilize the crystal lattice. The number of defects increases and transformation into an amorphous state occurs above a critical defection concentration. The high stresses on the drug crystals during particle reduction techniques result in destabilization of the crystal structure, loss in crystallinity and sometimes, shift to less stable polymorphic forms. Creation of amorphous regions in the crystalline structures leads to gradual increase in particle size as the suspension shifts back into a stable, crystalline morphology.

Another challenge for nanocrystal fabrication is gradual growth in the size of the particles, also called "Ostwald Ripening". Crystal growth in colloidal suspensions is generally known as Ostwald ripening and is responsible for changes in particle size and size distribution. Ostwald ripening is originated from particles solubility dependence on their size. Small crystals have higher saturation solubility than larger ones according to Ostwald-Freundlich equation, creating a drug concentration gradient between the small and large crystals. As a consequence, molecules diffuse from the higher concentration surrounding small crystals to areas around larger crystals with lower drug concentration. This generates a supersaturated solution state around the large crystals, leading to drug crystallization onto the large crystals. This diffusion process leaves an unsaturated solution surrounding the small crystals, causing dissolution of the drug molecules from the small crystals into the bulk medium. This diffusion process continues until all the small crystals are dissolved. The Ostwald ripening is essentially a process where the large particles crystals at the expense of smaller crystals. This subsequently leads to a shift in the crystals size and size distribution of the colloidal suspension to a higher range. Dispersions with dissolved drug in the continuous phase also invariably lead to instability in particle size.

Another challenge with nanocrystals is agglomeration, or clumping of particles. The stabilizer plays a critical role in stabilizing the dispersion. The stabilizer needs to adsorb on the particle surfaces in order for proper stabilization to be achieved. Furthermore, the adsorption should be strong enough to last for a long time. Adsorption of the stabilizer may occur by ionic interaction, hydrogen bonding, van der Waals or ion-dipole interaction or by hydrophobic effect.

Possible interactions between the functional groups of a stabilizer and drug materials always need to be considered before selecting the drug-stabilizer pair. Many drugs have structures containing functionalities like phenols, amines, hydroxyl groups, ethers or carboxylic acid groups, which are capable of interactions. Strong ionic interactions, hydrogen bonding, dipole-induced forces, and weak van der Waals or London interactions may enhance or disturb particle formation. The concentration level of the stabilizer is also important. The adsorption/area is a surface property that does not usually depend on particle size. As the adsorbed amount correlates to the surface area, this means that the total amount of stabilizer is directly related to the crystals size. Adsorption of polymer molecules onto the crystals surfaces takes place when the free energy reduction due to the adsorption compensates the accompanying entropy loss. Because steric stabilization is based on adsorption/desorption processes, process variables such as the concentration of the stabilizer, particle size, solvent, etc. are important factors for the effectiveness of the stabilizer.

Another way to stabilize the crystals size has been in the spray-drying of the particulate suspension in the presence of specific stabilizers, a technique that has been used to generate aerosolized microparticles of fluticasone propionate. Combinations of top-down methods are also used to generate particles of the desired size. Yet another method to stabilize the particle size has been to lyophilize the particulate suspension.

The other method commonly used to create nanosuspensions is the antisolvent precipitation method, whereupon a drug solution is precipitated as nanocrystals in an antisolvent. This approach is called the "bottom-up" crystallization approach, whereupon the nanocrystals are produced in-situ. The precipitation of the drug as nanocrystals is usually accompanied by homogenization or sonication. If the drug is dissolved in an organic solvent such as acetone prior to precipitation, the organic solvent has to be removed after formation of the particles. This is usually performed by evaporation of the solvent. This evaporative step poses challenges to this method of particle formation, since the process of evaporation can alter the dynamics of particle stabilization, often seen as rapid increases in particle size. Furthermore, residual levels of organic solvents often remain bound to excipients used in the formulation. Thus, this method, though explored, has its challenges and is generally not preferred.

The nanocrystals of a hydrophobic drug produced by the process defined in this invention do not use toxic organic solvents that need removal and do not display particle instability defined in the sections above.

Core Features the Invention

This invention provides a sonocrystallization/purification process that can produce nanocrystals of a drug (e.g., a hydrophobic drug) or suspensions containing the nanocrystals. The process: (a) incorporates sterile filtration of all components prior to production of the nanocrystals, (b) produces the crystals at the desired size, (c) stabilizes the nanocrystals by the use of specific steric stabilizing compositions, in combination with annealing at specific temperatures, (d) provides the formulator the flexibility to purify the particles by replacing the original continuous phase with another continuous phase and (d) provides the flexibility to achieve a final desired concentration of drug in the final formulation vehicle. In step (d), the significance of the purification step may be a key and critical aspect of the invention, since the composition that produces and stabilizes the particles at a desired size is nuanced and dependent upon parameters of ionic strength, polymer molecular weight and structure and pH. The composition used to create the particles is usually not the composition the formulator envisions as the final formulation, or the final drug concentration. This is addressed by spray-drying, or lyophilization. The nanocrystals produced by this process are of the size range 100 nm-500 nm, 500-900 nm, 400-800 nm and 900 nm to 10000 nm. Preferably the nanocrystals are of the size range of 400-800 nm (e.g., 400-600 nm). The size and size distribution of nanocrystals of the invention can be determined by conventional methods such as dynamic light scattering (DLS), scanning electron microscopy (SEM), transmission electron microscopy (TEM), and X-ray Power Diffraction (XRPD). In this invention, the nanocrystals are purified by exchange with the final biocompatible, tissue-compatible buffer.

Two-Part Process: The process is characterized by a two-part process to prepare nanocrystals, defined as Step 1 and Step 2. Optionally, the process is a single step, whereupon the final formulation is prepared in a single step (only, Step 1). For the two-step process (Step 1, followed by Step 2), the first part of the process is nanocrystal production at the desired size (Step 1). The second part of the process is nanocrystal purification to yield highly pure nanocrystals suspended at the desired drug concentration and optimized excipient composition for the final formulation (Step 2).

Drug Concentrations: In a preferred embodiment, the initial nanocrystal concentration (after Step 1) is at 0.1% drug (e.g., a corticosteroid such as FP), but the final formulation may be as high as 10% (after Step 2). The initial concentration of the suspension may be less than 0.1% (in Step 1) and concentrated to 10% during the purification process (Step 2) with the same vehicle composition, or a different vehicle composition. The initial concentration of the suspension may be 0.1% or less than 0.1%, preferably 0.06%. The initial suspension may be purified to a lower concentration (in Step 2) with the same vehicle composition, or a different vehicle composition. In a preferred composition, the initial suspension may be formed at 0.06% (in Step 1) and purified to 0.06% or lower (in Step 2) with the same initial vehicle composition, or a different vehicle composition. The initial concentration of the nanosuspension may be 1%, 1%-0.5%, 0.5%-0.1%, 0.1%-0.05%, 0.05%-0.01%, 0.01%-0.005%, 0.005%-0.001%, 0.001%-0.0005%, 0.0005%-0.0001%, 0.0001%-0.00001%.

Step 1 comprises dissolution of the drug in FDA-approved excipients to create Phase I. The solution (Phase I) is then sterile filtered through a 0.22 micron PVDF (polyvinylidene fluoride) filter. A solution containing a specific composition of a steric stabilizer at certain viscosity, pH and ionic strength is prepared. This is Phase II. In one embodiment, the drug is a steroidal drug. In a preferred embodiment, the drug is fluticasone propionate. In another preferred embodiment, the drug is fluticasone furoate. In another embodiment, the drug is any salt form of fluticasone propionate.

In one embodiment, Step 1 includes:

providing a phase I solution (e.g., a sterile solution) comprising a hydrophobic therapeutic agent and a solvent for the hydrophobic therapeutic agent;

providing a phase II solution (e.g., a sterile solution) comprising at least one surface stabilizer and an antisolvent for the hydrophobic therapeutic agent;

mixing the phase I solution and the phase II solution to obtain a phase III mixture, wherein the mixing is performed at a first temperature not greater than 25° C.;

annealing the phase III mixture at a second temperature that is greater than the first temperature for a period of time ($T_1$) such as to produce a phase III suspension comprising a plurality of nanocrystals of the hydrophobic therapeutic agent, and optionally purifying the nanocrystals by, e.g., tangential flow filtration, hollow fiber cartridge filtration, or centrifugation (e.g., continuous flow centrifugation).

Optionally, centrifugation is performed at about 1.6 L/min at about 39,000×g.

Optionally, Step 1 includes a dilution step with a solution following the annealing step and prior to the purification step. For example, the dilution step includes re-dispersing the nanocrystals in a solution. The solution used for dilution can include about 0.002-0.01% (e.g. 50 ppm±15%) benzalkonium chloride, 0.01-1% polysorbate 80 (e.g., about 0.2%), 0.01-1% PEG40 stearate (e.g., about 0.2%), buffering agent (e.g., citrate buffer, pH 6.25), and water. A pellet formed during purification (e.g., during centrifugation) is re-dispersed into a final formulation (see, e.g., FIG. 38). The pellet can be added into a suitable aqueous solution to redisperse the nanocrystals contained in a mixer (e.g., a SILVERSON® Lab Mixer). The redisperion can be performed at room temperature at 6000 RPM for about 45 mins or longer (e.g., about 60 mins or longer) to obtain a final formulation that meets FDA criteria for ophthalmic or dermatologic administration. The formulation may contain one or more pharmaceutically acceptable excipients.

For example, the hydrophobic therapeutic agent is a steroid.

For example, the hydrophobic therapeutic agent is fluticasone propionate or triamcinolone acetonide.

For example, the at least one surface stabilizer comprises a cellulosic surface stabilizer such as methyl cellulose.

For example, the methyl cellulose has a molecular weight of not greater than 100 kDa.

For example, the cellulosic stabilizer (e.g., methyl cellulose) used for the phase II solution has a viscosity between 4 cP and 50 cP, e.g., 15-45 cP.

For example, the first temperature is, e.g., not greater than 20° C., not greater than 8° C., e.g., <4° C., or <2° C. or 0-4° C.

For example, the second temperature, i.e., the annealing temperature, is between 20° C. and 60° C.

For example, the annealing step is necessary for decreasing the particle size of the nanocrystals and/or for hardening the nanocrystals (e.g., to increase to hardness of the nanocrystals).

For example, continuous flow centrifugation is performed at about 1.6 L/min at about 39,000×g.

For example, the nanocrystals produced by the methods described herein have an average size between 10 nm and 10000 nm (e.g., 50-5000 nm, 80-3000 nm, 100-5000 nm, 100-2000 nm, 100-1000 nm, or 100-800 nm).

For example, the nanocrystals produced by the methods described herein have a particle size suitable for delivery by micro needles (i.e., 27-41 gauge). For example, when injected in the suprachoroidal space of the eye, the nanocrystals can be efficiently delivered to the back of the eye or will dissolve more slowly so that the drug treats target tissues without leeching into front-of-eye tissues, such as lens, ciliary body, vitreous, etc., thereby minimizing ocular side effects, such as high intraocular pressure (TOP) or cataract formation.

For example, the nanocrystals produced by the methods described herein have a narrow range of size distribution. In other words, the nanocrystals are substantially uniform in size.

For example, the ratio of the nanocrystals' D90 and D10 values is lower than 10, e.g., lower than 5, lower than 4, lower than 3, lower than 2, or lower than 1.5. For example, the nanocrystals have a size distribution of 50-100 nm, of 100-300 nm, of 300-600 nm, of 400-600 nm, of 400-800 nm, of 800-2000 nm, of 1000-2000 nm, of 1000-5000 nm, of 2000-5000 nm, of 2000-3000 nm, of 3000-5000 nm, or of 5000-10000 nm.

For example, the nanocrystals produced by the methods described herein have D90 value of not greater than 5000 nm (e.g., not greater than 4000 nm, not greater than 3000 nm, not greater than 2000 nm, not greater than 1000 nm, not greater than 900 nm, not greater than 800 nm, not greater than 700 nm, not greater than 700 nm, not greater than 600 nm, not greater than 500 nm, not greater than 400 nm, not greater than 300 nm, not greater than 200 nm, not greater than 100 nm, or not greater than 80 nm).

For example, the nanocrystals produced by the methods described herein are coated with methyl cellulose.

For example, the methyl cellulose-coated nanocrystals produced by the methods described herein are stable, e.g., they do not aggregate.

For example, the nanocrystals produced by the methods described herein are fluticasone propionate nanocrystals having a size distribution of 400-600 nm.

For example, the nanocrystals produced by the methods described herein are triamcinolone acetonide nanocrystals having a size distribution of 300-400 nm.

For example, the nanocrystals produced by the methods described herein are either in the form of a liquid suspension or dry powder.

For example, the nanocrystals produced by the methods described herein have a concentration of from 0.0001% to 10%, to 20%, to 30%, to 40%, to 50%, to 60%, to 70%, to 80%, to 90%, to 99%, or to 99.99%.

For example, sonication is applied when mixing the phase I and II solutions.

For example, the methyl cellulose is at a concentration ranges from 0.1% to 0.5% (e.g., 0.2-0.4%) in the phase II solution.

For example, the phase II solution further includes a second stabilizer, e.g., benzalkonium chloride at a concentration ranges from 0.005% to 0.1% (e.g., 0.01-0.02%).

For example, the phase II solution has pH of 5.5 when the hydrophobic drug is fluticasone propionate.

For example, the phase II solution has pH of about 4 when the hydrophobic drug is triamcinolone acetonide.

For example, the solvent of phase I solution comprises a polyether.

For example, the polyether is selected from polyethylene glycol (PEG), polypropylene glycol (PPG), and a mixture thereof.

For example, the polyether is selected from PEG400, PPG400, PEG40-stearate, and a mixture thereof.

For example, the PEG 400 is at a concentration of about 20 to 35% in the phase I solution.

For example, the PPG 400 is at a concentration of about 65% to 75% in the phase I solution.

For example, the solvent of phase I solution comprises one or more polyols such as monomeric polyols (e.g., glycerol, propylene glycol, and ethylene glycol) and polymeric polyols (e.g., polyethylene glycol).

For example, the solvent of phase I solution comprises one or more monomeric polyols.

For example, the phase I solution further comprises a surface stabilizer.

For example, the surface stabilizer in the phase I solution is TWEEN 80® (polysorbate 80), e.g., at a concentration of about 7.0% to 15% in the phase I solution.

For example, the concentration of hydrophobic drug in the phase I solution is about 0.1-10%, e.g., 0.1 to 5.0%, 0.2-2.5%, or 0.4 to 10%.

For example, when the hydrophobic drug is FP, the concentration of FP in the phase I solution is about 0.1-10%, e.g., 0.4 to 1.0%.

For example, the volume ratio of the phase I solution to phase II solution ranges from 1:10 to 10:1 (e.g., 1:3 to 3:1, or 1:2 to 2:1, or about 1:1).

For example, the cellulosic surface stabilizer is methylcellulose with a molecular weight of not greater than 100 kDa, the first temperature is a temperature between 0° C. and 5° C., the second temperature is a temperature between 10° C. and 40° C., and $T_1$ is at least 8 hours.

The methods of the invention allows manufacturing drug crystals of in tight particle size distribution (PSD) ranges from very small sizes (e.g., <75 nm) to larger sizes (e.g., 5,000 nm) and allows use of specific sized particles, either alone, or in combination with smaller or larger sized particles of the same drug crystals made via the methods described herein, or in combination with a different form of the drug (e.g., stock material or form obtained by homogenization) or with other excipients (such as solvents, demulcents, mucoadhesives) to control the release, distribution, metabolization or elimination of, or to enhance tissue penetration or tissue residence time of such drug.

In one embodiment, the drug suspension is prepared in a static batch reactor, using sonication (e.g., ultrasonication) or ultrahomogenization to disperse the precipitating drug in the antisolvent. In one embodiment, the ultrasonicating process is accomplished by placing in a sonicating bath, providing ultrasound energy to the entire fluid. In another embodiment, the ultrasonicating process is accomplished using a probe sonotrode. In yet another embodiment, the dispersion step during precipitation of the drug in the antisolvent, is high pressure homogenization.

In another embodiment, the drug suspension is prepared in a flow-through reactor, during ultrasonication or ultrahomogenization. The temperature of the solution may be 0-4 or 2-8 degrees centigrade. In another embodiment, the temperature of the solution may be 22-30 degrees centigrade. The flow-through reactor may be jacketed to be temperature-controlled.

The drug solution (Phase I) is metered into the reactor by means of a syringe pump. In another embodiment, the drug suspension is metered into the reactor by means of other automated pump devices. The flow rate of Phase I may be in the range 0.1 ml/min to 40 ml/min. In the flow-through reactor (or flow reactor), the flow rate of Phase I may be in the range 0.1 ml/min to 40 ml/min or 0.5 to 900 ml/min (e.g., 0.5-2.0 ml/min, 10-900 ml/min, 12-700 ml/min, 50-400 ml/min, 100-250 ml/min, or 110-130 ml/min). In the flow-through reactor, the flow rate of Phase II may be in the range 0.1 ml/min to 40 ml/min or 2.5-2100 ml/min (e.g., 2.5-900 ml/min, 2.5-2.0 ml/min, 10-900 ml/min, 12-700 ml/min, 50-400 ml/min, 100-250 ml/min, or 110-130 ml/min).

Components of Phase I and Phase II in Step 1: The excipients used to dissolve the drug to create the solution in Phase I are selected such that they are miscible and soluble in Phase II. Phase II components are such that this phase acts as an antisolvent only for the drug. As phase I is added to phase II in the presence of sonication, the drug precipitates into nanocrystals. Phase II is sterile-filtered through a 0.22 micron PVDF filter into a holding container maintained at 0-4° C. or 2-8° C. Phase II is metered into a cell fitted with a sonotrode, or sonicating probe. The Phase I solution is then metered into the cell into Phase II drop-wise, while sonicating. The nanocrystals produced by Step 1 can be held in a holding tank at 2-8° C., or 22-25° C. or 30-40° C. This process of "holding" is called annealing to stabilize the nanocrystals produced in Step 1. Annealing, or physical ageing of the nanosuspension produced in Step 1, allows the drug molecules to "relax" and arrange in its most stable thermodynamic state. The choice of the annealing temperature is dependent upon the physiochemical characteristics of the drug. Time duration of annealing is also important. In one embodiment, the duration of annealing is 30 minutes. In another embodiment, the duration of annealing is between 30 minutes and 90 minutes. In another embodiment, the duration of annealing is between 90 minutes and 12 hours. In another embodiment, the duration of annealing is between 12 hours and 24 hours.

The components of Phase I and Phase II are of low viscosity, so that each phase can be sterile filtered through a 0.22 micron filter. Alternatively, the sterile filtration can be accomplished by other means of sterilization such as autoclaving, gamma irradiation, ethylene oxide (ETO) irradiation.

The solvents to create Phase I for the initial nanosuspension may be selected from, but not limited to PEG400, PEG300, PEG100, PEG1000, PEG-Stearate, PEG40-Stearate, PEG-Laureate, lecithin, phosphatidyl cholines, PEG-oleate, PEG-glycerol, TWEENs® (plysorbates), SPANs® (sorbitan monooleate), polypropylene glycol, DMSO, ethanol, isopropanol, NMP, DMF, acetone, methylene chloride, sorbitols.

The steric stabilizing solution used as Phase II for the initial nanosuspension may be selected from, but not limited to aqueous solutions of methyl cellulose, PVP, PVA, HPMC, cellulose, PLURONIC F127® (polyoxyethylene-polyoxyproplene block copolymer), PLURONIC F68® (polyoxyethylene-polyoxyproplene block copolymer), Carbomer (acrylic acid homopolymer crosslinked with allyl sucrose or allyl pentaethritol), hydroxyethyl cellulose, hydroxypropyl cellulose, PEGs, lecithin, phosphatidyl cholines, polyquarternium-1, polylysine, polyarginine, polyhistidine, guar gums, xanthan gums, chitosans, alginates, hyaluronic acid, chondroitin sulfate, TWEEN 20®, TWEEN 80®, SPANs® (sorbitan monooleate), sorbitols, amino acids. In a preferred embodiment, the steric stabilizer is methyl cellulose of viscosity 15 cP. In another embodiment, the steric stabilizer in phase II is methyl cellulose of viscosity 4 cP. In another embodiment, the steric stabilizer is methyl cellulose of viscosity 50 cP. In another embodiment, the steric stabilizer is methyl cellulose of viscosity 4000 cP. In another embodiment, the steric stabilizer is methyl cellulose of viscosity 100,000 cP. The concentration of methyl cellulose is 0.10%-0.20%, 0.20%-0.40% and 0.40%-0.50%. In a preferred embodiment, the concentration of methyl cellulose in phase II is 0.20%. In another preferred embodiment, the concentration of methyl cellulose in phase II is 0.39%. In one embodiment, the steric stabilizer in phase II is CARBOMER 940® (acrylic acid homopolymer crosslinked with allyl sucrose or allyl pentaerythritol) in concentrations 0.1-1%, 1%-10%. In another embodiment, the steric stabilizer is phase II is carboxymethyl cellulose in concentrations between 0.1%-1% and 1%-10%. In another embodiment, the steric stabilizer in phase II is carboxymethyl cellulose in combination with CARBOMER 940 acrylic acid homopolymer crosslinked with allyl sucrose or allyl pentaerythritol). In another embodiment, the steric stabilizer in phase II is PVA in concentrations between 0.1%-1% and 1-10%. In another embodiment the steric stabilizer in phase II is PVP in concentrations between 0.1% and 10%.

The steric stabilizer can also be cationic. Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PM-MTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol) 2000] (sodium salt) (also known as DPPE-PEG(2000)-Amine Na), Poly(2-methacryloxyethyl trimethylammonium bromide), poloxamines such as TETRONIC 908® (copolymer of poly(ethylene oxide) (PEO) and poly(propylene oxide) (PPO), also known as POLOXAMINE 908® (copolymer of poly(ethylene oxide) (PEO) and poly(propylene oxide) (PPO)), lysozyme, long-chain polymers such as alginic acid and carregenan. Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$ dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl $(C_{12-18})$dimethylbenzyl ammonium chloride, N-alkyl $(C_{14-18})$dimethyl-benzyl ammonium chloride, N-tetradecylidmethylbenzyl ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts and dialkyldimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl $(C_{12-14})$ dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™, alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Components of Step 2: The components of Step 2 are selected so that the task of purifying the nanocrystals prepared in the previous step is accomplished. The purification process is tangential flow filtration (TFF), or normal flow filtration (NFF) to accomplish ultrafiltration, or diafiltration, or microfiltration. In another embodiment, step 2 is accomplished by centrifugation. The choice of the filter is dependent upon the size of the nanocrystals produced. The pore size of the filter can be 0.1 µm or 0.2 µm, or 0.5 µm, or 0.8 µm or 1 µm, or 10 µm, or 20 µm. If the size distribution of the nanoparticles peaks at 0.5 µm, the pore size of the PVDF filter will be 0.1 µm. Preferably the size of the nanoparticles peaks at 0.5 µm. In this step, the nanocrystal suspension is purified such the initial continuous step is replaced entirely by a new continuous phase. The new continuous phase is selected such that, the drug has minimal solubility in it. This minimizes or eliminates Oswald Ripening.

The components of the purification process may be selected from, but not limited to the group containing aqueous solutions of HPMC, MC, carbomers, celluloses, PEGs, chitosans, alginates, PVP, F127, F68, hyaluronic acid, polyacrylic acid.

The components of Step 2 may have tissue-adhesive components that will enhance the residence time of the nanocrystals at the site, to subsequently prolong the effectiveness of the therapy. Tissue-adhesive components may be cationic or anionic. Cationic tissue-adhesive molecules are polyquad-1, polyethyleneimine, PAMAM dendrimer, PEI dendrimer, chitosan, alginate and derivatives, thereof.

The drug nanocrystals (optionally nanosuspensions) produced by the processes defined can be immunomodulators to treat inflammatory conditions of the eye. Immunomodulators have been proven effective in various inflammatory conditions resistant to steroids, or when chronic use of steroids is associated with steroids. Currently available agents act as cytotoxic agents to block lymphocyte proliferation or as immunomodulators to block synthesis of lymphokines. Cyclosporine A is a preferred immunomodulator that can be prepared using the process defined in this invention.

The drug nanosuspension can be a combination of two drugs that are formulated using the same process. Thus, it can be envisioned that both drugs are co-dissolved in common excipients, then precipitated using the techniques specified in this invention.

Hydrophobic Therapeutic Agents

The term "hydrophobic therapeutic agent" or "hydrophobic drug" used herein refers to therapeutic agents that are poorly soluble in water, e.g., having a water solubility less than about 10 mg/mL (e.g., less than 1 mg/mL, less than 0.1 mg/mL, or less than 0.01 mg/mL).

The methods of the invention can be applied to produce nanocrystals and/or new morphic forms of a hydrophobic drug. Examples of hydrophobic drugs include, but are not limited to, ROCK inhibitors, SYK-specific inhibitors, JAK-specific inhibitors, SYK/JAK or Multi-Kinase inhibitors, MTORs, STAT3 inhibitors, VEGFR/PDGFR inhibitors, c-Met inhibitors, ALK inhibitors, mTOR inhibitors, PI3Kδ inhibitors, PI3K/mTOR inhibitors, p38/MAPK inhibitors, NSAIDs, steroids, antibiotics, antivirals, antifungals, antiparsitic agents, blood pressure lowering agents, cancer drugs or anti-neoplastic agents, immunomodulatory drugs (e.g., immunosuppressants), psychiatric medications, dermatologic drugs, lipid lowering agents, anti-depressants, anti-diabetics, anti-epileptics, anti-gout agents, anti-hypertensive agents, anti-malarials, anti-migraine agents, anti-muscarinic agents, anti-thyroid agents, anxiolytic, sedatives, hypnotics, neuroleptics, β-blockers, cardiac inotropic agents, corticosteroids, diuretics, antiparkinsonian agents, gastro-intestinal agents, histamine H-receptor antagonists, lipid regulating agents, nitrates and other antianginal agents, nutritional agents, opioid analgesics, sex hormones, and stimulants.

The hydrophobic drugs suitable for the methods of the invention can be steroids. Steroids include for example, fluticasone, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone, fluocinolone acetonide, flunisolide, fluorometholone, clobetasol propionate, loteprednol, medrysone, rimexolone, difluprednate, halcinonide, beclomethasone, betamethasone, betamethasone sodium phosphate, Ciclesonide, dexamethasone, dexamethasone sodium phosphate, dexamethasone acetate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, prednisolone acetate, prednisolone sodium phosphate, fluoromethalone, fluoromethalone acetate, loteprednol etabonate, and betamethasone phosphate, including the esters and pharmaceutically acceptable salts thereof.

The hydrophobic drugs suitable for the methods of the invention can be nonsteroidal anti-inflammatory drugs, for example, Bromfenac, Diclofenac sodium, Flurbiprofen, Ketorolac tromethamine, mapracorat, naproxen, oxaprozin, ibuprofen, and nepafenac, including the esters and pharmaceutically acceptable salts thereof.

Other hydrophobic drugs suitable for the methods of the invention include besifloxacin, DE-110 (Santen Inc.), Rebamipide, Androgens (DHEA, testosterone, analogs, & derivatives having poor water solubility), estrogens (poorly water soluble compounds that are derivatives of estradiol, estriol, and estrone; e.g., estradiol, levonorgesterol, analogs, isomers or derivatives thereof), progesterone and progestins ($1^{st}$ through $4^{th}$ generation) with poor water solubility (e.g., norethindrone, analogs, and derivatives thereof, medroxyprogesterone, or tagaproget), and pregnenolone. Examples of progestins in various generations include: first generation (estrane) such as norethindrone, norethynodrel, norethindrone acetate, and ethynodiol diacetate; second generation (gonane) such as levonorgestrel, norethisterone, and norgestrel; third generation (gonane) such as desogestrel, gestodene, norgestimate, and drospirenone; and fourth generation such as dienogest, drospirenone, nestorone, nomegestrol acetate and trimegestone.

Other examples of hydrophobic drugs include, e.g., 10-alkoxy-9-nitrocamptothecin, 17b-Estradiol, 3'-azido-3'-deoxythymidine palmitate, 5-Amino levulinic acid, ABT-963, Aceclofenac, Aclacinomycin A, Albendazole, Alkannin/shikonin, All-trans retinoic acid (ATRA), alpha-Tocopheryl acetate, AMG 517, amprenavir, Aprepitant, Artemisinin, Azadirachtin, Baicalein, Benzimidazole derivatives, Benzoporphyrin, Benzopyrimidine derivatives, Bicalutamide, BMS-232632, BMS-488043, Bromazepam, Bropirimine, Cabamezapine, Candesartan cilexetil, Carbamazepine, Carbendazim, Carvedilol, Cefditoren, Cefotiam, Cefpodoxime proxetil, Cefuroxime axetil, Celecoxib, Ceramide, Cilostazol, Clobetasol propionate, Clotrimazole, Coenzyme Q10, Curcumin, Cycicoporine, Danazol, Dapsone, Dexibuprofen, Diazepam, Dipyridamole, docetaxel, Doxorubicin, Doxorubicin, Econazole, ER-34122, Esomeprazole, Etoricoxib, Etravirine, Everolimus, Exemestane, Felodipine, Fenofibrate, flurbiprofen, Flutamide, Furosemide, gamma-oryzanol, Glibenclamide, Gliclazide, Gonadorelin, Griseofulvin, Hesperetin, HO-221, Indomethacin, Insulin, Isoniazid, Isotretinoin, Itraconazole, Ketoprofen, LAB687, Limaprost, Liponavir, Loperamide, Mebendazole, Megestrol, Meloxicam, MFB-1041, Mifepristone, MK-0869, MTP-PE, Nabilone, Naringenin, Nicotine, Nilvadipine, Nimesulide, Nimodipine, Nitrendipine, Nitroglycerin, NNC-25-0926, Nobiletin, Octafluoropropane, Oridonin, Oxazepam, Oxcarbazepine, Oxybenzone, Paclitaxel, Paliperidone palmitate, Penciclovir, PG301029, PGE2, Phenytoin, Piroxicam, Podophyllotoxin, Porcine pancreatic lipase and colipase, Probucol, Pyrazinamide, Quercetin, Raloxifene, Resveratrol, Rhein, Rifampicin, Ritonavir, Rosuvastatin, Saquinavir, Silymarin, Sirolimus, Spironolactone, Stavudine, Sulfisoxazole, Tacrolimus, Tadalafil, Tanshinone, Tea polyphenol, Theophylline, Tiaprofenic acid, Tipranavir, Tolbutamide, Tolterodine tartrate, Tranilast, Tretinoin, Triamcinolone acetonide, Triptolide, Troglitazone, Valacyclovir, Verapamil, Vincristine, Vinorelbin-bitartrate, Vinpocetine, Vitamin-E, Warfarin, and XK469. More examples include, e.g., amphotericin B, gentamicin and other aminoglycoside antibiotics, ceftriaxone and other cephalosporins, tetracyclines, cyclosporin A, aloxiprin, auranofin, azapropazone, benorylate, diflunisal, etodolac, fenbufen, fenoprofen calcium, meclofenamic acid, mefanamic acid, nabumetone, oxyphenbutazone, phenylbutazone, sulindac, benznidazole, clioquinol, decoquinate, diiodohydroxyquinoline, diloxanide furoate, dinitolmide, furzolidone, metronidazole, nimorazole, nitrofurazone, ornidazole, and tinidazole.

The hydrophobic drugs suitable for the methods of the invention can also be FDA-approved drugs with cLogP of five or more, such as those listed in the table below.

2-(4-hydroxy-3,5-diiodobenzyl)cyclohexanecarboxylic
3,3',4',5-tetrachlorosalicylanilide
4,6-bis(1-methylpentyl)resorcinol
4,6-dichloro-2-hexylresorcinol
Acitretin
Adapalene
Alpha-butyl-4-hydroxy-3,5-diiodohydrocinnamic acid
Alpha-carotene
Alpha-cyclohexyl-4-hydroxy-3,5-diiodohydrocinnamic acid
Vitamin E
Vitamin E acetate
Alverine, Alverine Citrate
Amiodarone
Astemizole
Atiprimod dihydrochloride
Atorvastatin, atorvastatin calcium
Benzestrol
Bepridil, bepridil hydrochloride
Beta-carotene
Bexarotene
Bithionol
Bitolterol, bitolterol mesylate
Bromthymol blue
Buclizine, buclizine hydrochloride
Bunamiodyl sodium
Butenafine, butenafine hydrochloride
Butoconazole, butoconazole nitrate
Calcifediol
Calcium oleate
Calcium stearate
Candesartan cilexetil
Captodiame, captodiame hydrochloride
Cetyl alcohol -continued Chaulmoogric acid
Chloramphenicol palmitate
Chlorophenothane
Chlorophyll, chlorophyll unk
Chlorotrianisene
Chlorprothixene
Cholecalciferol
Cholesterol
Choline iodide sebacate
Cinacalcet
Cinnarizine
Clindamycin palmitate, clindamycin palmitate hydrochloride
Clofazimine
Cloflucarban
Clomiphene, enclomiphene, zuclomiphene, clomiphene citrate
Clotrimazole
Colfosceril palmitate
Conivaptan
Cyverine hydrochloride, cyverine
Desoxycorticosterone trimethylacetate, desoxycorticosterone pivalate
Dextromethorphan polistirex
Dichlorodiphenylmethane
Diethylstilbestrol
Diethylstilbestrol dipalmitate
Diethylstilbestrol dipropionate
Dimestrol
Dimyristoyl lecithin,
Diphenoxylate, atropine sulfate, diphenoxylate hydrochloride
Dipipanone, dipipanone hydrochloride
Docosanol
Docusate sodium
Domine
Doxercalciferol
Dromostanolone propionate
Dronabinol
Dutasteride
Econazole, econazole nitrate
Vitamin D2, ergocalciferol
Ergosterol,
Estradiol benzoate
Estradiol cypionate
Estradioldipropionate, estradiol dipropionate
Estradiol valerate
Estramustine
Ethanolamine oleate
Ethopropazine, ethopropazine hydrochloride
Ethyl icosapentate, eicosapentaenoic acid ethyl ester, ethyl
Ethylamine oleate
Etretinate
Fenofibrate
Fenretinide
Flunarizine, flunarizine hydrochloride
Fluphenazine decanoate
Fluphenazine enanthate
Fosinopril, fosinopril sodium
Fulvestrant
Gamolenic acid, gammalinolenic acid
Glyceryl stearate, glyceryl monostearate
Gramicidin
Halofantrine, halofantrine hydrochloride
Haloperidol decanoate
Hexachlorophene
Hexestrol
Hexetidine
Humulus
Hydroxyprogesterone caproate
Hypericin
Implitapide
Indigosol
Indocyanine green Iocarmate meglumine
Iodipamide
Iodoalphionic acid
Iodoxamate meglumine
Iophendylate
Isobutylsalicyl cinnamate
Itraconazole
Levomethadone
Linoleic acid,
Lucanthone, lucanthone hydrochloride
Meclizine, meclizine hydrochloride
Meclofenamic acid, meclofenamate, meclofenamate sodium
Mefenamic acid
Menthyl salicylate
Mercuriclinoleate
Mercury oleate
Mestilbol 5 mg, mestilbol
Methixene, methixene hydrochloride
Mibefradil, mibefradil dihydrochloride
Miconazole
Mifepristone
Mitotane
Mometasone furoate
Monoxychlorosene
Montelukast, montelukast sodium
Motexafin gadolinium
Myristyl alcohol
Nabilone
Naftifine, naftifine hydrochloride
Nandrolone decanoate
Nandrolone phenpropionate
N-myristyl-3-hydroxybutylamine hydrochloride 1 mg, n myristyl 3
Nonoxynol 9, nonoxynol, nonoxynol 10, nonoxynol 15, nonoxynol 30,
Octicizer
Octyl methoxycinnamate
Oleic acid
Omega 3 acid ethyl esters
Orlistat
Oxiconazole, oxiconazole nitrate
Oxychlorosene
Pararosaniline pamoate
Penicillin v hydrabamine
Perflubron
Perhexiline, perhexiline maleate
Permethrin
Vitamin K, phytonadione
Pimecrolimus
Pimozide
Polyethylene,
Polyvinyl n-octadecyl carbamate
Porfimer, porfimer sodium
Posaconazole
Potassium oleate
Potassium ricinoleate
Potassium stearate
Prednimustine
Probucol
Progesterone caproate
Promethestrol dipropionate
Pyrrobutamine phosphate
Quazepam
Quinacrine, quinacrine hydrochloride
Quinestrol
Raloxifene, raloxifene hydrochloride
Ritonavir
Rose bengal, rose bengal sodium
Sertaconazole
Sertraline, sertraline hydrochloride
Sibutramine, sibutramine hydrochloride
Rapamycin, sirolimus, rapamune
Sitosterol, sitosterols
Sodium beta-(3,5-diiodo-4-hydroxyphenyl)atropate,
Sodium dodecylbenzenesulfonate ng, dodecylbenzenesulfonic acid
Sodium oleate
Tetradecylsulfate, sodium tetradecyl sulfate
Sorbitan-sesquioleate
Stearic acid
Sulconazole, sulconazole nitrate
Suramin, suramin hexasodium
Tacrolimus
Tamoxifen, tamoxifen citrate
Tannic acid
Tazarotene
Telithromycin
Telmisartan
Temoporfin
Temsirolimus, tezacitabine
Terbinafine
Terconazole
Terfenadine
Testosterone cypionate
Testosterone enanthate
Testosterone phenylacetate
Tetradecylamine lauryl sarcosinate
Thioridazine
Thymol iodide
Tioconazole
Tipranavir
Tiratricol
Tocopherols excipient
Tolnaftate
Tolterodine
Toremifene, toremifene citrate
Alitretinoin, isotretinoin, neovitamin a, retinoic acid, tretinoin, 9-cis-retinoic
Tribromsalan
Triolein I 125
Triparanol
Troglitazone
Tyloxapol
Tyropanoate, tyropanoate sodium
Ubidecarenone, coenzyme Q10
Verapamil, dexverapamil
Verteporfin
Vitamin A acetate
Vitamin A palmitate
Zafirlukast
Cetyl myristate
Cetyl myristoleate
Docosahexanoic acid, doconexent
Hemin
Lutein
Chlorophyll b from spinach
Gossypol
Imipramine pamoate
Iodipamide meglumine
Ondascora
Zinc stearate
Phenylbutazone, phenylbutazone isomer
Bryostatin-1
Dexanabinol
Dha-paclitaxel
Disaccharide tripeptide glycerol dipalmitoyl
Oxiconazole nitrate
Sarsasapogenin
Tetraiodothyroacetic acid
(NZ)-N-[10,13-dimethyl-17-(6-methylheptan-2-yl)-

The hydrophobic drugs suitable for the methods of the invention can also be FDA-approved drugs with ALogP of five or more, such as those listed in the table below.

| | |
|---|---|
| tocoretinate | bitolterol mesilate |
| indocyanin green, Daiichi | falecalcitriol |
| colfosceril palmitate | ioxaglic acid |
| octenidine | fesoterodine fumarate |
| gadofosveset trisodium | quazepam |

-continued probucol
talaporfin sodium
menatetrenone
miriplatin hydrate
thiamine-cobaltichlorophyllate
montelukast sodium
everolimus
everolimus eluting stent
dexamethasone linoleate
estramustine phosphate sodium zotarolimus Lipo-dexamethasone palmitate
temoporfin
artemether + lumefantrine
acetoxolone aluminium salt
pipotiazine palmitate
telmisartan
telmisartan + Hydrochlorothiazide (HCTZ)
telmisartan + amlodipine, BI
(S)-amlodipine + telmisartan
sirolimus
sirolimus, NanoCrystal
sirolimus, stent, Cordis-1
temsirolimus
docosanol
clofoctol
iodoxamate meglumine
AGP-103
itraconazole
itraconazole, Choongwae
itraconazole, Barrier
halofantrine
etiroxate
testosterone undecanoate
meglumine iotroxinate
teboroxime
tirilazad mesylate
fazadinium bromide
fospropofol disodium
amiodarone
amiodarone
fulvestrant
indometacin farnesil
melinamide
miltefosine
candesartan cilexetil
candesartan cilexetil + HCTZ
candesartan cilexetil + amlodipine
cytarabine ocfosfate
penfluridol
paliperidone palmitate
zuclopenthixol decanoate
prednisolone farnesil
atorvastatin calcium
atorvastatin calcium + amlodipine
atorvastatin strontium
atorvastatin + fenofibrate (micronized), Ethypharm
ASA + atorvastatin + ramipril + metoprolol ER
(S)-amlodipine + atorvastatin
prednimustine
fidaxomicin
terfenadine
orlistat
bexarotene
bexarotene, gel, Ligand
calcium carbonate + vitamin D3
alendronate sodium + vitamin D
omega-3-acid ethyl esters
pasireotide
ebastine
ebastine, oral dissolving
enocitabine
Malarex
pimecrolimus fosaprepitant dimeglumine
levocabastine
ciclesonide
mometasone furoate
revaprazan
mometasone furoate, nasal
mometasone furoate, DPI, Twisthaler
mometasone furoate + formoterol
mometasone furoate, Almirall
tiotropium bromide + formoterol fumarate + ciclesonide, Cipla
mometasone furoate, implant, Intersect ENT
clobetasone butyrate
isoconazole
miconazole + benzoyl peroxide
miconazole nitrate
miconazole
miconazole
miconazole, Barrier miconazole, buccal,
bilastine
dexamethasone cipecilate
etretinate
tibenzonium
mepitiostane
etravirine
synth conjugated estrogens, B
sulconazole
ormeloxifene
blonanserin
evening primrose oil
flutrimazole
gamma linolenic acid
SH-U-508
lofepramine
treprostinil sodium
rimexolone
treprostinil sodium, inhaled
dienogest + estradiol valerate
estradiol + levonorgestrel (patch)
xibornol
sodium prasterone sulfate, S—P
ethyl icosapentate, Amarin
bepridil
bifonazole
lonazolac calcium
amorolfine
terbinafine
amorolfine, nail, Kyorin
pitavastatin
perflexane
alprazolam
alprazolam
alprazolam
sertaconazole
telithromycin
zafirlukast
diclofenac once-daily diclofenac potassium diclofenac sodium, Diffucaps
diclofenac twice-daily
diclofenac
diclofenac, Applied-1
diclofenac
diclofenac
rifaximin
rifaximine cream
diclofenac sodium
diclofenac potassium
diclofenac sodium gel
diclofenac potassium, ophthalm
diclofenac potassium
diclofenac sodium
pimozide
nabiximols fosamprenavir calcium
clinofibrate
tolciclate
teprenone
dexamethasone sodium phosphate
adapalene
fenticonazole
ixabepilone
Epiduo
Efalex
brotizolam
eltrombopag olamine
bazedoxifene acetate
butenafine
Clodermin
chlorhexidine
chlorhexidine
estradiol valerate + norethisterone enanthate
cinacalcet hydrochloride
ethyl icosapentate
fexofenadine HCl
fexofenadine + pseudoephedrine
almitrine bismesilate
butoconazole
butoconazole
TBI-PAB
medroxyprogesterone, depot
medroxyprogesterone acetate LA
dutasteride
flunarizine
dutasteride + tamsulosin
liranaftate
nabilone
lidoflazine
ethanolamine oleate
lasofoxifene
maraviroc
tacrolimus
tacrolimus, modified-release
tacrolimus, topical
tacrolimus
Americaine
conivaptan hydrochloride posaconazole
etizolam
tipranavir
azulene sodium sulfonate
triazolam
triazolam
hydroxyprogesterone caproate, Hologic
mifamurtide
lopinavir + ritonavir
ritonavir
ritonavir, soft gel-2
meclofenamate sodium
alfacalcidol
egualen sodium
tamoxifen
tamoxifen
toremifene citrate
tamoxifen, oral liquid, Savient Efamol Marine
terconazole
fluvastatin
fluvastatin, extended release
losartan + HCTZ
losartan potassium
amlodipine + losartan
(S)-amlodipine + losartan
beclometasone dipropionate, 3M
beclometasone dipropionate, LA
clotrimazole
beclometasone dipropionate, Dai
beclometasone + formoterol
heme arginate
tolterodine dronabinol
dronedarone hydrochloride
sestamibi
acitretin
pramiverine
setastine
rilpivirine
mifepristone
seratrodast
azilsartan
mifepristone
atracurium besilate
cisatracurium besylate
eberconazole
astemizole + pseudoephedrine
iopromide
otilonium bromide
Piloplex porfimer sodium
benzbromarone
tamibarotene
eprosartan mesylate
riodoxol
eprosartan mesylate + HCTZ
ivermectin
naftifine
quinestrol
raloxifene hydrochloride
repaglinide
metformin + repaglinide
econazole nitrate
beraprost
beraprost sodium, SR
vinflunine
ethinylestradiol + norelgestromin
denaverine hydrochloride
aprepitant
fluocortin butyl
monosialoganglioside GM-1, Amar
monosialoganglioside GM1
irbesartan
irbesartan + HCTZ
amlodipine besilate + irbesartan, Dainippon
tolvaptan
promestriene
Epavir
ufenamate
aprindine
clobenoside
atazanavir sulfate proglumetacin
gemeprost
rifapentine
sofalcone
motretinide
verapamil
verapamil
verapamil, OROS
verapamil
verapamil
verapamil SR
trandolapril + verapamil
verapamil
verapamil hydrochloride
valsartan
valsartan + HCTZ
amlodipine + valsartan
enzalutamide
Sm153 lexidronam
lubiprostone
paricalcitol
paricalcitol, oral
amineptine
isopropyl unoprostone
loperamide
loperamide

| | |
|---|---|
| tolterodine, extended-release | promegestone |
| oxiconazole | sertraline hydrochloride |

Other drugs suitable for the methods of the invention include long acting bronchodilators (e.g., Salmeterol xinafoate and Formoterol), anti-inflammatory drugs (statins such as Atorvastatin, Simvastatin, Lovastatin, and Rosuvastatin), macrolide antibiotics (e.g., Azithromycin), antinauseants, drugs highly metabolized by first pass metabolism (e.g., imipramine, morphine, buprenorphine, propranolol, diazepam, and midazolam), protein therapeutics (e.g., ranibizumab, bevacizumab, Aflibercept), rilonacept, and those listed in the table below.

| Drug Name | Exemplary Indications | Exemplary Route/Dosage Form |
|---|---|---|
| Azoles<br>Ketoconazole<br>Itraconazole<br>Fluconazole<br>Posaconazole<br>Voriconazole<br>Isavuconazole<br>Miconazole<br>Terconazole<br>Butoconazole<br>Tioconazole<br>Allylamine<br>terbinafine | Seborrhea, Tinea, Tinea versicolor, Skin inflammation, Athlete's foot, Oral candidiasis, Histoplasmosis, Cushing's syndrome, Blastomycosis, Coccidioidomycosis, Paracoccidioidomycosis, Leishmaniasis, Chronic mucocutaneous candidiasis, Acanthamoeba keratitis, Vulvovaginal Candidiasis<br><br>Fluconazole, Itraconazole, Ketonazole have activity against yeast keratitis and endophthalmitis | Topical,<br>Ophthalmic formulation (e.g., ophthalmic antifungal formulation) |
| Echinocandins<br>Anidulafungin | Indicated against *Aspergillus* and *Candida* species, Anidulafungin approved for esophageal candidases | Oral,<br>Topical (e.g., for treating *candida* infections, especially for azole-resistant strains) |
| Haloprogin | Broad spectrum antifungal | |
| Tolnaftate | Broad spectrum antifungal | |
| Naftifine | Broad spectrum antifungal | |
| Butenafine | Broad spectrum antifungal | |
| Ciclopirox Olamine | Broad spectrum antifungal, e.g., *C. albicans, E. floccosum, M. Canis* | |
| Griseofulvin | Tinea capitis, ringworm, tinea pedis, nail fungus | Topical |
| Fluticasone<br>Desoximetasone<br>Calcipotriol | Psoriasis | Topical |
| Betamethasone dipropionate<br>Clobetasol propionate<br>Diflorasone diacetate<br>Halobetasol propionate<br>Amcinonide<br>Fluocinonide<br>Diflorasone diacetate<br>Halcinonide<br>Momentasone furoate<br>Hydrocortizone valerate<br>Desonide<br>Amcinonide<br>Fluocinolone acetonide | | Topical |
| Cyclosporin | Alopecia Areata (autoimmune disorder)<br>Atopic dermatitis<br>Psoriasis<br>Dry eye | Topical |
| Latanoprost, Bimatoprost, Travoprost, and other prostaglandins or analogs thereof | Androgenetic Alopecia (Hair growth)<br>Glaucoma | Topical |
| Minoxidil | Androgenetic Alopecia (Hair growth) | Topical |
| Tacrolimus | Psoriasis | Topical |
| Dapsone | Dermatitis herpetiformis and leprosy; dermatosis, pustular psoriasis | Oral and Topical |
| Clindamycin | Acne | Topical |
| Tretinoin | Acne, cutaneous Kaposi's Sarcoma | |

-continued

| Drug Name | Exemplary Indications | Exemplary Route/Dosage Form |
|---|---|---|
| Systemic retinoids Etretinate Bexarotene | acne, psoriasis, ichthyosis, Darier's disease, rosacea | Oral, or formulated for dermal |
| Acitretin | psoriasis | Oral and topical |
| Isotretinoin | Acne, Chemotherapy | Topical, Systemic |
| azelastine | Allergy | Nasal |
| Beclomethasone | Allergy | Nasal |
| Flunisolide | allergy | Nasal |
| Budesonide |  | Nasal |
| Imiquimod | Genital warts, actinic keratoses and certain types of skin cancer called superficial basal cell carcinoma. | Topical |
| Zanamivir |  | Inhalation |
| Camptothecin | chemotherapeutic | Oral |
| Erlotinib | chemotherapeutic |  |
| Lapatinib | chemotherapeutic |  |
| Sorafenib | chemotherapeutic | Oral, or ophthalmic formulation against ARMD, DR |
| Azithromycin | Conjunctivitis | Ophthalmic |
| Bacitracin | Conjunctivitis, Blepharitis, Keratitis, Corneal ulcers, |  |
| natamycin | antifungal approved for ophthalmic | Ophthalmic |
| Amphotericin B | Potential ophthalmic-yeast and fungal keratitis and endophthalmitis | Ophthalmic |
| Psoralens and UVA | Orally administered 8-methoxypsoralen + UV-A light therapy is a FDA-approved treatment for psoriasis and vitiligo. | Oral or topical formulation of psoralens + light therapy |
| Permethrin | Insect repellent, lice | Oral and topical |
| Finasteride | Androgenetic alopecia | Oral, Topical scalp therapy |

Additional examples of hydrophobic drugs can also be found in e.g., Biopharmaceutics Classification System (BCS) database by Therapeutic systems Research Laboratory, Inc., Ann Arbor, Mich.; M Linderberg, et al., "Classification of Orally Administered Drugs on the WHO Model List of Essential Medicines According to the Biopharmaceutics Classification System," Eur J Pharm & Biopharm, 58:265-278(2004); N A Kasim et al., "Molecular properties of WHO Essential Drugs & Provisional Biopharmaceutical Classification," Molec Pharm, 1(1):85-96 (2004); A Dahan & GL Amidon, "Provisional BCS Classification of the Leading Oral Drugs on the Global Market," in Burger's Medicinal Chemistry, Drug Discovery & Development, 2010; Elgart A, et al. Lipospheres and pro-nano lipospheres for delivery of poorly water soluble compounds. Chem. Phys. Lipids. 2012 May; 165(4):438-53; Parhi R, et al., Preparation and characterization of solid lipid nanoparticles-a review. Curr Drug Discov Technol. 2012 March; 9(1):2-16; Linn M, et al. SOLUPLUS® (polyvinyl caprolactam-polyvinyl acetate-polyethylene glycol graft co-polymer) as an effective absorption enhancer of poorly soluble drugs in vitro and in vivo. Eur J Pharm Sci. 2012 Feb. 14; 45(3):336-43; Salústio P J, et al. Advanced technologies for oral controlled release: cyclodextrins for oral controlled release. AAPS PharmSciTech. 2011 December; 12(4):1276-92. PMCID: PMC3225529; Kawabata Y, et al. Formulation design for poorly water-soluble drugs based on biopharmaceutics classification system: basic approaches and practical applications. Int J Pharm. 2011 Nov. 25; 420(1):1-10; van Hoogevest P, et al. Drug delivery strategies for poorly water-soluble drugs: the industrial perspective. Expert Opin Drug Deliv. 2011 November; 8(11):1481-500; Bikiaris D N. Solid dispersions, part I: recent evolutions and future opportunities in manufacturing methods for dissolution rate enhancement of poorly water-soluble drugs. Expert Opin Drug Deliv. 2011 November; 8(11):1501-19; Singh A, et al. Oral formulation strategies to improve solubility of poorly water-soluble drugs. Expert Opin Drug Deliv. 2011 October; 8(10):1361-78; Tran PH-L, et al. Controlled release systems containing solid dispersions: strategies and mechanisms. Pharm Res. 2011 October; 28(10):2353-78; Srinarong P, et al. Improved dissolution behavior of lipophilic drugs by solid dispersions: the production process as starting point for formulation considerations. Expert Opin Drug Deliv. 2011 September; 8(9):1121-40; Chen H, et al. Nanonization strategies for poorly water-soluble drugs. Drug Discov. Today. 2011 April; 16(7-8):354-60; Kleberg K, et al. Characterising the behaviour of poorly water soluble drugs in the intestine: application of biorelevant media for solubility, dissolution and transport studies. J. Pharm. Pharmacol. 2010 November; 62(11):1656-68; and He C-X, et al. Microemulsions as drug delivery systems to improve the solubility and the bioavailability of poorly water-soluble drugs. Expert Opin Drug Deliv. 2010 April; 7(4):445-60; the contents of each of which are incorporated herein by reference in their entireties.

The nanocrystals of the hydrophobic drugs produced by the methods are ideally suited for systemic or non-systemic treatment of disorders that the hydrophobic drugs are used for, such as inflammatory disorders, respiratory disorders, autoimmune diseases, cardiovascular diseases, and cancer. For example, the nanocrystals of the invention can be used for treating rheumatoid arthritis, Lupus (including, e.g., Lupus nephritis and Systemic Lupus Erythematosus), allergic asthma, Lymphoma (including e.g., Non-Hodgkin lymphoma and Chronic lymphocytic leukemia), Immune thrombocytopenic purpura, Psoriasis, Psoriatic arthritis, Dermatitis, Ankylosing spondylitis, Crohn's disease, Ulcerative colitis, Gout, Atopic dermatitis, Multiple sclerosis, Pemphigous (including Bullous pemphigoid), Autoimmune hemolytic anemia, Chronic inflammatory demyelinating polyneuropathy, Guillain-Barre syndrome, Wegener's granulomatosis, and/or Glomerulonephritis. The nanocrystals of the invention can also be used in the primary prevention of major adverse cardiac events in patients with coronary artery disease.

New Morphic Forms

One unexpected advantage of the methods of the invention is that the nanocrystals of the hydrophobic drugs produced via the methods have novel morphologies different from those of the commercially available stock material or known morphologies of the hydrophobic drugs. The novel morphologies can be more stable (e.g., thermally stable), having higher tap densities, and/or more crystalline.

In one aspect, this invention provides a novel morphic form of fluticasone propionate, i.e., Form A, which is characterized by an X-ray powder diffraction pattern including peaks at about 7.8, 15.7, 20.8, 23.7, 24.5, and 32.5 degrees 2θ.

For example, Form A is further characterized by an X-ray powder diffraction pattern including additional peaks at about 9.9, 13.0, 14.6, 16.0, 16.9, 18.1, and 34.3 degrees 2θ.

For example, Form A is characterized by an X-ray powder diffraction pattern including peaks listed in Table A below.

TABLE A

| 2theta (degree) | d value (Å) | Intensity counts (I) | I/I0 | % I |
|---|---|---|---|---|
| 7.778 | 11.3667 | 242 | 0.11 | 2.030712 |
| 9.933 | 8.9044 | 2170 | 1 | 18.20928 |
| 11.463 | 7.7191 | 82 | 0.04 | 0.688093 |
| 12.34 | 7.1724 | 111 | 0.05 | 0.931442 |
| 12.998 | 6.8107 | 214 | 0.1 | 1.795754 |
| 14.648 | 6.0471 | 1,059 | 0.49 | 8.886465 |
| 15.699 | 5.6447 | 1,987 | 0.92 | 16.67366 |
| 16.038 | 5.5262 | 385 | 0.18 | 3.230679 |
| 16.896 | 5.2473 | 985 | 0.45 | 8.265503 |
| 18.101 | 4.9007 | 353 | 0.16 | 2.962155 |
| 19.342 | 4.5889 | 121 | 0.06 | 1.015356 |
| 20.085 | 4.4209 | 266 | 0.12 | 2.232105 |
| 20.838 | 4.2627 | 645 | 0.3 | 5.412436 |
| 22.003 | 4.0396 | 259 | 0.12 | 2.173366 |
| 22.763 | 3.9064 | 146 | 0.07 | 1.225141 |
| 23.705 | 3.7532 | 594 | 0.27 | 4.984476 |
| 24.52 | 3.6304 | 996 | 0.46 | 8.357808 |
| 25.621 | 3.4768 | 129 | 0.06 | 1.082487 |
| 26.141 | 3.4088 | 122 | 0.06 | 1.023748 |
| 26.853 | 3.32 | 247 | 0.11 | 2.072669 |
| 32.462 | 2.758 | 342 | 0.16 | 2.86985 |
| 34.293 | 2.6149 | 267 | 0.12 | 2.240497 |
| 34.736 | 2.5825 | 195 | 0.09 | 1.636318 |

For example, Form A is characterized by nanocrystals having the morphology of a long plate or blade.

For example, Form A is substantially free of impurities.

For example, Form A has a purity of greater than 90%, greater than 92%, greater than 95%, greater than 96%, greater than 97%, greater than 98%, or greater than 99%.

For example, Form A has a tap density of 0.5786 g/cm$^3$. In contrast, the tap density of fluticasone propionate stock is 0.3278 g/cm$^3$.

For example, the heat of melting for Form A is significantly higher (54.21 J/g), indicating that the former is a more crystalline material, requiring more energy to break intermolecular bonds such as ionic and hydrogen bonds.

For example, Form A has a melting range of 10° C., also indicating a highly ordered microstructure. In contrast, fluticasone propionate stock material melts over a slight wider range (11.1° C.).

For example, Form A dissolves more slowly than the stock material or homogenized material. Form A reaches saturated solubility after 6 weeks of incubation in an aqueous medium while the stock material or homogenized material reaches saturated solubility within 2 weeks of incubation in an aqueous medium.

For example, Form A is characterized by a dissolution rate in an aqueous medium (e.g., water or an aqueous solution) of about 1 µg/g/day in water at room temperature.

For example, the unit cell structure of Form A is Monoclinic, P21, a=7.7116 Å, b=14.170 Å, c=11.306 Å, beta=98.285, volume 1222.6.

For example, Form A has a melting point of 299.5° C., as opposed to 297.3° C. for the stock material (polymorph 1).

For example, Form A is characterized by nanoplates with an average size of about 10-10000 nm, (e.g., 100-1000 nm or 300-600 nm).

For example, Form A is characterized by fluticasone propionate nanoplates with a narrow range of size distribution. For example, Form A is characterized by fluticasone propionate nanoplates with a size distribution of 50-100 nm, of 100-300 nm, of 300-600 nm, of 400-600 nm, of 400-800 nm, of 800-2000 nm, of 1000-2000 nm, of 1000-5000 nm, of 2000-5000 nm, of 2000-3000 nm, of 3000-5000 nm, or of 5000-10000 nm.

For example, the nanoplates each have a thickness between 5 nm and 200 nm (e.g., 10-150 nm or 30-100 nm).

For example, the nanoplates have the [001] crystallographic axis substantially normal to the surfaces that define the thickness of the nanoplates.

In another aspect, this invention provides a novel morphic form of triamcinolone acetonide, i.e., Form B, which is characterized by an X-ray powder diffraction pattern including peaks at about 11.9, 13.5, 14.6, 15.0, 16.0, 17.7, and 24.8 degrees 2θ.

For example, Form B is further characterized by an X-ray powder diffraction pattern including additional peaks at about 7.5, 12.4, 13.8, 17.2, 18.1, 19.9, 27.0 and 30.3 degrees 2θ.

For example, Form B is characterized by an X-ray powder diffraction pattern including peaks listed in Table B below.

TABLE B

| 2theta (degree) | d value (Å) | Intensity (cps) | Relative Intensity |
|---|---|---|---|
| 7.5265 | 11.73621 | 925.01 | 1.86 |
| 11.9231 | 8.89089 | 36615.41 | 73.8 |
| 12.3561 | 7.82749 | 3250.64 | 6.55 |
| 13.4675 | 7.09394 | 4914.03 | 9.9 |
| 13.8284 | 6.73828 | 1483.26 | 2.99 |
| 14.5734 | 6.07325 | 49613.49 | 100 |
| 15.0476 | 5.88291 | 17123.8 | 34.51 |
| 15.9576 | 5.54942 | 10066.26 | 20.29 |
| 17.2466 | 5.13746 | 9609.43 | 19.37 |
| 17.6737 | 5.01424 | 18104.74 | 36.49 |
| 18.0594 | 4.90802 | 9517.13 | 19.18 |
| 19.9414 | 4.44887 | 9426.99 | 19 |
| 20.3221 | 4.36638 | 2783.08 | 5.61 |
| 21.3275 | 4.16275 | 1140.83 | 2.3 |
| 22.6548 | 3.92178 | 1719.17 | 3.47 |

TABLE B-continued

| 2theta (degree) | d value (Å) | Intensity (cps) | Relative Intensity |
|---|---|---|---|
| 22.9528 | 3.87154 | 1148.04 | 2.31 |
| 23.5648 | 3.77235 | 388.92 | 0.78 |
| 24.7819 | 3.58977 | 15106.92 | 30.45 |
| 25.0765 | 3.54827 | 1873.17 | 3.78 |
| 25.6279 | 3.47315 | 1345.05 | 2.71 |
| 26.4662 | 3.36501 | 2669.5 | 5.38 |
| 27.0149 | 3.2979 | 6198.27 | 12.49 |
| 28.6085 | 3.11772 | 2865.29 | 5.78 |
| 28.8669 | 3.09039 | 190.73 | 0.38 |
| 29.3538 | 3.04023 | 1382.62 | 2.79 |
| 30.0926 | 2.96725 | 1987.77 | 4.01 |
| 30.3395 | 2.94367 | 4605.47 | 9.28 |
| 30.5632 | 2.92263 | 1072.11 | 2.16 |
| 31.0498 | 2.87793 | 1892.56 | 3.81 |
| 32.0078 | 2.79393 | 1593.63 | 3.21 |
| 32.2282 | 2.77533 | 1331.46 | 2.68 |
| 32.6746 | 2.73843 | 958.6 | 1.93 |
| 33.5827 | 2.66643 | 2812.44 | 5.67 |
| 33.7886 | 2.65064 | 1308.18 | 2.64 |
| 34.2731 | 2.61428 | 777.59 | 1.57 |
| 34.8978 | 2.5689 | 792.47 | 1.6 |
| 35.3332 | 2.53823 | 1252.96 | 2.53 |
| 35.7276 | 2.51111 | 517.17 | 1.04 |
| 36.3522 | 2.46939 | 317.67 | 0.64 |
| 36.5664 | 2.45541 | 1046.14 | 2.11 |
| 36.7679 | 2.44241 | 354.44 | 0.71 |
| 37.9856 | 2.36687 | 2169.29 | 4.37 |
| 38.5534 | 2.33331 | 175.82 | 0.35 |
| 39.3381 | 2.28855 | 1348.09 | 2.72 |
| 39.5372 | 2.27749 | 842.58 | 1.7 |
| 39.9377 | 2.25557 | 1022.85 | 2.06 |

For example, Form B is characterized by an X-ray powder diffraction pattern substantially similar to the profile in red in FIG. 39.

For example, Form B is substantially free of impurities.

For example, Form B has a purity of greater than 90%, greater than 92%, greater than 95%, greater than 96%, greater than 97%, greater than 98%, or greater than 99%.

Pharmaceutical Compositions

The invention also features pharmaceutical compositions comprising an effective amount of the hydrophobic drug nanocrystals described herein and a pharmaceutically acceptable carrier useful for the systemic or non-systemic treatment or alleviation of disorders that the hydrophobic drug is used for, e.g., inflammatory disorders such as ophthalmic disorders and dermatologic disorders, respiratory disorders such as asthma or COPD, or cancer such as lymphoma.

In one embodiment, the invention features novel topical pharmaceutical compositions comprising an effective amount of nanocrystals of a hydrophobic drug (e.g., fluticasone) and a pharmaceutically acceptable carrier useful for the treatment or alleviation of a sign or symptom and prevention of blepharitis and or meibomian gland dysfunction (MGD). An effective amount of the formulations of the invention may be used to decrease inflammation of the eyelid margin, thereby treating blepharitis and or MGD.

For example, the compositions described in the invention can be used for post-operative care after surgery. For example, the composition of the invention can be used to control of pain after surgery, control of inflammation after surgery, argon laser trabceuloplasty and photorefractive procedures. Furthermore, the compositions can be used to treat other ophthalmic disorders such as ophthalmic allergies, allergic conjunctivitis, cystoid macular edema or meibomian gland dysfunction.

Additionally, the composition described in the invention can be used for the systemic or non-systemic treatment or alleviation of a sign or symptom and prevention of dermatologic disorders such as atopic dermatitis, dermatologic lesion, eczema, psoriasis, or rash.

Signs and symptoms that are associated with blepharitis include for example, eyelid redness, eyelid swelling, eyelid discomfort, eyelid itching, flaking of eyelid skin, and ocular redness.

Signs and symptoms of abnormal meibomian secretions include but are not limited to increased meibomian secretion viscosity, opacity, color, as well as an increase in the time (refractory period) between gland secretions. Signs and symptoms of diseases associated with abnormal meibomian gland (e.g. MGD) secretions include but are not limited to dry eye, redness of the eyes, itching and/or irritation of the eyelid margins and edema, foreign body sensation, and matting of the lashes The active agent component improves treats, relieves, inhibits, prevents, or otherwise decreases the signs and symptoms of blepharitis and/or MGD. The compositions of the invention are comfortable upon application to the eye, eye lid, eye lashes, or eye lid margin of a subject, and may be used for relief of acute or chronic blepharitis and/or MGD, and are particularly suitable for both intermittent and long term use.

Also, the composition described in the invention can be used for the systemic or non-systemic treatment, alleviation of a sign or symptom and prevention of respiratory disorders (e.g., asthma or COPD), autoimmune diseases (e.g., lupus or psoriasis), and cancer (e.g., lymphoma).

Fluticasone including the esters and pharmaceutically acceptable salts thereof. Fluticasone propionate is the preferred pharmaceutically acceptable salt. Fluticasone propionate, also known as S-fluoromethyl-6-α-9-difluoro-11-β-hydroxy-16-α-methyl-3-oxoandrosta-1,4-diene-17-β-carbothioate, 17-propionate, is a synthetic, trifluorinated, corticosteroid having the chemical formula $C_{25}H_{31}F_3O_5S$. It is a white to off-white powder with a molecular weight of 500.6 g/mol. Fluticasone propionate is practically insoluble in water (0.14 μg/ml), freely soluble in dimethyl sulfoxide and dimethyl-formamide, and slightly soluble in methanol and 95% ethanol.

Pharmaceutical ophthalmic formulations typically contain an effective amount, e.g., about 0.0001% to about 10% wt/vol., preferably about 0.001% to about 5%, more preferably about 0.01% to about 3%, even more preferably about 0.01% to about 1% of an ophthalmic drug (e.g., fluticasone) suitable for short or long term use treating or preventing ophthalmic and dermatologic disorders. The amount of the ophthalmic drug (e.g., fluticasone) will vary with the particular formulation and indicated use.

Preferably, the effective amount of nanocrystals of a hydrophobic drug (e.g., fluticasone) present in the formulations should be sufficient to treat or prevent the inflammatory disorder, respiratory disorder or cancer.

In certain embodiments, the composition described herein is a slow-release composition. In other embodiments, the composition described herein is a fast-release composition. Without wishing to be bound by the theory, the drug release rate of the compositions of the invention can be controlled by selecting specific morphic form or size of the drug particles. For example, the composition can include fluticasone propionate only in the morphic form of Form A or can include a mixture of Form A and polymorph 1 and/or polymorph 2 of FP. As another example, the composition can include drug nanocrystals of different sizes and/or size dispersions, e.g., a combination of nanocrystals of 300-600 nm (i.e., D10-D90) and nanocrystals of about 800-900 nm (i.e., D10-D90).

The pharmaceutical compositions of the invention described can be administered alone or in combination with other therapies. For example, the pharmaceutical compositions of the invention described above may additionally comprise other active ingredients (optionally in the form of nanocrystals via the methods of this invention), including, but not limited to, and vasoconstrictors, antiallergenic agents, anesthetics, analgesics, dry eye agents (e.g. secretagogues, mucomimetics, polymers, lipids, antioxidants), etc., or be administered in conjunction (simultaneously or sequentially) with pharmaceutical compositions comprising other active ingredients, including, but not limited to, and vasoconstrictors, antiallergenic agents, anesthetics, analgesics, dry eye agents (e.g. secretagogues, mucomimetics, polymers, lipids, antioxidants), etc.

Formulations

The pharmaceutical compositions of the invention can be formulated in various dosage forms suitable for the systemic or non-systemic treatment or alleviation of disorders that the hydrophobic drug is used for, e.g., inflammatory disorders such as ophthalmic disorders and dermatologic disorders, respiratory disorders such as asthma, or cancer such as lymphoma. The compositions described herein can be formulated in forms suitable for the specific route of administration, e.g. topical, oral (including, e.g., oral inhalation), intranasal, enteral or parenteral (injected into the circulatory system).

In certain embodiments, the formulation described herein is a slow-release formulation. In other embodiments, the formulation described herein is a fast-release formulation.

In certain embodiments, the topical compositions according to the present invention are formulated as solutions, suspensions, ointments, emulsions, gels, eye drops, and other dosage forms suitable for topical ophthalmic and dermatologic administration. In other embodiments, the compositions according to the present invention are formulated as dry powers, aerosols, solutions, suspensions, ointments, emulsions, gels and other dosage forms suitable for intranasal or oral administration.

Preferably, the topical ophthalmic composition is prepared for the administration to the eye lid, eye lashes, eye lid margin, skin, or ocular surface. In addition, modifications such as sustained-releasing, stabilizing and easy-absorbing properties and the like may be further applied to such the preparations. These dosage forms are sterilized, for example, by filtration through a microorganism separating filter, heat sterilization or the like.

Aqueous solutions are generally preferred, based on ease of formulation, as well as a patient's ability to easily administer such compositions by means of applying the formulation to the eye lid, eye lashes and eye lid margin. Application may be performed with an applicator, such as the patient's finger, a WEK-CEL®, Q-TIP®, cotton swabs, polyurethane swabs, polyester swabs, 25-3318-U swabs, 25-3318-H swabs, 25-3317-U swabs, 25-803 2PD swabs, 25-806 1-PAR swabs, brushes (e.g., LATISSE® (bimatoprost ophthalmic solution) brushes) or other device capable of delivering the formulation to the eye lid, eye lashes or eye lid margin.

However, the compositions may also be suspensions, viscous or semi-viscous gels, or other types of solid or semisolid compositions. In one embodiment, the formulations (e.g., fluticasone formulations) of the invention are aqueous formulations. The aqueous formulations of the invention are typically more than 50%, preferably more than 75%, and most preferably more than 90% by weight water. In another embodiment, the formulations are lyophilized formulations.

In a particular embodiment, the formulations of the invention are formulated as a suspension. Such formulations generally have a particle size no greater than 800 nm. Additionally the suspension formulation of the invention may include suspending and dispersing agents to prevent agglomeration of the particles.

In certain embodiments, carrier is non-aqueous. The non-aqueous carrier comprises an oil, e.g., castor oil, olive oil, peanut oil, macadamia nut oil, walnut oil, almond oil, pumpkinseed oil, cottonseed oil, sesame oil, corn oil, soybean oil, avocado oil, palm oil, coconut oil, sunflower oil, safflower oil, flaxseed oil, grapeseed oil, canola oil, low viscosity silicone oil, light mineral oil, or any combination thereof.

In embodiments wherein the formulation is an ointment, a preferred ointment base used to prepare the ophthalmic ointment of the present invention may be one that has been used in conventional ophthalmic ointments. In particular, the base may be liquid paraffin, white petrolatum, purified lanolin, gelation hydrocarbon, polyethylene glycol, hydrophilic ointment base, white ointment base, absorptive ointment base, Macrogol (Trade Name) ointment base, simple ointment base, and the like. For example, without limitation, an ointment formulation of the invention contains fluticasone propionate, petrolatum and mineral oil.

In embodiments wherein the formulation is a gelement, a preferred gelement base used to prepare the ophthalmic ointment of the present invention may be one that has been used in conventional ophthalmic gelments such as GENTEAL GEL® (hypromellose 0.2%).

In embodiments wherein the formulation is a cream, a preferred cream base used to prepare the ophthalmic cream of the present invention may be one that has been used in conventional ophthalmic cream. For example, without limitation, a cream formulation of the invention contains fluticasone propionate, PEG 400, an oil and a surfactant.

The topical formulation may additionally require the presence of a solubilizer, in particular if the active or the inactive ingredients tends to form a suspension or an emulsion. A solubilizer suitable for an above concerned composition is for example selected from the group consisting of tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80 or mixtures of those compounds. A specific example of an especially preferred solubilizer is a reaction product of castor oil and ethylene oxide, for example the commercial products CREMOPHOR EL® (Polyoxyl 35 Hydrogenated Castor Oil) or CREMOPHOR RH40® (PEG-40 Hydrogenated Castor Oil). Reaction products of castor oil and ethylene oxide have proved to be particularly good solubilizers that are tolerated extremely well by the eye. Another preferred solubilizer is selected from tyloxapol and from a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient.

Other compounds may also be added to the formulations of the present invention to adjust (e.g., increase) the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

In another embodiment, the topical formulations of this invention do not include a preservative. Such formulations would be useful for patients, who wear contact lenses, or those who use several topical ophthalmic drops and/or those with an already compromised ocular surface (e.g. dry eye) wherein limiting exposure to a preservative may be more desirable.

Any of a variety of carriers may be used in the formulations of the present invention. The viscosity of the carrier ranges from about 1 cP to about 4,000,000 cP, about 1 cP to about 3,000,000, about 1 cP to about 2,000,000 cP, about 1 cP to about 1,000,000 cP, about 1 cP to about 500,000 cP, about 1 cP to about 400,000 cP, about 1 cP to about 300,000 cP, about 1 cP to about 200,000 cP, about 1 cP to about 100,000 cP, about 1 cP to about 50,000 cP, about 1 cP to about 40,000 cP, about 1 cP to about 30,000 cP, about 1 cP to about 20,000 cP, about 1 cP to about 10,000 cP, about 50 cP to about 10,000 cP, about 50 cP to about 5,000 cP, about 50 cP to about 2500 cP, about 50 cP to about 1,000 cP, about 50 cP to about 500 cP, about 50 cP to about 400 cP, about 50 cP to about 300 cP, about 50 cP to about 200 cP, about 50 cP to about 100 cP, about 10 cP to about 1000 cP, about 10 cP to about 900 cP, about 10 cP to about 800 cP, about 10 cP to about 700 cP, about 10 cP to about 600 cP, about 10 cP to about 500 cP, about 10 cP to about 400 cP, about 10 cP to about 300 cP, about 10 cP to about 200 cP, or about 10 cP to about 100 cP.

Viscosity may be measured at a temperature of 20° C.+/−1° C. using a BROOKFIELD® Cone and Plate Viscometer Model VDV-III Ultra+ with a CP40 or equivalent Spindle with a shear rate of approximately 22.50+/− approximately 10 (1/sec), or a BROOKFIELD® Viscometer Model LVDV-E with a SC4-18 or equivalent Spindle with a shear rate of approximately 26+/− approximately 10 (1/sec). Alternatively, viscosity may be measured at 25° C.+/−1° C. using a BROOKFIELD® Cone and Plate Viscometer Model VDV-III Ultra+ with a CP40 or equivalent Spindle with a shear rate of approximately 22.50+/− approximately 10 (1/sec), or a BROOKFIELD® Viscometer Model LVDV-E with a SC4-18 or equivalent Spindle with a shear rate of approximately 26+/− approximately 10 (1/sec).

Other compounds may also be added to the formulations of the present invention to adjust (e.g., increase) the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Crystals of the present invention (e.g., fluticasone propionate crystals) can be coated onto or impregnated into surgical or implantable devices. In some embodiments, coating or embedding crystals (e.g., fluticasone propionate crystals) into a surgical or implantable device extends the release time of the drug while providing highly localized drug delivery. An advantage of this mode of administration is that more accurate concentrations and few side effects can be achieved. In one embodiment, the implantable device is an ocular implantable device for drug delivery. In other embodiments, the implantable device is a reservoir implant implantable by surgical means. In another embodiment, the implantable device is biodegradable, e.g., biodegradable microparticles. In further embodiments, the implantable device is made of silicon, e.g., nano-structured porous silicon. Exemplary surgical devices include but are not limited to stents (e.g., self-expanding stents, balloon expandable coil stents, balloon expandable tubular stents and balloon expandable hybrid stents), angioplasty balloons, catheters (e.g., microcatheters, stent delivery catheters), shunts, access instruments, guide wires, graft systems, intravascular imaging devices, vascular closure devices, endoscopy accessories. For example, a device used in a method or composition of the invention is ISCIENCE® device, IVEENA® device, CLEARSIDE™ device, or OCUSERT® device. Coating onto a surgical device can be performed using standard methods known in the art, such as those referenced in US20070048433A1, the contents of which are incorporated herein by reference.

Excipients

In some embodiments, the formulations of the invention comprise one or more pharmaceutically acceptable excipients. The term excipient as used herein broadly refers to a biologically inactive substance used in combination with the active agents of the formulation. An excipient can be used, for example, as a solubilizing agent, a stabilizing agent, a surfactant, a demulcent, a viscosity agent, a diluent, an inert carrier, a preservative, a binder, a disintegrant, a coating agent, a flavoring agent, or a coloring agent. Preferably, at least one excipient is chosen to provide one or more beneficial physical properties to the formulation, such as increased stability and/or solubility of the active agent(s). A "pharmaceutically acceptable" excipient is one that has been approved by a state or federal regulatory agency for use in animals, and preferably for use in humans, or is listed in the U.S. Pharmacopia, the European Pharmacopia or another generally recognized pharmacopia for use in animals, and preferably for use in humans.

Examples of carriers that may be used in the formulations of the present invention include water, mixtures of water and water-miscible solvents, such as $C_1$- to $C_7$-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral CARBOPOL® (polyacrylic acid crosslinked with sucrose or ally pentaerythritol), or mixtures of those polymers. The concentration of the carrier is, typically, from 1 to 100000 times the concentration of the active ingredient.

Further examples of excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN® (polysorbate), PLURONICS® (ethylene oxide/propylene oxide block copolymer), or a polyethylene glycol (PEG) designated 200, 300, 400, or 600; a CARBOWAX® (polyethylene glycol) designated 1000, 1500, 4000, 6000, and 10000; carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

In a particular embodiment, the carrier is a polymeric, mucoadhesive vehicle. Examples of mucoadhesive vehicles suitable for use in the methods or formulations of the invention include but are not limited to aqueous polymeric suspensions comprising one or more polymeric suspending agents including without limitation dextrans, polyethylene glycol, polyvinylpyrolidone, polysaccharide gels, GELRITE® (Gellan Gum), cellulosic polymers, and carboxy-containing polymer systems. In a particular embodiment, the polymeric suspending agent comprises a crosslinked carboxy-containing polymer (e.g., polycarbophil). In another particular embodiment, the polymeric suspending agent comprises polyethylene glycol (PEG). Examples of cross-linked carboxy-containing polymer systems suitable for use in the topical stable ophthalmic formulations of the invention include but are not limited to NOVEON® AA-1 (polycarbophil), CARBOPOL® (polyacrylic acid crosslinked with sucrose or ally pentaerythritol), and/or DURASITE® (polycarbophil, edetate disodium, sodium chloride; INSITE VISION).

In other particular embodiments, the formulations of the invention comprise one or more excipients selected from among the following: a tear substitute, a tonicity enhancer, a preservative, a solubilizer, a viscosity enhancing agent, a demulcent, an emulsifier, a wetting agent, a sequestering agent, and a filler. The amount and type of excipient added is in accordance with the particular requirements of the formulation and is generally in the range of from about 0.0001% to 90% by weight.

Tear Substitutes

According to some embodiments, the formulations may include an artificial tear substitute. The term "tear substitute" or "wetting agent" refers to molecules or compositions which lubricate, "wet," approximate the consistency of endogenous tears, aid in natural tear build-up, or otherwise provide temporary relief of dry eye signs or symptoms and conditions upon ocular administration. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxymethyl cellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as CARBOMER® 934P (acrylic acid homopolymer crosslinked with allyl sucrose or allyl pentaerythritol), CARBOMER®941 (acrylic acid homopolymer crosslinked with allyl pentaerythritol), CARBOMER® 940 (acrylic acid homoplymer crosslinked with allyl pentaerythritol, and CARBOMER® 974P (acrylic acid homopolymer crosslinked with allyl sucrose or allyl pentaerythritol). Many such tear substitutes are commercially available, which include, but are not limited to cellulose esters such as BION TEARS® (Dextran 70 0.1%; hypromellose 2910 0.3%), CELLUVISC® (sodium; 2,3,4,5,6-pentahydroxyhexanal; acetate), GENTEAL® (hypromellose 0.2%), OCCUCOAT® (hydroxypropyl methylcellulose ophthalmic), REFRESH® (Carboxymethylcellulose Sodium (0.5%; Glycerin (0.9%)), SYSTANE® (2-[2-(hydroxymethoxy)ethoxy]ethanol; propane-1,2-diol), TEARGEN II® (providone), TEARS NATURALE® (Hypromellose 2910 0.3%; dextran 70 0.1%), TEARS NATURAL II® (Dextran 70 0.1%; Hypromellose 2910 0.3%), TEARS NATURALE FREE® (Dextran 70 0.1%; Hypromellose 2910 0.3%), and THERATEARS® (Sodium Carboxymethylcellulose); and polyvinyl alcohols such as AKWA TEARS® (polyvinylalcohol 0.14%, HYPOTEARS® (polyvinyl alcohol 1.0%; polyethylene glycol 400 1.0%), MOISTURE EYES® (Glycerin (0.3%); Propylene glycol (1.0%), MURINE LUBRICATING® (Polyvinyl Alcohol (0.5%), Povidone (0.6%)), and VISINE TEARS® (Glycerin 0.2%; Hypromellose 0.2%; Polyethylene glycol 400 1%), SOOTHE® (glycerinl propylene glycol). Tear substitutes may also be comprised of paraffins, such as the commercially available LACRI-LUBE® (mineral oil (42.5%); white petrolatum (56.8%)) ointments. Other commercially available ointments that are used as tear substitutes include LUBRIFRESH PM® (mineral oil (15%); petrolatum (83%), MOISTURE EYES PM® (mineral oil (20%; white petrolatum (80%)) and REFRESH PM® (mineral oil (42.5%); white petrolatum (57.3%)).

In one preferred embodiment of the invention, the tear substitute comprises hydroxypropylmethyl cellulose (Hypromellose or HPMC). According to some embodiments, the concentration of HPMC ranges from about 0.1% to about 2% w/v, or any specific value within said range. According to some embodiments, the concentration of HPMC ranges from about 0.5% to about 1.5% w/v, or any specific value within said range. According to some embodiments, the concentration of HPMC ranges from about 0.1% to about 1% w/v, or any specific value within said range. According to some embodiments, the concentration of HPMC ranges from about 0.6% to about 1% w/v, or any specific value within said range. In a preferred embodiments, the concentration of HPMC ranges from about 0.1% to about 1.0% w/v, or any specific value within said range (i.e., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

For example, without limitation, a tear substitute which comprises hydroxypropyl methyl cellulose is GENTEAL® (hypromellose 0.2%) lubricating eye drops. GENTEAL® (hypromellose 0.2%) (CIBAVISION®-NOVARTIS)® is a sterile lubricant eye drop containing hydroxypropylmethyl cellulose 3 mg/g and preserved with sodium perborate. Other examples of an HPMC-based tear are provided.

In another preferred embodiment, the tear substitute comprises carboxymethyl cellulose sodium. For example, without limitation, the tear substitute which comprises carboxymethyl cellulose sodium is REFRESH® Tears (Carboxymethylcellulose Sodium (0.5%); Glycerin (0.9%)). REFRESH® Tears (Carboxymethylcellulose Sodium (0.5%); Glycerin (0.9%)) is a lubricating formulation similar to normal tears, containing a, mild non-sensitizing preservative, stabilised oxychloro complex (PURITE® (sodium perborate)), that ultimately changes into components of natural tears when used.

In some embodiments, the tear substitute, or one or more components thereof is buffered to a pH 5.0 to 9.0, preferably pH 5.5 to 7.5, more preferably pH 6.0 to 7.0 (or any specific value within said ranges), with a suitable salt (e.g., phosphate salts). In some embodiments, the tear substitute further comprises one or more ingredients, including without limitation, glycerol, propyleneglycerol, glycine, sodium borate, magnesium chloride, and zinc chloride.

Salts, Buffers, and Preservatives

The formulations of the present invention may also contain pharmaceutically acceptable salts, buffering agents, or preservatives. Examples of such salts include those prepared from the following acids: hydrochloric, hydrobromic, sulfuric, nitric, phosphoric, maleic, acetic, salicylic, citric, boric, formic, malonic, succinic, and the like. Such salts can also be prepared as alkaline metal or alkaline earth salts, such as sodium, potassium or calcium salts. Examples of buffering agents include phosphate, citrate, acetate, and 2-(N-morpholino)ethanesulfonic acid (MES).

The formulations of the present invention may include a buffer system. As used in this application, the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. According to some embodiments, the buffering components are present from 0.05% to 2.5% (w/v) or from 0.1% to 1.5% (w/v).

Preferred buffers include borate buffers, phosphate buffers, calcium buffers, and combinations and mixtures thereof. Borate buffers include, for example, boric acid and its salts, for example, sodium borate or potassium borate. Borate buffers also include compounds such as potassium tetraborate or potassium metaborate that produce borate acid or its salt in solutions.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

A preferred buffer system is based upon boric acid/borate, a mono and/or dibasic phosphate salt/phosphoric acid or a combined boric/phosphate buffer system. For example a combined boric/phosphate buffer system can be formulated from a mixture of sodium borate and phosphoric acid, or the combination of sodium borate and the monobasic phosphate.

In a combined boric/phosphate buffer system, the solution comprises about 0.05 to 2.5% (w/v) of a phosphoric acid or its salt and 0.1 to 5.0% (w/v) of boric acid or its salt. The phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

Other known buffer compounds can optionally be added to the lens care compositions, for example, citrates, sodium bicarbonate, TRIS, and the like. Other ingredients in the solution, while having other functions, may also affect the buffer capacity. For example, EDTA, often used as a complexing agent, can have a noticeable effect on the buffer capacity of a solution.

According to some embodiments, the pH of the aqueous ophthalmic solution is at or near physiological pH. Preferably, the pH of the aqueous ophthalmic solution is between about 5.5 to about 8.0, or any specific value within said range. According to some embodiments, the pH of the aqueous ophthalmic solution is between about 6.5 to 7.5, or any specific value within said range (e.g., 6.5, 6.6, 6.7, 6.8, 6.9, 7.0, 7.1, 7.2, 7.3, 7.4, 7.5). According to some embodiments, the pH of the aqueous ophthalmic solution is about 7. The skilled artisan would recognize that the pH may be adjusted to a more optimal pH depending on the stability of the active ingredients included in the formulation. According to some embodiments, the pH is adjusted with base (e.g., 1N sodium hydroxide) or acid (e.g., 1N hydrochloric acid).

For the adjustment of the pH, preferably to a physiological pH, buffers may especially be useful. The pH of the present solutions should be maintained within the range of 5.5 to 8.0, more preferably about 6.0 to 7.5, more preferably about 6.5 to 7.0 (or any specific value within said ranges). Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred. Generally, buffers will be used in amounts ranging from about 0.05 to 2.5 percent by weight, and preferably, from 0.1 to 1.5 percent.

According to preferred embodiments, the formulations of the present invention do not contain a preservative. In certain embodiments, the ophthalmic formulations additionally comprise a preservative. A preservative may typically be selected from a quaternary ammonium compound such as benzalkonium chloride, benzoxonium chloride or the like. Benzalkonium chloride is better described as: N-benzyl-N— ($C_8$-$C_{18}$ alkyl)-N,N-dimethylammonium chloride. Further examples of preservatives include antioxidants such as vitamin A, vitamin E, vitamin C, retinyl palmitate, and selenium; the amino acids cysteine and methionine; citric acid and sodium citrate; and synthetic preservatives such as thimerosal, and alkyl parabens, including for example, methyl paraben and propyl paraben. Other preservatives include octadecyldimethylbenzyl ammonium chloride, hexamethonium chloride, benzethonium chloride, phenol, catechol, resorcinol, cyclohexanol, 3-pentanol, m-cresol, phenylmercuric nitrate, phenylmercuric acetate or phenylmercuric borate, sodium perborate, sodium chlorite, alcohols, such as chlorobutanol, butyl or benzyl alcohol or phenyl ethanol, guanidine derivatives, such as chlorohexidine or polyhexamethylene biguanide, sodium perborate, GERMAL® II (diazolidinyl urea), sorbic acid and stabilized oxychloro complexes (e.g., PURITE® (sodium perborate)). Preferred preservatives are quaternary ammonium compounds, in particular benzalkonium chloride or its derivative such as POLYQUAD® (polyquaternium-1 0.001%; (see U.S. Pat. No. 4,407,791), alkyl-mercury salts, parabens and stabilized oxychloro complexes (e.g., PURITE® (sodium perborate)). Where appropriate, a sufficient amount of preservative is added to the ophthalmic composition to ensure protection against secondary contaminations during use caused by bacteria and fungi.

In particular embodiments, the formulations of the invention comprise a preservative selected from among the following: benzalkonium chloride, 0.001% to 0.05%; benzethonium chloride, up to 0.02%; sorbic acid, 0.01% to 0.5%; polyhexamethylene biguanide, 0.1 ppm to 300 ppm; polyquaternium-1 (Omamer M)—0.1 ppm to 200 ppm; hypochlorite, perchlorite or chlorite compounds, 500 ppm or less, preferably between 10 and 200 ppm); stabilized hydrogen peroxide solutions, a hydrogen peroxide source resulting in a weight % hydrogen peroxide of 0.0001 to 0.1% along with a suitable stabilizer; alkyl esters of p-hydroxybenzoic acid and mixtures thereof, preferably methyl paraben and propyl paraben, at 0.01% to 0.5%; chlorhexidine, 0.005% to 0.01%; chlorobutanol, up to 0.5%; and stabilized oxychloro complex (PURITE® (Sodium perborate)) 0.001% to 0.5%.

In another embodiment, the ophthalmic formulations of this invention do not include a preservative. Such formulations would be useful for patients who wear contact lenses, or those who use several topical ophthalmic drops and/or those with an already compromised ocular surface (e.g. dry eye) wherein limiting exposure to a preservative may be more desirable.

Viscosity Enhancing Agents and Demulcents

In certain embodiments, viscosity enhancing agents may be added to the formulations of the invention. Examples of such agents include polysaccharides, such as hyaluronic acid and its salts, chondroitin sulfate and its salts, dextrans, various polymers of the cellulose family, vinyl polymers, and acrylic acid polymers.

A variety of viscosity enhancing agents are known in the art and include, but are not limited to: polyols such as, glycerol, glycerin, polyethylene glycol 300, polyethylene glycol 400, polysorbate 80, propylene glycol, and ethylene glycol, polyvinyl alcohol, povidone, and polyvinylpyrrolidone; cellulose derivatives such hydroxypropyl methyl cellulose (also known as hypromellose and HPMC), carboxymethyl cellulose sodium, hydroxypropyl cellulose, hydroxyethyl cellulose, and methyl cellulose; dextrans such as dextran 70; water soluble proteins such as gelatin; carbomers such as carbomer 934P, carbomer 941, carbomer 940 and carbomer 974P; and gums such as HP-guar, or combinations thereof. Other compounds may also be added to the formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. Combinations and mixtures of the above agents are also suitable.

According to some embodiments, the concentration of viscosity enhancing agent or combination of agents ranges from about 0.5% to about 2% w/v, or any specific value within said range. According to some embodiments, the concentration of viscosity enhancing agent or combination of agents ranges from about 0.5% to about 1.5% w/v, or any specific value within said range. According to some embodiments, the concentration of viscosity enhancing agent or combination of agents ranges from about 0.5% to about 1% w/v, or any specific value within said range. According to some embodiments, the concentration of viscosity enhancing agent or combination of agents ranges from about 0.6% to about 1% w/v, or any specific value within said range. According to some embodiments, the concentration of viscosity enhancing agent or combination of agents ranges from about 0.7% to about 0.9% w/v, or any specific value within said range (i.e., about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In certain embodiments, the formulations of the invention comprise ophthalmic demulcents and/or viscosity enhancing polymers selected from one or more of the following: cellulose derivatives such as carboxymethycellulose (0.01 to 5%) hydroxyethylcellulose (0.01% to 5%), hydroxypropyl methylcellulose or hypromellose (0.01% to 5%), and methylcelluose (0.02% to 5%); dextran 40/70 (0.01% to 1%); gelatin (0.01% to 0.1%); polyols such as glycerin (0.01% to 5%), polyethylene glycol 300 (0.02% to 5%), polyethylene glycol 400 (0.02% to 5%), polysorbate 80 (0.02% to 3%), propylene glycol (0.02% to 3%), polyvinyl alcohol (0.02% to 5%), and povidone (0.02% to 3%); hyaluronic acid (0.01% to 2%); and chondroitin sulfate (0.01% to 2%).

In one preferred embodiment of the invention, the viscosity enhancing component comprises hydroxypropyl methylcellulose (HYPROMIELLOSE® or HPMC). HPMC functions to provide the desired level of viscosity and to provide demulcent activity. According to some embodiments, the concentration of HPMC ranges from about 0% to about 2% w/v, or any specific value within said range. According to some embodiments, the concentration of HPMC ranges from about 0% to about 1.5% w/v, or any specific value within said range. According to some embodiments, the concentration of HPMC ranges from about 0% to about 0.5% w/v, or any specific value within said range.

In another preferred embodiment, the viscosity enhancing component comprises carboxymethyl cellulose sodium.

The viscosity of the ophthalmic formulations of the invention may be measured according to standard methods known in the art, such as use of a viscometer or rheometer. One of ordinary skill in the art will recognize that factors such as temperature and shear rate may effect viscosity measurement. In a particular embodiment, viscosity of the ophthalmic formulations of the invention is measured at 20° C.+/−1° C. using a BROOKFIELD® Cone and Plate Viscometer Model VDV-III ULTRA+ with a CP40 or equivalent Spindle with a shear rate of approximately apprx. 22.50+/−apprx 10 (1/sec), or a BROOKFIELD® Viscometer Model LVDV-E with a SC4-18 or equivalent Spindle with a shear rate of approximately 26+/−apprx 10 (1/sec)).

Tonicity Enhancers

Tonicity is adjusted if needed typically by tonicity enhancing agents. Such agents may, for example be of ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. The aqueous solutions of the present invention are typically adjusted with tonicity agents to approximate the osmotic pressure of normal lachrymal fluids which is equivalent to a 0.9% solution of sodium chloride or a 2.5% solution of glycerol. An osmolality of about 200 to 1000 mOsm/kg is preferred, more preferably 200 to 500 mOsm/kg, or any specific value within said ranges (e.g., 200 mOsm/kg, 210 mOsm/kg, 220 mOsm/kg, 230 mOsm/kg, 240 mOsm/kg, 250 mOsm/kg, 260 mOsm/kg, 270 mOsm/kg, 280 mOsm/kg, 290 mOsm/kg, 300 mOsm/kg, 310 mOsm/kg, 320 mOsm/kg, 330 mOsm/kg, 340 mOsm/kg, 350 mOsm/kg, 360 mOsm/kg, 370 mOsm/kg, 380 mOsm/kg, 390 mOsm/kg or 400 mOsm/kg). In a particular embodiment, the ophthalmic formulations of the invention are adjusted with tonicity agents to an osmolality of ranging from about 240 to 360 mOsm/kg (e.g., 300 mOsm/kg).

The formulations of the invention of the present invention may further comprise a tonicity agent or combination of tonicity agents. According to some embodiments, the formulations of the invention may include an effective amount of a tonicity adjusting component. Among the suitable tonicity adjusting components that can be used are those conventionally used in contact lens care products such as various inorganic salts. Polyols and polysaccharides can also be used to adjust tonicity. The amount of tonicity adjusting component is effective to provide an osmolality from 200 mOsmol/kg to 1000 mOsmol/kg, or any specific value within said range.

Preferably, the tonicity component comprises a physiologically balanced salt solution that mimics the mineral composition of tears. According to some embodiments, tonicity may adjusted by tonicity enhancing agents that include, for example, agents that are of the ionic and/or non-ionic type. Examples of ionic tonicity enhancers are alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose.

According to some embodiments, the tonicity component comprises two or more of NaCl, KCl, $ZnCl_2$, $CaCl_2$, and $MgCl_2$ in a ratio that provides an osmolality range as above. According to some embodiments, the osmolality range of the formulations of the present invention is about 100 to about 1000 mOsm/kg, preferably about 500 to about 1000 mOsm/kg. According to some embodiments, the tonicity component comprises three or more of NaCl, KCl, $ZnCl_2$, $CaCl_2$, and $MgCl_2$ in a ratio that provides an osmolality range of about 100 to about 1000 mOsm/kg, preferably about 500 to about 1000 mOsm/kg. According to some embodiments, the tonicity component comprises four or more of NaCl, KCl, $ZnCl_2$, $CaCl_2$, and $MgCl_2$ in a ratio that provides an osmolality range of about 100 to about 1000 mOsm/kg, preferably about 500 to about 1000 mOsm/kg. According to some embodiments, the tonicity component comprises NaCl, KCl, $ZnCl_2$, $CaCl_2$, and $MgCl_2$ in a ratio that provides an osmolality range of about 100 to about 1000 mOsm/kg, preferably about 500 to about 1000 mOsm/kg.

According to some embodiments, NaCl ranges from about 0.1 to about 1% w/v, preferably from about 0.2 to about 0.8% w/v, more preferably about 0.39% w/v. According to some embodiments, KCl ranges from about 0.02 to about 0.5% w/v, preferably about 0.05 to about 0.3% w/v, more preferably about 0.14% w/v. According to some embodiments, $CaCl_2$ ranges from about 0.0005 to about 0.1% w/v, preferably about 0.005 to about 0.08% w/v, more preferably about 0.06% w/v. According to some embodiments, $MgCl_2$ ranges from about 0.0005 to about 0.1% w/v, preferably about 0.005 to about 0.08% w/v, more preferably about 0.06% W/V. According to some embodiments, $ZnCl_2$ ranges from about 0.0005 to about 0.1% w/v, preferably about 0.005 to about 0.08% w/v, more preferably about 0.06% W/V.

According to some embodiments, the ophthalmic formulations of the present invention may be adjusted with tonicity agents to approximate the osmotic pressure of normal lachrymal fluids which is equivalent to a 0.9% solution of sodium chloride or a 2.5% solution of glycerol. An osmolality of about 225 to 400 mOsm/kg is preferred, more preferably 280 to 320 mOsm.

Solubilizing Agents

The topical formulation may additionally require the presence of a solubilizer, in particular if one or more of the ingredients tend to form a suspension or an emulsion. Suitable solubilizers include, for example, tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80 or mixtures of those compounds. In a preferred embodiment, the solubilizer is a reaction product of castor oil and ethylene oxide, for example the commercial products CREMOPHOR EL® (Polyoxyl 35 Hydrogenated Castor Oil) or CREMOPHOR RH40® (PEG-40 Hydrogenated Castor Oil). Reaction products of castor oil and ethylene oxide have proved to be particularly good solubilizers that are tolerated extremely well by the eye. In another embodiment, the solubilizer is tyloxapol or a cyclodextrin. The concentration used depends especially on the concentration of the active ingredient. The amount added is typically sufficient to solubilize the active ingredient. For example, the concentration of the solubilizer is from 0.1 to 5000 times the concentration of the active ingredient.

Demulcifing Agents

The demulcents used in the present invention are used in effective amounts (i.e. "demulcifing amounts") for providing a demulcifing effect, i.e. sufficient to lubricating mucous membrane surfaces and to relieve dryness and irritation. Examples of suitable demulcents may include polyvinyl pyrrolidone, polyvinyl alcohol, polyethylene glycol, and other components such as polyethylene oxide and polyacrylic acid, are specifically excluded. In still other embodiments, other or additional demulcents may be used in combination with glycerin and propylene glycol. For example, polyvinyl pyrrolidone, polyvinyl alcohol, may also be used.

The specific quantities of demulcents used in the present invention will vary depending upon the application; however, typically ranges of several demulcents are provided: glycerin: from about 0.2 to about 1.5%, but preferably about 1% (w/w); propylene glycol: from about 0.2 to about 1.5%, but preferably about 1% (w/w); cellulose derivative: from about 0.2 to about 3%, but preferably about 0.5% (w/w). If additional demulcents are used, they are typically used in quantities specified in the over-the-counter monograph, cited above. A preferred cellulose derivative is pharmaceutical grade hydroxypropyl methylcellulose (HPMC).

Stability

The formulations of the present invention provide for the chemical stability of the formulated hydrophobic drug (e.g., steroid) and other optional active agents of the formulation. "Stability" and "stable" in this context refers to the resistance of the hydrophobic drug (e.g., steroid) and other optional active agents to chemical degradation and physical changes such as settling or precipitation under given manufacturing, preparation, transportation and storage conditions. The "stable" formulations of the invention also preferably retain at least 90%, 95%, 98%, 99%, or 99.5% of a starting or reference amount under given manufacturing, preparation, transportation, and/or storage conditions. The amount of hydrophobic drug (e.g., steroid) and other optional active agents can be determined using any art-recognized method, for example, as UV-Vis spectrophotometry and high pressure liquid chromatography (HPLC).

In certain embodiments, the formulations are stable at temperatures ranging from about 20 to 30° C. for at least 1 week, at least 2 weeks, at least 3 weeks, at least 4 weeks, at least 5 weeks, at least 6 weeks, or at least 7 weeks. In other embodiments, the formulations are stable at temperatures ranging from about 20 to 30° C. for at least 1 month, at least 2 months, at least 3 months, at least 4 months, at least 5 months, at least 6 months, at least 7 months, at least 8 months, at least 9 months, at least 10 months, at least 11 months, or at least 12 months. In one embodiment, the formulation is stable for at least 3 months at 20-25° C.

In other embodiments, the formulations are stable at temperatures ranging from about 2 to 8° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 2 months at 2 to 8° C.

In other embodiments, the formulations are stable at temperatures of about −20° C. for at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months. In one embodiment, the formulation is stable for at least 6-12 months at −20° C.

In a particular embodiment, a hydrophobic drug formulation of the invention is stable at temperatures of about 20-30° C. at concentrations up to 0.10% for at least 3 months. In another embodiment, the formulation is stable at temperatures from about 2-8° C. at concentrations up to 0.10% for at least 6 months.

In some embodiments, the formulation is a sterile topical nanocrystal fluticasone propionate formulation containing a suspension of between 0.001%-5% FP nanocrystals of the invention (e.g., 0.01-1%, or about 0.25%, 0.1%, or 0.05%), and a pharmaceutically acceptable aqueous excipient.

In some embodiments, the formulation further contains about 0.002-0.01% (e.g. 50 ppm±15%) benzalkonium chloride (BKC).

In some embodiments, the formulation further contains one or more coating dispersants (e.g., Tyloxapol, polysorbate 80, and PEG stearate such as PEG40 stearate), one or more tissue wetting agents (e.g., glycerin), one or more polymeric stabilizers (e.g., methyl cellulose 4000 cP), one or more buffering agents (e.g., dibasic sodium phosphate $Na_2HPO_4$ and monobasic sodium phosphate $NaH_2PO_4$, and/or one or more tonicity adjusting agents (e.g., sodium chloride).

In one embodiment, the formulation includes between 0.01%-1% FP nanocrystals of the invention (e.g., about 0.25%, 0.1%, or 0.05%), benzalkonium chloride (e.g., 0.002-0.01% or about 0.005%), polysorbate 80 (e.g., 0.01-1%, or about 0.2%), PEG40 stearate (e.g., 0.01-1%, or about 0.2%), Glycerin (e.g., 0.1-10%, or about 1%), methyl cellulose 4000 cP (e.g., 0.05-5%, or 0.5%), sodium chloride (e.g., 0.05-5%, or 0.5%), dibasic sodium phosphate $Na_2HPO_4$ and monobasic sodium phosphate $NaH_2PO_4$, and water, and the formulation has a pH of about 6.8-7.2. In another embodiment, the formulation includes between 0.01%-1% FP nanocrystals of the invention (e.g., about 0.25%, 0.1%, or 0.05%), benzalkonium chloride (e.g., 0.002-0.01% or about 0.005%), Tyloxapol (e.g., 0.01-1%, or about 0.2%), Glycerin (e.g., 0.1-10%, or about 1%), methyl cellulose 4000 cP (e.g., 0.05-5%, or 0.5%), sodium chloride (e.g., 0.05-5%, or 0.5%), dibasic sodium phosphate $Na_2HPO_4$ and monobasic sodium phosphate $NaH_2PO_4$, and water, and the formulation has a pH of about 6.8-7.2.

In some embodiments, the formulation has a viscosity between 40-50 cP at 20° C. In some embodiments, the osmolality of the formulation is about 280-350 (e.g., about 285-305) mOsm/kg. In some embodiments, the pH of the formulation is about 6.8-7.2. In some embodiments, the formulation has a viscosity between 40-50 cP at 20° C.

In some embodiments, the FP nanocrystals in the formulation have a median size of 300-600 nm, a mean size of 500-700 nm, a D50 value of 300-600 nm, and/or a D90 value of less than 2 μm.

In some embodiments, the formulation is administered at a therapeutically effective amount for treating blepharitis, via e.g., an applicator (e.g., a brush such as LATISSE® (bimatoprost ophthalmic solution) brush or a swab such as 25-3317-U swab). In one embodiment, two drops (about 40 μL drop size) of the formulation are loaded onto an applicator (e.g., a brush or a swab) and then delivered to the subject in need thereof by, e.g., swiping the applicator against the lower eyelid (once or twice) and then the upper eyelid (once or twice), and if needed, the above steps are repeated for the other eye with a new applicator.

Methods of Use

The invention also provides the use of the formulations described herein for systemic or non-systemic treatment, prevention or alleviation of a symptom of a disorder the hydrophobic drug is used for, e.g., inflammatory disorders, respiratory disorders, autoimmune diseases or cancer.

In embodiments, depending on the mode of administration, fluticasone propionate can be used to treat, for example, respiratory related illnesses such as asthma, emphysema, respiratory distress syndrome, chronic obstructive pulmonary disease (COPD), chronic bronchitis, cystic fibrosis, acquired immune deficiency syndrome, including AIDS related pneumonia, seasonal or perennial rhinitis, seasonal or perennial allergic and nonallergic (vasomotor) rhinitis, or skin conditions treatable with topical corticosteroids. Like other topical corticosteroids, fluticasone propionate has anti-inflammatory, antipruritic, and vasoconstrictive properties.

When administered in an aerosol, fluticasone propionate acts locally in the lung; therefore, plasma levels do not predict therapeutic effect. Studies using oral dosing of labeled and unlabeled conventional fluticasone propionate have demonstrated that the oral systemic bioavailability of fluticasone propionate is negligible (<1%), primarily due to incomplete absorption and presystemic metabolism in the gut and liver.

The extent of percutaneous absorption of topical corticosteroids is determined by many factors, including the vehicle and the integrity of the epidermal barrier. Occlusive dressing enhances penetration. Topical corticosteroids can be absorbed from normal intact skin. Inflammation and/or other disease processes in the skin increase percutaneous absorption.

Routes of Delivery

In certain embodiments, the methods of treatment disclosed in the present invention include all local (non-systemic) routes of delivery to the ocular tissues and adnexa. This includes but is not limited to topical formulations such as eye drops, gels or ointments and any intraocular, intravitreal, subretinal, intracapsular, suprachoroidal, subtenon, subconjunctival, intracameral, intrapalpebral, cul-de-sac retrobulbar and peribulbar injections or implantable or surgical devices.

Fluticasone propionate has been obtained in a crystalline form, designated Form 1, by dissolving the crude product (obtained, e.g. as described in British Patent No. 2088877) in ethyl acetate and then recrystallizing. Standard spray-drying techniques have also been shown to lead only to the known Form 1 of fluticasone propionate. See U.S. Pat. No. 6,406,718 to Cooper et al. A second polymorphic form of fluticasone propionate, prepared using supercritical fluid technology is described in Cooper et al.

Cooper et al. describe a method for forming a particulate fluticasone propionate product comprising the co-introduction of a supercritical fluid and a vehicle containing at least fluticasone propionate in solution or suspension into a particle formation vessel, the temperature and pressure in which are controlled, such that dispersion and extraction of the vehicle occur substantially simultaneously by the action of the supercritical fluid. Chemicals described as being useful as supercritical fluids include carbon dioxide, nitrous oxide, sulphur hexafluoride, xenon, ethylene, chlorotrifluoromethane, ethane, and trifluoromethane. The supercritical fluid may optionally contain one or more modifiers, such as methanol, ethanol, ethyl acetate, acetone, acetonitrile or any mixture thereof. A supercritical fluid modifier (or co-solvent) is a chemical which, when-added to a supercritical fluid, changes the intrinsic properties of the supercritical fluid in or around the critical point. According to Cooper et al., the fluticasone propionate particles produced using supercritical fluids have a particle size range of 1 to 10 microns, preferably 1 to 5 microns.

There are several disadvantages associated with the fluticasone compositions of Cooper et al. First, particle sizes of less than 1 micron are desirable, as smaller particle sizes can be associated with a more rapid dissolution upon administration, and consequent faster onset of action as well as greater bioavailability. Moreover, very small fluticasone particles, i.e., less than about 150 nm in diameter, are desirable as such compositions can be sterile filtered. In addition, the fluticasone particles of Cooper et al. may comprise supercritical fluid residues, which are undesirable as they do not have pharmaceutical properties and they can potentially cause adverse reactions.

Fluticasone propionate is marketed in several different commercial forms. ADVAIR DISKUS® (GLAXOSMITHKLINE®, Research Triangle Park, N.C.) is an inhalation powder of a combination of microfine fluticasone propionate and salmeterol xinofoate, which is a highly selective beta$_2$-adrenergic bronchodilator. The dosage form is marketed in three doses of fluticasone propionate: 100 mcg, 250 mcg, and 500 mcg. Following administration of ADVAIR® DISKUS® to healthy subjects, peak plasma concentrations of fluticasone propionate were achieved in 1 to 2 hours. See Physicians' Desk Reference, 57$^{th}$ Edition, pp. 1433 (Thompson PDR, N.J. 2003). Upon administration of ADVAIR® DISKUS® 500/50 (containing 500 mcg fluticasone propionate and 50 mcg salmeterol xinofoate), fluticasone propionate powder 500 mcg and salmeterol powder 50 mcg given concurrently, or fluticasone propionate powder 500 mcg alone, mean peak steady-state plasma concentrations of fluticasone propionate averaged 57, 73, and 70 pg/mL, respectively. Id. Peak steady-state fluticasone propionate plasma concentration in adult patients (n=11) ranged from undetectable to 266 pg/mL after a 500-mcg twice-daily dose of fluticasone propionate inhalation powder using the DISKUS® device. The mean fluticasone propionate plasma concentration was 110 pg/mL. The systemic bioavailability of fluticasone propionate inhalation powder using the DISKUS® device in healthy volunteers averages 18%. ADVAIR DISKUS® is indicated for the long-term, twice-daily, maintenance treatment of asthma.

FLOVENT® DISKUS® (GLAXOSMITHKLINE®) is an oral inhalation powder of microfine fluticasone propionate (50 mcg, 100 mcg, and 250 mcg) in lactose. Under standardized in vitro test conditions, FLOVENT® DISKUS® delivers 47, 94, or 235 mcg of fluticasone propionate from FLOVENT® DISKUS® 50 mcg, 100 mcg, and 250 mcg, respectively. The systemic bioavailability of fluticasone propionate from the DISKUS® device in healthy adult volunteers averages about 18%. FLOVENT® DISKUS® is indicated for the maintenance treatment of asthma as prophylactic therapy, and for patients requiring oral corticosteroid therapy for asthma.

FLOVENT® ROTADISK® (GLAXOSMITHKLINE®) is an oral inhalation powder of microfine fluticasone propionate (50 mcg, 100 mcg, and 250 mcg) blended with lactose. Under standardized in vitro test conditions, FLOVENT® ROTADISK® delivers 44, 88, or 220 mcg of fluticasone propionate from FLOVENT® ROTADISK® 50 mcg, 100 mcg, or 250 mcg, respectively. Id. The systemic bioavailability of fluticasone propionate from the ROTADISK® device in healthy adult volunteers averages about 13.5%. Id. FLOVENT® ROTADISK® is indicated for the maintenance treatment of asthma as prophylactic therapy, and for patients requiring oral corticosteroid therapy for asthma.

FLOVENT® (GLAXOSMITHKLINE®) is an oral inhalation aerosol of a microcrystalline suspension of fluticasone propionate (44 mcg, 110 mcg, or 220 mcg) in a mixture of two chlorofluorocarbon propellants (trichlorofluoromethane and dichlorodifluoromethane) with lecithin. Each actuation of the inhaler delivers 50, 125, or 250 mcg of fluticasone propionate from the valve, and 44, 110, or 220 mcg, respectively, of fluticasone propionate from the actuator. The systemic bioavailability of fluticasone propionate inhalation aerosol in healthy volunteers averages about 30% of the dose delivered from the actuator. Peak plasma concentrations after an 880-mcg inhaled dose ranged from 0.1 to 1.0 ng/ml. Id. FLOVENT® is indicated for the maintenance treatment of asthma as prophylactic therapy.

FLONASE® (GLAXOSMITHKLINE®) is a nasal spray of an aqueous suspension of microfine fluticasone propionate (50 mcg/dose) administered by means of a metering, atomizing spray pump. The dosage form also contains microcrystalline cellulose, carboxymethylcellulose sodium, dextrose, 0.02% w/w benzalkonium chloride, polysorbate 80, and 0.25% w/w phenylethyl alcohol. Indirect calculations indicate that fluticasone propionate delivered by the intranasal route has an absolute bioavailability averaging less than 2%. After intranasal treatment of patients with allergic rhinitis for 3 weeks, fluticasone propionate plasma concentrations were above the level of detection (50 pg/mL) only when recommended doses were exceeded and then only in occasional samples at low plasma levels. Due to the low bioavailability by the intranasal route, the majority of the pharmacokinetic data was obtained via other routes of administration. Studies using oral dosing of radiolabeled drug have demonstrated that fluticasone propionate is highly extracted from plasma and absorption is low. Oral bioavailability is negligible, and the majority of the circulating radioactivity is due to an inactive metabolite. Studies comparing the effect of oral and nasal dosing demonstrate that the therapeutic effect of FLONASE® (fluticasone propionate (50 mcg/dose)) can be attributed to the topical effects of fluticasone propionate applied to the nasal mucosa. FLONASE® (fluticasone propionate (50 mcg/dose)) nasal spray is indicated for the management of the nasal symptoms of seasonal and perennial allergic and nonallergic rhinitis.

CUTIVATE® (GLAXOSMITHKLINE®) is a topical dermatological fluticasone propionate cream or ointment (0.05% and 0.005% concentration). The cream and ointment are a medium potency corticosteroid indicated for the relief of the inflammatory and pruritic manifestations of corticosteroid-responsive dermatoses. In a human study of 12 healthy males receiving 12.5 g of 0.05% fluticasone propionate cream twice daily for 3 weeks, plasma levels were generally below the level of quantification (0.05 ng/ml). In another study of 6 healthy males administered 25 g of 0.05% fluticasone propionate cream under occlusion for 5 days, plasma levels of fluticasone ranged from 0.07 to 0.39 ng/ml. In a study of 6 healthy volunteers applying 26 g of fluticasone propionate ointment 0.005% twice daily to the trunk and legs for up to 5 days under occlusion, plasma levels of fluticasone ranged from 0.08 to 0.22 ng/mL.

The invention features methods of treating, preventing or alleviating a symptom of an ocular disorder such as blepharitis and/or MGD in a subject comprising use of the novel formulations described above. For example, a method of treating or preventing the ocular disorder (e.g., blepharitis or MGD) may comprise administering to the eye, eye lid, eye lashes, or eye lid margin of a subject in need thereof a formulation comprising a of the novel formulations described above.

The invention further features methods of treating dermatologic disorders in a subject comprising use of the novel formulations described herein.

The invention further features methods of treating a respiratory disease (e.g., asthma or COPD), rhinitis, dermatitis, or esophagitis by administering to a subject in need thereof the formulations of described herein.

The invention also features methods of treating cancer (e.g., lymphoma) by administering to a subject in need thereof the formulations of described herein.

The invention also features methods of treating an autoimmune disease (e.g., lupus or psoriasis) by administering to a subject in need thereof the formulations of described herein.

The effective amount of active agent to include in a given formulation, and the efficacy of a formulation for treating, preventing or alleviating a symptom of the target disorder, e.g., blepharitis and/or MGD, may be assessed by one or more of the following: slit lamp evaluation, fluorescein staining, tear film breakup time, and evaluating meibomian gland secretions quality (by evaluating one or more of secretion viscosity, secretion color, gland alignment, vascularity pattern, vascularity redness, hyperkeratinization, posterior lid edge, lash, mucocutaneous junction, perigland redness, gland geometry and gland height).

The effective amount of active agent(s) in the formulation will depend on absorption, inactivation, and excretion rates of the drug as well as the delivery rate of the active agent(s) from the formulation. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of any compound of the present invention will vary depending on the symptoms, age and other physical characteristics of the patient, the nature and severity of the disorder to be treated or prevented, the degree of comfort desired, the route of administration, and the form of the supplement. Any of the subject formulations may be administered in a single dose or in divided doses. Dosages for the formulations of the present invention may be readily determined by techniques known to those of skill in the art or as taught herein. In embodiments, for treating blepharitis, about 1-100 µg (e.g., 10-100 µg) FP nanoparticles are administered to each eyelid. In one embodiment, two drops (with a total volume of about 80 µL) of a formulation containing FP nanocrystals (e.g., 0.01-1%, or about 0.25%, 0.1%, or about 0.05%) are applied to each eye. For example, the two drops of formulation are first loaded onto an applicator (e.g., a brush or a swab) and then delivered to the subject in need thereof by, e.g., swiping the applicator against the lower eyelid (once or twice) and then the upper eyelid (once or twice), and if needed, the above steps are repeated for the other eye with a new applicator.

An effective dose or amount, and any possible effects on the timing of administration of the formulation, may need to be identified for any particular formulation of the present invention. This may be accomplished by routine experiment as described herein. The effectiveness of any formulation and method of treatment or prevention may be assessed by administering the formulation and assessing the effect of the administration by measuring one or more indices associated with the efficacy of the composition and with the degree of comfort to the patient, as described herein, and comparing the post-treatment values of these indices to the values of the same indices prior to treatment or by comparing the post-treatment values of these indices to the values of the same indices using a different formulation.

The precise time of administration and amount of any particular formulation that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

The combined use of several active agents formulated into the compositions of the present invention may reduce the required dosage for any individual component because the onset and duration of effect of the different components may be complimentary. In such combined therapy, the different active agents may be delivered together or separately, and simultaneously or at different times within the day.

Packaging

The formulations of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is generally unnecessary. The formulations, if an ointment formulation, may be packaged as appropriate for an ointment, as is known to one of skill in the art.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and other publications by the Food and Drug Administration, and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing.")

The use of a single dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

While the formulations of this invention are preferably formulated as "ready for use" aqueous solutions, alternative formulations are contemplated within the scope of this invention. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water. Because of the self-preserving nature of the solution, sterile water is not required.

Ophthalmic ointments may be produced as follows: if necessary, antiseptics, surfactants, stabilizers, alcohols, esters or oils are blended with an ointment base such as liquid paraffin or white petrolatum placed in a mortar or a mixing machine for ointment to form a mixture. The ointment thus prepared is filled into a bottle or tube for ointment.

Kits

In still another embodiment, this invention provides kits for the packaging and/or storage and/or use of the formulations described herein, as well as kits for the practice of the methods described herein. Thus, for example, kits may comprise one or more containers containing one or more ophthalmic solutions, ointments suspensions or formulations, tablets, or capsules of this invention. The kits can be designed to facilitate one or more aspects of shipping, use, and storage.

The kits may also optionally include a topical applicator to facilitate administration of the formulations provided therein. In some aspects the formulations are pre-loaded in the topical applicator. Topical applicators include for example a swab or wand.

The kits may optionally include instructional materials containing directions (i.e., protocols) disclosing means of use of the formulations provided therein. The kits may also optionally include a topical applicator to facilitate administration of the formulations provided therein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to internet sites that provide such instructional materials.

All publications and patents mentioned herein are hereby incorporated by reference in their entirety as if each individual publication or patent was specifically and individually indicated to be incorporated by reference. In case of conflict, the present application, including any definitions herein, will control. All percentages and ratios used herein, unless otherwise indicated, are by weight. All averages used herein, unless otherwise indicated, are number averages. For example, the average sizes of nanocrystals described herein are number average sizes. Further, the molecular weights of polymers described herein, unless otherwise indicated, are number average molar mass of said polymer. As used herein, the ranges/distributions of particle size or thickness of the nanoparticles, except for the range of average sizes of nanoparticles, are the ranges defined by D10 and D90 values.

Definitions

The term "D10" or "D10 value" refers to the value where 10% of the population lies below this value. Similarly, "D90" or "D90 value" refers to the value where 90 percent of the population lies below the D90, and "D50" or "D50 value" refers to the value where 50 percent of the population lies below the D50.

The term "statistical mode" or "mode" refers to the value that appears most often in a set of data. It is not uncommon for a dataset to have more than one mode. A distribution with two modes is called bimodal. A distribution with three modes is called trimodal. The mode of a distribution with a continuous random variable is the maximum value of the function. As with discrete distributions, there may be more than one mode.

The term "median" or "statistical median" is the numerical value separating the higher half of a data sample, a population, or a probability distribution, from the lower half.

The term "abnormal meibomian gland secretion" refers to a meibomian gland secretion with increased viscosity, opacity, color and/or an increased time (refractory period) between gland secretions.

The term "aqueous" typically denotes an aqueous composition wherein the carrier is to an extent of >50%, more preferably >75% and in particular >90% by weight water.

The term "blepharitis" refers to a disorder comprising inflammation of the eyelid in which inflammation results in eyelid redness, eyelid swelling, eyelid discomfort, eyelid itching, flaking of eyelid skin, and ocular redness. Abnormal meibomian gland secretions plays a role and lid keratinization, lid margin rounding, obscuration of the grey line, increased lid margin transparency, and increased vascularity are observed. Although the terms meibomian gland dysfunction (MGD) and meibomianitis are commonly referred to as blepharitis by most investigators, it is important to note that these are distinct diseases associated with abnormal meibum (i.e., meibomian gland secretions) and that the terms are not interchangeable. Blepharitis may cause chronic meibomian gland dysfunction. MGD in turn will cause dry eye symptoms due to the poor quality if the meibum which serves as the outermost layer of the tear film and acts to retard tear evaporation.

The term "comfortable" as used herein refers to a sensation of physical well being or relief, in contrast to the physical sensation of pain, burning, stinging, itching, irritation, or other symptoms associated with physical discomfort.

The term "comfortable ophthalmic formulation" as used herein refers to an ophthalmic formulation which provides physical relief from signs or symptoms associated with lid margin inflammation and/or ocular discomfort, and only causes an acceptable level of pain, burning, stinging, itching, irritation, or other symptoms associated with ocular discomfort, when instilled in the eye.

The phrase "effective amount" is an art-recognized term, and refers to an amount of an agent that, when incorporated into a pharmaceutical composition of the present invention, produces some desired effect at a reasonable benefit/risk ratio applicable to any medical treatment. In certain embodiments, the term refers to that amount necessary or sufficient to eliminate, reduce or maintain (e.g., prevent the spread of) a symptom of eyelid margin irritation, or prevent or treat eyelid margin inflammation. The effective amount may vary depending on such factors as the disease or condition being treated, the particular composition being administered, or the severity of the disease or condition. One of skill in the art may empirically determine the effective amount of a particular agent without necessitating undue experimentation.

The phrase "pharmaceutically acceptable" is art-recognized and refers to compositions, polymers and other materials and/or salts thereof and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and refers to, for example, pharmaceutically acceptable materials, compositions or vehicles, such as a liquid (aqueous or non-aqueous) or solid filler, diluent, excipient, solvent or encapsulating material, involved in carrying or transporting any supplement or composition, or component thereof, from one organ, or portion of the body, to another organ, or portion of the body, or to deliver an agent to the surface of the eye. Each carrier must be "acceptable" in the sense of being compatible with the other ingredients of the composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils such as castor oil, olive oil, peanut oil, macadamia nut oil, walnut oil, almond oil, pumpkinseed oil, cottonseed oil, sesame oil, corn oil, soybean oil, avocado oil, palm oil, coconut oil, sunflower oil, safflower oil, flaxseed oil, grapeseed oil, canola oil, low viscosity silicone oil, light mineral oil, or any combination thereof; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) gums such as HP-guar; (22) polymers; and (23) other non-toxic compatible substances employed in pharmaceutical formulations.

The term "pharmaceutically acceptable salts" is art-recognized, and refers to relatively non-toxic, inorganic and organic acid addition salts of compositions of the present invention or any components thereof, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric acids; and the salts prepared from organic acids such as acetic, fuoric, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, and isethionic acids.

The term "topical" refers to a route of administration, i.e., administering a drug to body surfaces such as the skin, tissues, or mucous membranes of a subject in need thereof. For example, topical medications may be administered to the eye lid, eye lashes, eye lid margin, skin, or into the eye (e.g., ocular surface such as eye drops applied to the conjunctiva). Topical medications may also be inhalational, such as asthma medications, or medications applied to the surface of a tooth.

The term "intraocular" as used herein refers to anywhere within the globe of the eye.

The term "intravitreal" as used herein refers to inside the gel in the back of the eye. For example, a Lucentis injection is administered intravitreally.

The term "subretinal" as used herein refers to the area between the retina and choroid. For example, iScience device is administered subretinally.

The term "intracapsular" as used herein refers to within the lens capsule. For example, iVeena device is administered intracapsularly.

The term "suprachoroidal" as used herein refers to the area between the choroid and sclera. For example, Clearside device is administered suprachoroidally.

The term "subtenon" as used herein refers to the area posterior to the orbital septum, outside the sclera, below tenon's capsule. For example, triamcinolone injections are administered to the subtenon.

The term "subconjunctival" as used herein refers to the area between the conjunctiva and sclera. For example, Macusight rapamycin injection is administered to the subconjunctival area.

The term "intracameral" as used herein refers to "into a chamber" of the eye, for e.g., into the anterior or posterior chamber of the eye. For example, any injections during cataract surgery are administered to intracamerally.

The term "intrapalpebral" as used herein refers to into the eyelid. For example, Botox injections are administered intrapalpebrally.

The term "cul-de-sac" as used herein refers to the space between the eyelid and globe. For example, Ocusert device is administered to the cul-de-sac.

The term "retrobulbar" as used herein refers to behind the orbit of the eye. The term "peribulbar" as used herein refers to within the orbit or adjacent to the eye. For example, anesthetic block before eye surgery is administered to the retrobulbar or peribulbar space.

As used herein, a "subject in need thereof" is a subject having a disorder which the hydrophobic drug described herein is intended to be used for treating, e.g., inflammatory disorders, respiratory disorders, autoimmune diseases or cancer A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

The term "preventing," when used in relation to a condition, such blepharitis, is art-recognized, and refers to administration of a composition which reduces the frequency of, or delays the onset of, signs and/or symptoms of a medical condition in a subject relative to a subject which does not receive the composition.

The term "treating" is an art-recognized term which refers to curing as well as ameliorating at least one symptom of any condition or disease.

EXAMPLES

Example 1

Preparation of 0.1% Fluticasone Propionate Nanoparticles

Methods: A HPLC Method to Determine the Concentration of Fluticasone Propionate was Developed, with the Details Provided in A.

The specific composition of Phase I depends upon the solubility of the drug in this phase. The solubility of fluticasone propionate in FDA-approved solvents and excipients was determined by dissolving 10 mg of drug in each solvent, vigorous vortexing and equilibrating overnight at 25 degrees centigrade. The suspension was centrifuged at 10,000 rpm and the supernatant analyzed by RP-HPLC at 239 nm. The solubility and compatibility of fluticasone propionate in each of the solvents was assessed.

A. HPLC Method Development

USP methods for the analysis of Fluticasone Propionate (cream, ointment) all utilize an extraction method with hexane, prior to dilution with the mobile phase, most likely due to the presence of excipients that can degrade or block the column, lower resolution on peak separation and loss in peak height. Extraction methods result in loss of degradation products, especially those that have not been previously characterized. It was deemed necessary to develop a method that would result in quantitation of the API, as well as degradation products that may arise due to potential incompatibilities with excipients.

Sample Preparation Method

1. A 400 µl sample (1 mg/ml drug suspension) was combined with 1.6 ml of mobile phase and vortex mixed. (Sample now 0.2 mg/ml)
2. 2 ml of sample was retrieved in a 5 ml syringe then filtered by hand pressure through a syringe MILLEX® GV filter (MILLIPORE®, 33 mm diameter, 0.22 um, DURAPORE® (PVDF), cat#: SLGV033RB, yellow). The effort needs a moderate amount of hand pressure.
3. The filtered sample was injected directly on the HPLC using the isocratic method.

Column Washing:

After several injections of samples that contained the formulation that were processed using the new dilution/filtration method, the column pressures did increase slightly from 222 bar to 230 bar. It was found that washing the column with mobile phase or a combination of methanol and 0.1M ammonium acetate solution at pH=7 was useful in reducing the column pressures to original pressures of about 222 bar. With the current column flow rate of 1.5 ml per minute and the long 250 mm column pressures are expected to be higher than similar method with lower flow rates and shorter column lengths. The HPLC has a cut off pressure of 400 bar. The monitoring the column pressures will be essential to determining when column washing is required so the HPLC method now records the pressures along with the scans. Also additional dilution injections, that do not contain the formulation, will be added more frequently to wash the column and prevent over pressurization, poor peak shape and loss of height.

Sample Set-up

A sequence to run multiple samples of the formulation should include blank injections to prevent an increase in column pressure. When the accuracy samples were run on the HPLC, 12 injections of vehicle were done where the pressure increased from 221 bar to 230 bar. These injections were then followed by 8 samples which did not contain any vehicle and the pressure dropped to 228 bar. Additional washing was done after the sequence to drop the pressure to a lower level. Based on these results a total of 6 to 8 injections of the formulation prepared as described should be followed by 2 to 4 injections of mobile phase. Additional column washing should be considered prior to another formulation sequence if needed.

Chromatography Conditions:

Instrument: AGILENT® 1200 HPLC with autosampler and DAD detector.

Mobile phase: Isocratic, 50% methanol, 35% 0.01M ammonium phosphate pH=3.5, 15% Acetonitrile.

Flow rate: 1.5 ml/min

Run time: 20 minutes

Column: PHENOMENEX LUNA® C18 5 micron 100A 250-4.6 mm P/N 00G-4041-EO

Column temperature: 40° C.

Sample tray: Room Temperature

Injection Volume: 50 micro liters

DAD detection: 239 nm

Sample setup: Blanks were run in the sequence between sets of experiments to ensure no carry over.

Standard Preparation: A 5 mg/ml standard stock solution of fluticasone was prepared by weighing up the solid and dissolving it in 100% acetonitrile. The dilution of this stock for the calibration curve samples were done in sample diluent. (50% acetonitrile/water)

Sample diluent: 50% acetonitrile/water.

Method Development Aspects

Specificity

Figure 1:
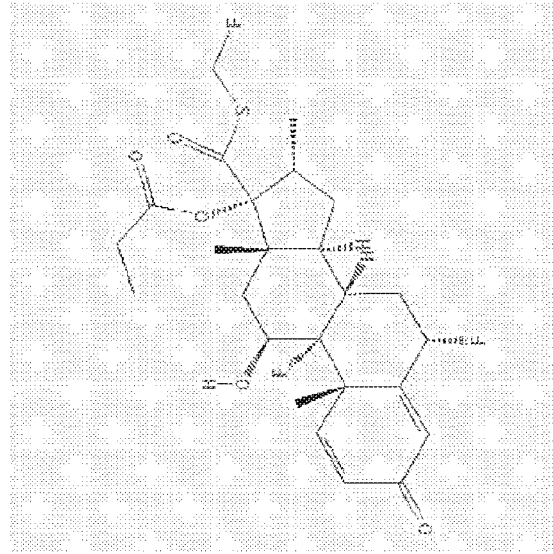
FIG. 1 is a summary of physical and chemical characteristics of fluticasone propionate.
Figure 2:
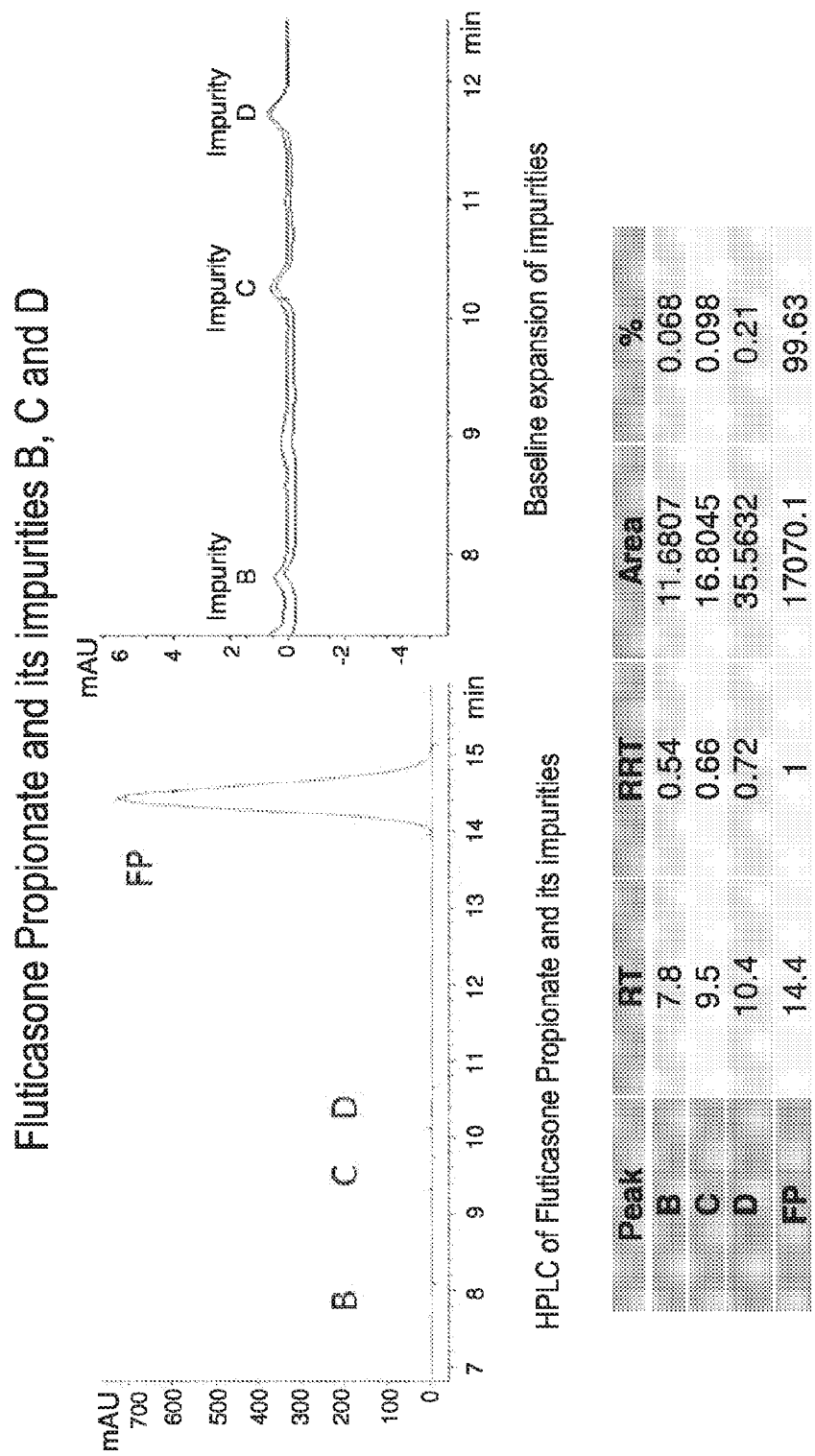
FIG. 2 is a HPLC chromatogram of fluticasone propionate and its common impurities.

The peak shape and height and retention times of FP and its impurities should be similar with the samples that contain vehicle or mobile phase as the diluent. Table 1 below shows the comparison of peak areas and heights for HPLC samples that contain vehicle or only mobile phase, shown in FIG. 2.

TABLE 1

| | FP Area and height Analysis. | | | |
|---|---|---|---|---|
| | Vehicle | | Diluent (MP) | |
| Sample | Area | Height | Area | Height |
| 0.153 mg/ml | 10672.1 | 531.6 | 10639.7 | 561 |
| 0.2044 mg/ml | 14180.7 | 710.3 | 14288.15 | 753.7 |
| 0.2555 mg/ml | 17864.6 | 894.45 | 17981.5 | 947.9 |

There is a very good match between the samples with and without the formulation vehicle. Table 2 shows the areas and heights of these samples.

TABLE 2

Heights and Areas with 50% ACN/Water
Diluent 50% Acetonitrile/Water

| Sample | Area | Height |
|---|---|---|
| 0.2112 mg/ml | 11096.5 | 578.2 |
| 0.1976 mg/ml | 14781.2 | 767.6 |
| 0.264 mg/ml | 18727.7 | 972.2 |

B, C and D Impurities:

The impurities B, C and D from the vehicle injections were also compared with the same impurities from the samples that did not contain the vehicle. Table 3 below shows equivalency between the two samples. The diluent is mobile phase.

TABLE 3

Impurities B, C and D

| | | Vehicle | | Diluent (MP) | |
|---|---|---|---|---|---|
| Sample | Impurity | Area | Height | Area | Height |
| 0.153 mg/ml | B | 5.5 | 0.41 | 3.3 | 0.28 |
| | C | 7.25 | 0.48 | 6.3 | 0.46 |
| | D | 7.35 | 0.5 | 7.2 | 0.49 |
| 0.2044 mg/ml | B | 4.2 | 0.4 | 4.4 | 0.37 |
| | C | 9.3 | 0.52 | 8.3 | 0.6 |
| | D | 10.1 | 0.685 | 9.5 | 0.64 |
| 0.2555 mg/ml | B | 4.9 | 0.49 | 5.9 | 0.48 |
| | C | 11.2 | 0.77 | 10.8 | 0.78 |
| | D | 13.3 | 0.93 | 11.9 | 0.8 |

Retention Times

The retention times of fluticasone propionate and impurities B, C and D are as follows:

TABLE 4

Retention Times of various sample preparations

| | Vehicle | | MP | | 50% ACN/water | |
|---|---|---|---|---|---|---|
| Sample | RT | RRT | RT | RRT | RT | RRT |
| FP | 14.1 | 1 | 14.2 | 1 | 13.8 | 1 |
| Imp B | 7.8 | 0.55 | 7.8 | 0.55 | 7.5 | 0.54 |
| Imp C | 10.3 | 0.73 | 10.3 | 0.73 | 9.9 | 0.72 |
| Imp D | 11.7 | 0.83 | 11.7 | 0.82 | 11.6 | 0.84 |

Linearity

The linearity of the new sample preparation was evaluated by spiking samples of the blank vehicle with a known amount of fluticasone propionate, dissolved in acetonitrile. Spikes of 300, 400 and 500 µl of a 5.11 mg/ml fluticasone propionate were dissolved into 2 grams of vehicle and diluted to 10 mls with mobile phase (MP). The mobile phase was: 50% methanol, 35% 0.01M ammonium phosphate at pH=3.5 and 15% acetonitrile. The results are shown below in Table 5. The units of the x-axis are mg/ml of FP. The method is considered linear if the correlation coefficient or $R^2$ value is 0.999 or greater.

TABLE 5

Linearity of fluticasone propionate in formulation vehicle

| File | Sample | | Area | Height | Concen | Area | Slope | Intercept |
|---|---|---|---|---|---|---|---|---|
| Feb16B02 | 1$^{st}$ inject | 0.153 | 10671 | 530.1 | 0.153 | 10672.1 | 70168.8628 | −96.3653395 |
| Feb16B03 | 2$^{nd}$ inject | | 10673.2 | 533.1 | 0.2044 | 14180.7 | | |
| Feb16B04 | 1$^{st}$ inject | 0.2044 | 14169.7 | 708.8 | 0.2555 | 17864.6 | | |
| Feb16B05 | 2$^{nd}$ inject | | 14191.7 | 712.4 | | | | |
| Feb16B06 | 1$^{st}$ inject | 0.2555 | 17870.3 | 893.3 | | | | |
| Feb16B07 | 2$^{nd}$ inject | | 17858.9 | 895.6 | | | | |

The same spikes were also done using 100% mobile phase. The linearity of these samples are shown below in Table 6. The x-axis in this case is mg/ml of fluticasone propionate.

TABLE 6

Linearity using mobile phase as diluent

| File | Sample | | Area | Height | Concern | Area | Slope | Intercept |
|---|---|---|---|---|---|---|---|---|
| Feb16B16 | 1$^{st}$ inject | 0.153 | 10637.5 | 560.2 | .0153 | 10639.65 | 71627 | −330.332 |
| Feb16B17 | 2$^{nd}$ inject | | 10641.8 | 561.8 | 0.2044 | 14288.15 | | |

TABLE 6-continued

Linearity using mobile phase as diluent

| File | Sample | Area | Height | Concern | Area | Slope | Intercept |
|---|---|---|---|---|---|---|---|
| Feb16B18 | 1$^{st}$ inject | 0.2044 | 14290.7 | 754.5 | 0.2555 | 17981.5 | |
| Feb16B19 | 2$^{nd}$ inject | | 14285.6 | 752.8 | | | |
| Feb16B20 | 1$^{st}$ inject | 0.2555 | 17980.4 | 947.6 | | | |
| Feb16B21 | 2$^{nd}$ inject | | 17982.6 | 948.2 | | | |

Chromatograms of the above samples from the same concentrations of vehicle and diluent samples were overlaid and show identical peak shapes and heights for fluticasone propionate and for impurities B, C and D.

Precision

Precision was evaluated by injecting a 0.2 mg/ml sample 10 times that was prepared from a sample of the suspension. The results are provided below in Table 7.

TABLE 7

Precision

| File | RT | Area | Height |
|---|---|---|---|
| Feb15B01 | 14.626 | 14017.6 | 650.2 |
| Feb15B02 | 14.631 | 14004.5 | 654.5 |
| Feb15C00 | 14.604 | 13975.8 | 655.5 |
| Feb15C01 | 14.588 | 13971.5 | 656.93 |
| Feb15C02 | 14.59 | 13962.4 | 658.2 |
| Feb15C03 | 14.579 | 13955 | 658.4 |
| Feb15C04 | 14.569 | 13941.7 | 660.3 |
| Feb15C05 | 14.566 | 13931.7 | 662 |
| Feb15C06 | 14.568 | 13935.4 | 665.4 |
| Feb15C07 | 14.559 | 13935.4 | 664.6 |
| Average | 14.6 | 13963.1 | 658.6 |
| Std Dev | 0.0 | 29.7 | 4.7 |
| RSD | 0.2 | 0.2 | 0.7 |

The target relative standard deviation (RSD) for a precision evaluation is ≤1.0%. All values were well within this range.

Accuracy

The accuracy of the method at 3 levels with the new sample preparation was evaluated by spiking a known amount of fluticasone propionate into about 2 grams of vehicle and comparing the calculated with the actual results. Table 8 below shows the recoveries using the calibration curve shown in Table 5.

TABLE 8

Spiked Samples

| Sample | Area | Av area | Calculated | Actual | Agreement |
|---|---|---|---|---|---|
| 360 | 12618.4 12616 | 12617.2 | 0.181 | 0.184 | 98.5 |
| 420 | 14803.7 14803.5 | 14803.6 | 0.212 | 0.215 | 98.9 |
| 480 | 17063 17056.6 | 17059.8 | 0.244 | 0.245 | 99.7 |

The acceptance criterion on this case is spike recovery of 99 to 101%. In this case there is good correlation between the actual and calculated values.

LOD and LLOQ

From the blank of this method the noise is approximately 0.1 absorbance units which is the same for the LOD and LLOQ calculations in Part A of this report. The LLOQ and the LOD should be 10× and 3× this height respectively. Since the peak heights are very similar with and without the vehicle present, the LOD and LLOQ were prepared to the same concentration ranges as Part A of this report however in this case the spike concentration were prepared in mobile phase, spiked into 2 grams of vehicle and diluted to 10 mls with mobile phase to the LOD and LLOQ concentrations. The samples were injected 2× and the averages are shown below. A sample of 511 ng/ml gave a reproducible area/height of 31.4/1.7. (LLOQ). For the LOD, a sample of 1 53.3 ng/ml gave an area/height of 8.1/0.44. The heights of both the LLOQ and LOD are approximately what was calculated based on the measured noise.

B. Solubility Determination of Fluticasone Propionate

The solubility of fluticasone propionate is given in Table 9. The specific composition of Phase I depends upon the solubility of the drug in this phase. The solubility of fluticasone propionate in FDA-approved solvents and excipients was determined by dissolving 10 mg of drug in each solvent, vigorous vortexing and equilibrating overnight at 25 degrees centigrade. The suspension was centrifuged at 10,000 rpm and the supernatant analyzed by RP-HPLC at 239 nm. The solubility and compatibility of fluticasone propionate in each of the solvents was assessed.

TABLE 9

Solubility of Fluticasone Propionate

| Solvent | Solubility (mg/ml) |
|---|---|
| Ethanol | 4.4462 |
| PEG 400 | 4.3310 |
| Glycerin | 0.1441 |
| Propylene glycol | 0.7635 |
| PHOSAL ® 50 PG (phosphatidylcholine concentrate with at least 50% phosphatitylcholine and propylene glycol) | 0.4261 |
| PHOSAL ® 53 MCT (phosphatidycholine concentrate with at least 53% phosphatitylcholine and ethylemethylketone) | 0.4000 |
| PHOSAL ® 50 PG (phosphatidycholine concentrate with at least 50% phosphatitylcholine and propylene glycol) | 0.6601 |
| Polysorbate 60 | 4.9099 |
| Polysorbate 80 | 4.6556 |
| Methylene Chloride | 9.2472 |
| Polysorbate 20 | 7.0573 |
| SPAN 80 ® (sorbitan monooleate) | 0.0521 |
| SPAN 20 ® (sorbitan monooleate) | 0.0469 |
| PPG | 2.2269 |
| n-octanol | 0.0873 |
| Corn oil | 0.0069 |
| Castor oil | 0.0180 |
| Mineral oil | 0.0000 |
| oleic acid | 0.0136 |
| PEG 200 | 4.2060 |
| Phos buff pH = 7 | 0.0095 |
| Acetone | 62.976 |

TABLE 9-continued

Solubility of Fluticasone Propionate

| Solvent | Solubility (mg/ml) |
|---|---|
| Dextrose 5% | 0.0053 |
| water | 0.00014 |

C. Nanocrystal Preparation by Anti-Solvent Crystallization During Sonication (1 Step Process)

Figure 3:
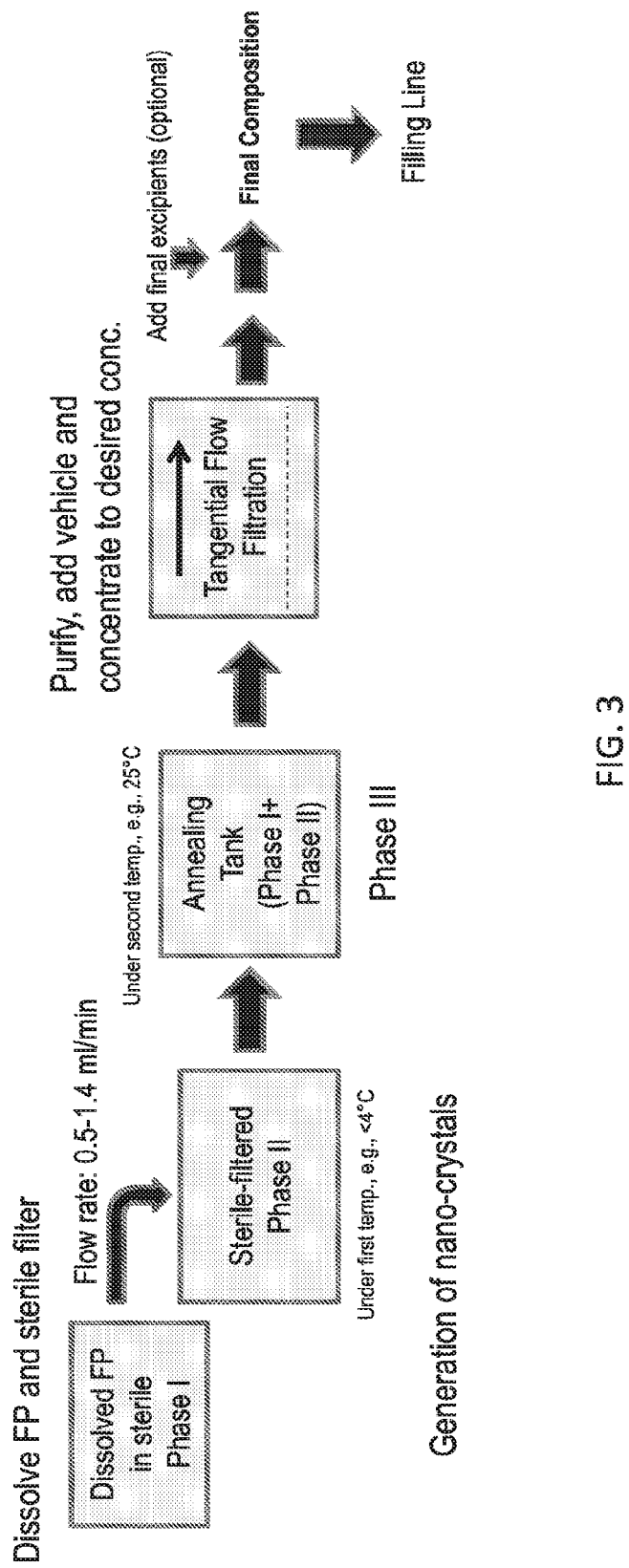
FIG. 3 is a scheme of an embodiment of the process of the invention (denoted as "batch process").

The process is as shown in FIG. 3, without the purification step. In the case of Fluticasone Propionate, the drug was dissolved in the following composition: Fluticasone Propionate (0.45%), TWEEN 80® (polysorbate 80) (7.44%), PEG 400 (23%), Polypropylene Glycol 400 (69.11%). This composition was Phase I. The solubility of Fluticasone Propionate was maximized in each of these solvents. Table 9 was utilized to arrive at the composition of Phase I. The final composition (after Phase I is added to Phase II) contained the drug at 0.1% w/w and the excipients at concentrations approved for ophthalmic medications.

Phase I and Phase II were both sterile filtered through 0.22 micron PVDF filters before mixing. In an experiment investigating the drug binding kinetics of fluticasone propionate in Phase I to the filter, it was found that there was little or no binding of FP with the PVDF filter.

Sterile Phase I was added drop-wise into a sterile continuous phase (Phase II solution) while sonicating. 4.3 g of Phase I was added drop-wise to 15.76 g of Phase II. Sonication was performed with a SONIC RUPTURE® 400 (OMNI INTERNATIONAL®, Inc.). The sonication conditions were as follows: (a) Tip size (12.7 mm), temperature 2-4° C., power output 10 W, duration: 1.5 minutes, batch size was 20 ml. This was accomplished using a 50 ml beaker. The rate at which phase I was added to phase II governs the particle size of the crystals formed. For the 20 ml batch, the rate at which phase I is added to phase II was 2.15 ml/min.

The specific composition of phase II is extremely nuanced, since the components of this phase act as the stabilizing phase for the droplets as the nanocrystals are being formed. The effectiveness of the stabilizer is dependent upon the molecular weight and chemical structure of the stabilizing polymer, its adherence to the drug surface and its ability to lower the surface energy of the nanocrystals. Additionally, the concentration of the polymer in the continuous phase appears to affect the particle size of the suspension. The function of the stabilizing phase is to also, prevent coalescence of the droplets prior to formation of the nanoparticles. For the preparation of 0.1% fluticasone propionate, the final composition of Phase II was 0.013% benzalkonium chloride, 0.25% methyl cellulose and 99.7% water. For fluticasone propionate, the suspension obtained at the end of Step 1 contains excipients at regulated amounts allowed in FDA approved ophthalmic medications. A 0.1% fluticasone propionate nanoparticle suspension contains 0.1% drug, 3.23% TWEEN 80® (polysorbate 80), 4.97% PEG400, 14.95% PPG 400, 0.010% benzalkonium chloride, 0.38% methyl cellulose and Q.S. purified water. The particle size range at this step is 400-800 nm. The pH was 5.8 and the osmolality was 546 mOsm/Kg.

For the treatment of blepharitis, a hyperosmolal solution may be tolerated, although an isotonic suspension is always desired, since the application is the interface of the eyelid and the ocular surface.

At a drug concentration of 0.06%, the vehicle composition is isotonic (316 mOsm/kg). At this drug concentration, the respective concentrations of excipients in the continuous phase are 2.57% TWEEN 80® (polysorbate 80), 2.99% PEG400, 8.97% PPG 400, 0.010% benzalkonium chloride and purified water (Q.S.). The pH of this solution is 6.5. NaOH may be added to adjust the pH to a neutral pH. This can be then diluted to lower concentrations of fluticasone propionate nanocrystals suspended in the vehicle. Table 10 shows formulations of fluticasone propionate prepared at concentrations 0.06% -0.001%.

TABLE 10

Concentrations 0-0.06% fluticasone propionate

| Concentration (% FP) | Concentration (mg/ml) FP | Vehicle | Osmolality (mOsm/kg) | pH | Particle size (microns) |
|---|---|---|---|---|---|
| 0.06 | 0.6 | PEG400 (2.99%), PPG400 (8.97%), TWEEN 80 ® (polysorbate 80) (2.57%), BAK (0.011%), MC (0.2%), water (QS), NaOH (pH adj.) | 316 | 7.01 | 1.09 |
| 0.01 | 0.1 | | 310 | 7.02 | 1.08 |
| 0.001 | 0.01 | | 305 | 7.01 | solution |
| 0 | 0 | | 306 | 7.00 | solution |

The solutions meet ophthalmic criteria of pH, excipient composition and osmolality. Formulations at concentrations greater than 0.06% have osmolality values>350 mOsm/kg. One of the issues with this formulation is "Ostwald Ripening", or growth of particle size. Growth in particle size is observed, when there is dissolved fluticasone propionate. The excipients present in the formulation dissolve some of the drug in the continuous phase. This results in particle instability over long-term storage.

a. Effect of Phase II Polymer Composition on Initial Particle Size

The composition of phase II is critical and not predictable to one skilled in the art. The step of forming the particles is a collaborative phenomenon between dispersion and coalescence of the droplets prior to precipitation. Further, the properties of the drug would need to be matched with the properties of the particle stabilizing polymer.

Figure 5:
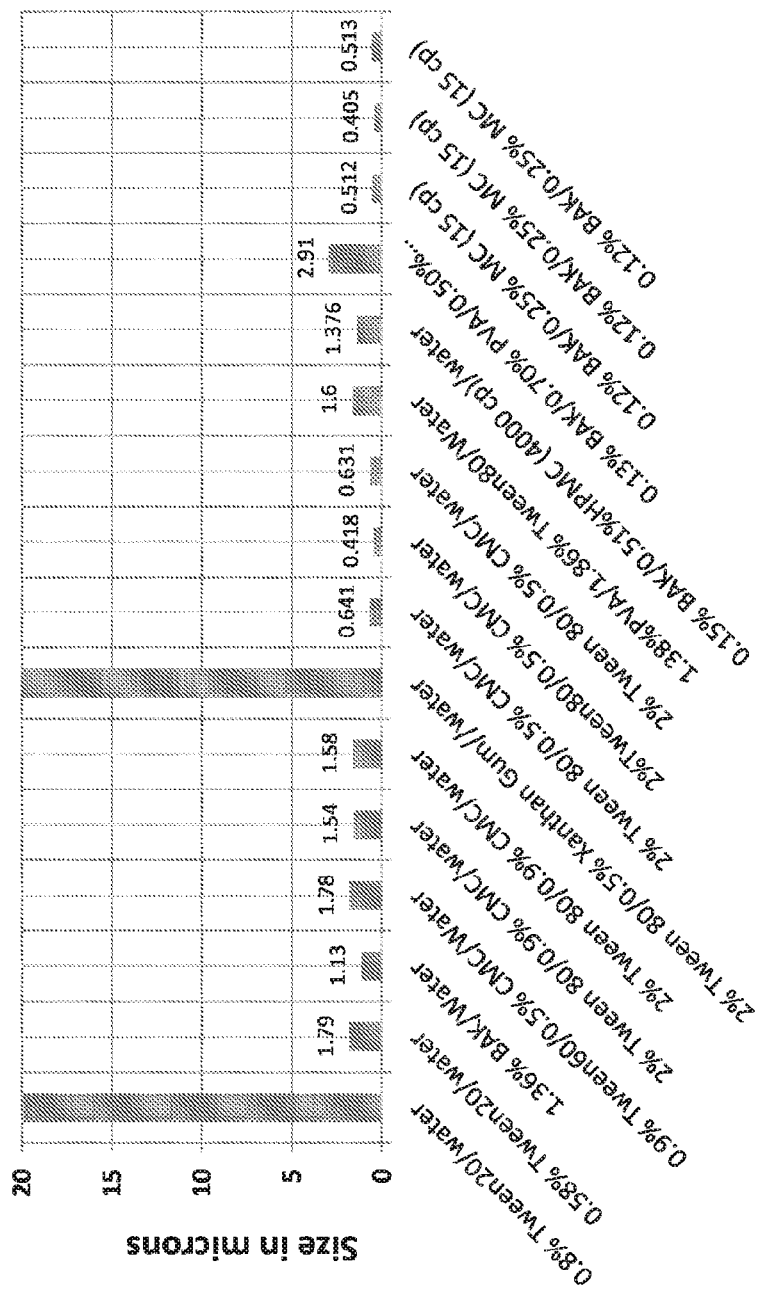
FIG. 5 is a plot showing that average sizes of fluticasone propionate nanocrystals are controllable by changing specific compositions of phase II solution.

As shown in FIG. 5, use of HPMC, PVA, PVP, pluronics, and mixtures thereof, produced particles that were greater than 1 micron in mean diameter. The combination of 2% TWEEN 20® (polysorbate 80) and 0.5% CMC in water as the phase II solvent appeared to produce particles that were smaller (0.4-0.6 microns). These particles however, grew over time to a size of 1.2 microns. Use of high viscosity polymers such as xanthan gum at 0.5% produced particles that were very large (>20 microns).

Phase III (Combination of Phase I+Phase II): The combination of 0.12% benzalkonium chloride/0.25% methyl cellulose (15 cP)/water in Phase II seemed to be the composition that produced the smallest particles reproducibly (400-600 nm, 15 batches). The combination of phase I and phase II is phase III, in which the nanocrystals are formed, while sonicating.

This phase III composition was also stable chemically for more than 4 weeks at 40 degrees C. This combination of polymers also maintains the particle size at its original size for 5-14 days.

b. Particle Size of Batches Obtained by Top-Down Techniques

Figure 6:
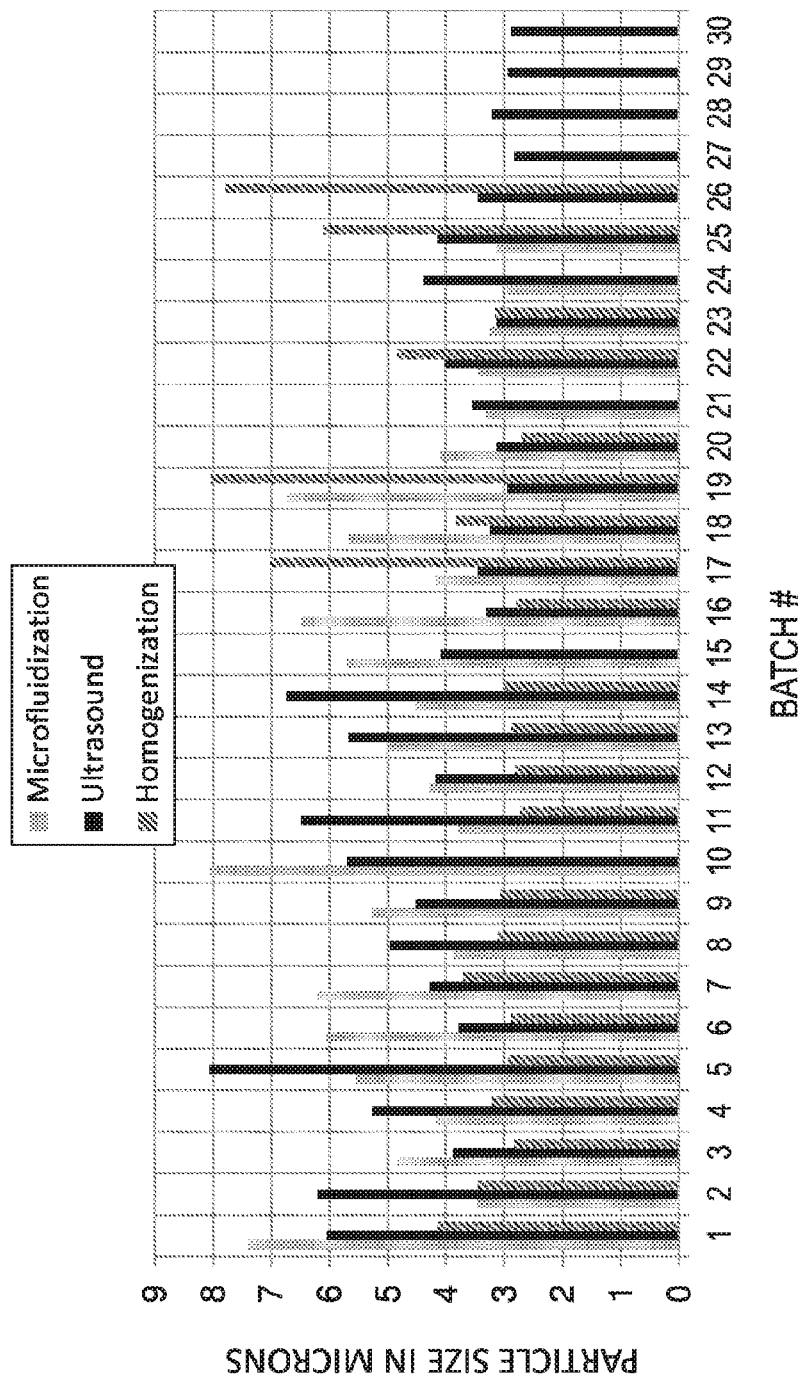
FIG. 6 is a plot showing particle sizes of fluticasone propionate produced by top-down techniques such as microfluidization, jet-milling, ultrasound sonication (wet milling) and homogenization.

A comparison was performed of particles produced by top-down techniques such as microfluidization, jet-milling, ultrasound sonication (wet milling) and homogenization. As shown in FIG. 6, the batches produced by these techniques produce particulates that were all greater than 2 microns. Some of the particles were 8 microns in size. The particles under the microscope appeared broken and debris-like.

c. Effect of pH of Phase II on Initial Particle Size

Figure 7:
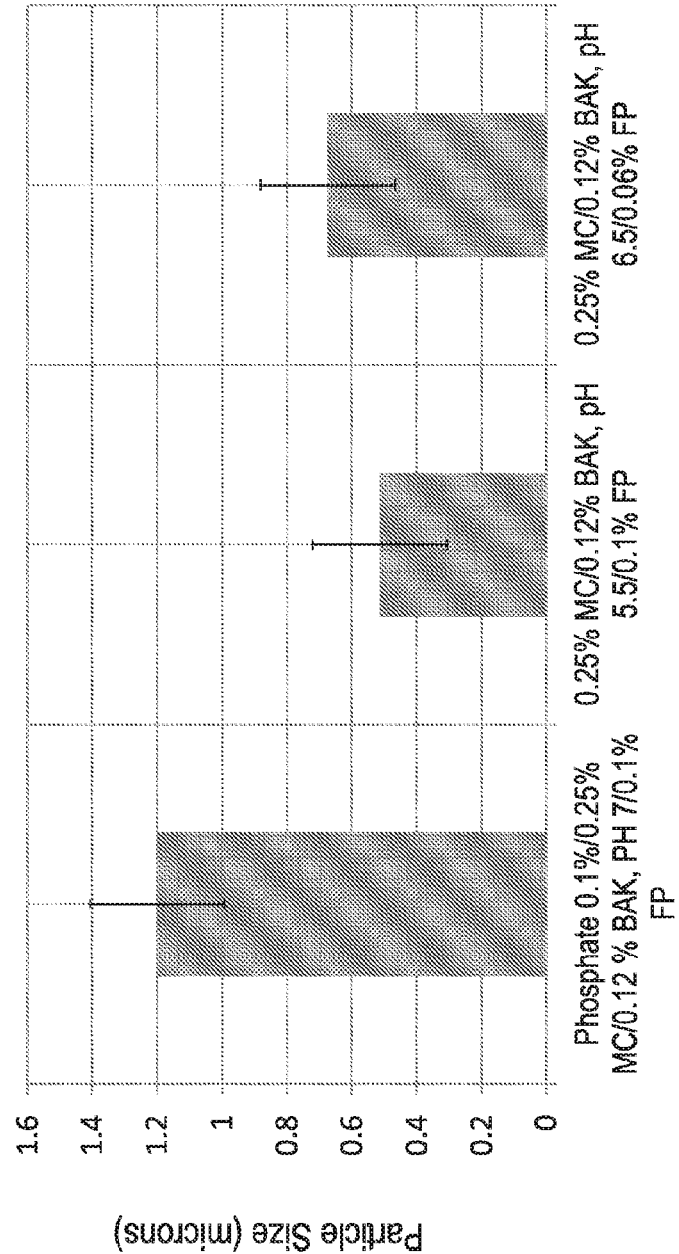
FIG. 7 is a plot showing the effect of pH of phase II solution on particle size of fluticasone propionate.
Figure 8:
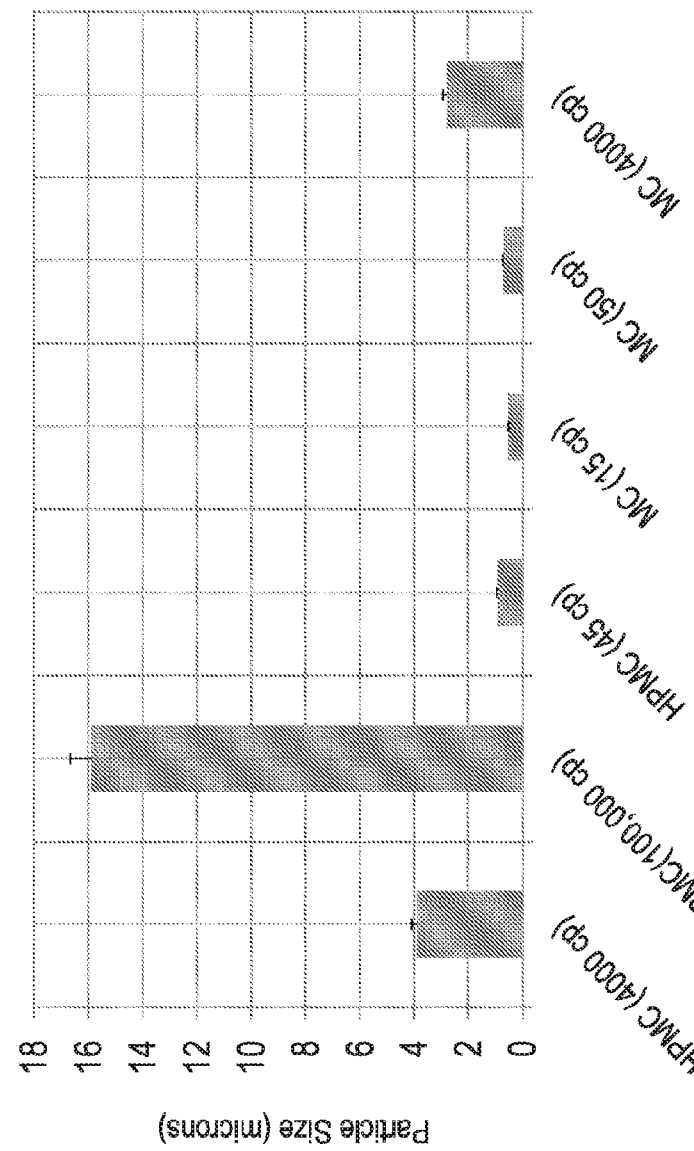
FIG. 8 is a plot showing the effect of different stabilizers in phase II solution on particle size of fluticasone propionate.

PH appears to play a critical role in the initial particle size, as shown in FIG. 7. When Phase II was pH balanced to pH 7-7.2 with phosphate buffer at 0.1% w/w, initial particle size was consistently higher (1.0-1.3 microns). When the pH was left unbalanced, the particle size was consistently between 500-800 nm. FIG. 7 shows the mean particle size of batches produced that were pH balanced and ones that were not pH balanced. The pH-unbalanced batches (n=3) were 5.5 for 0.1% Fluticasone propionate and 6.5 for 0.06% Fluticasone propionate (n=3). This effect of pH on particle size was unanticipated and unpredictable to one skilled in the art.

d. Effect of Molecular Weight of Steric Stabilizing Polymer in Phase II on Particle Size Molecular weight of the steric stabilizing polymer in phase II plays a significant role in the particle size of the nanocrystals, as shown in FIG. 8. For example, hydroxypropyl methylcellulose (HPMC) at 4000 centipoises consistently produces particles that are larger than those produced when HPMC at 45 centipoises are used.

e. Effect of pH on Particle Size Stability

Figure 9:
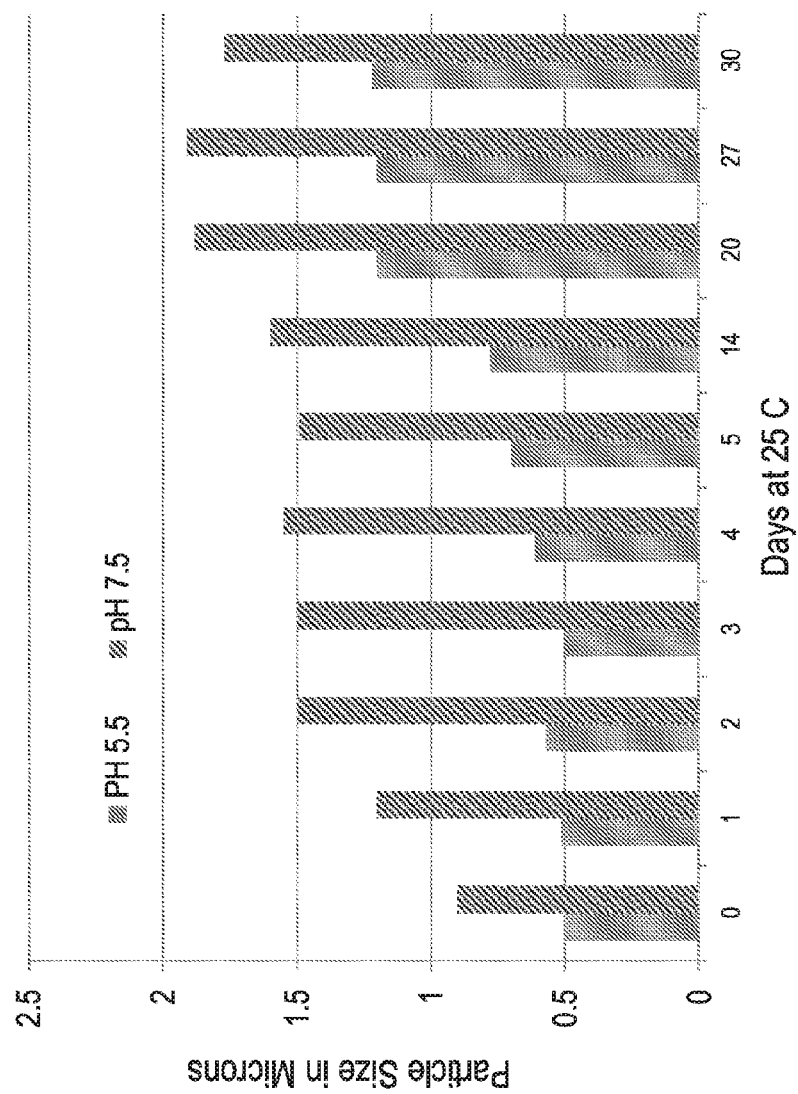
FIG. 9 is a plot showing the effect of pH of phase III mixture on particle size of fluticasone propionate.

The stability of the nanocrystals is controlled by the pH of phase III, which is formed by the combination of phase I and phase II. A 20 gram batch of nanocrystals were produced at pH 5.5 and placed on stability at 25 degrees C. Another 20 gram batch was produced at pH 7.5 and stability determined at 25 degrees C for 30 days. Unexpectedly, the particles at 7.5 grew rapidly to an average particle size greater than 1 micron. See FIG. 9. This phenomenon was verified for batches at the 50 gram scale.

f. Final Composition of Phase III Product (Phase I+Phase II)

The composition of phase III is 0.1% fluticasone propionate, 1.63% TWEEN 80® (polysorbate 80), 5% PEG400, 15% PPG400, 0.01% benzalkonium chloride, 0.2% methyl cellulose and 77.95% water. The pH of this phase is 5.5.

g. Purification of Nanocrystals of Fluticasone Propionate

Nanocrystals of fluticasone propionate were purified by exchange of the continuous phase by either tangential flow filtration or hollow fiber cartridge filtration. A high flow membrane is used for the filtration. Filters such as PVDF, PES are appropriate for this purpose, at pore size 0.22 microns or less. A tangential flow apparatus from MILLIPORE® (PELLICON® XL 50 system) can be used for this purpose.

For a batch size of 250 g, the nanocrystal suspension (Phase III) was poured into the 500 ml reservoir under a pump speed of 3, with the pressure never exceeding 30 psi. When the nanosuspension was washed down to 10 ml, the washing fluid was added. The washing fluid was 0.1% TWEEN 80® (polysorbate 80), fed into the reservoir at 30° C. The washing fluid was exchanged twice to ensure complete exchange of the buffer. The concentrate was then assayed for drug concentration. Based on the assay results, the reconstitute volume was adjusted to achieve the desired concentration. Additionally, methyl cellulose, sodium chloride, and phosphate were added to arrive at an osmolal composition.

Figure 10:
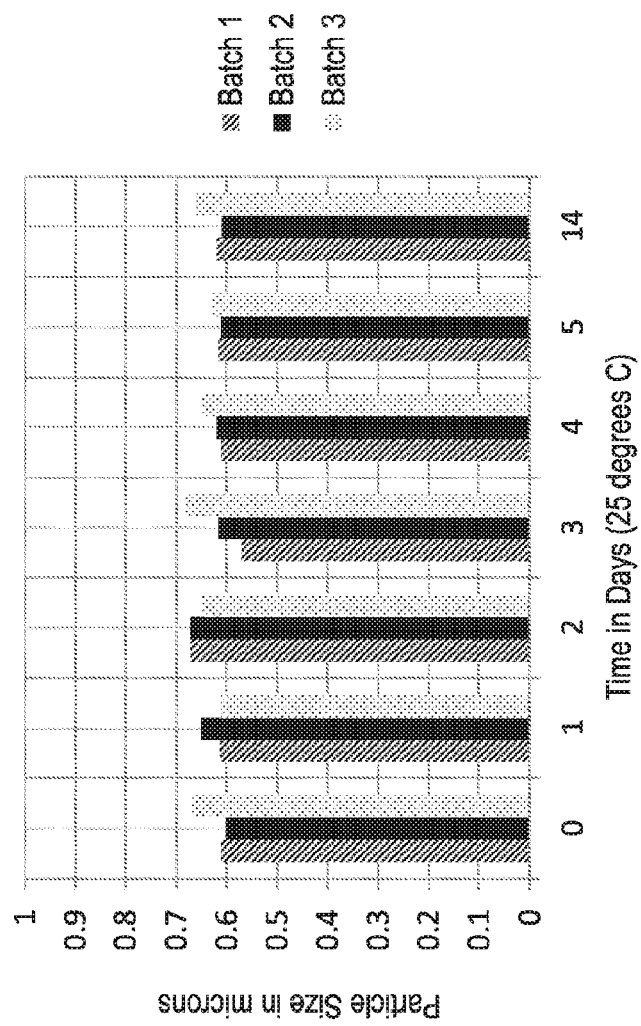
FIG. 10 is a plot showing that purified fluticasone propionate nanocrystals do not aggregate over time.

As shown in FIG. 10, the purified fluticasone propionate nanocrystals did not display any agglomeration over time.

Example 2

Exemplary Nanocrystal Manufacturing Process

The process to manufacture purified, stable, sterile nanocrystals of fluticasone propionate of size range 400-600 nm includes:

an in-situ crystallization step, whereupon a sterile phase I solution of fluticasone propionate in PEG400, PPG400, and TWEEN 80® (polysorbate 80) is mixed under sonication, at a flow rate between 1-1.4 ml/min with a sterile phase II solution comprising methyl cellulose between 15 cP-45 cP, benzalkonium chloride and purified water in the ratio 0.2-1 and pH between 5-6, to produce a sterile phase III suspension; and an annealing step, whereupon the fluticasone propionate nanocrystals in phase III are held in a holding tank in the temperature range of 25-40 degrees centigrade for a duration range of 30 minutes to 24 hours; and a purifying step, whereupon the fluticasone propionate nanocrystals are washed by exchange filtration through a membrane of pore size 0.1-0.22 microns by a sterile aqueous solution comprising of 0.1-0.5% TWEEN 80° (polysorbate 80); and a concentration step, whereupon the fluticasone propionate nanocrystals are concentrated to a range between 0.0001%-10%; and a final formulation step, whereupon additional excipients are added in sterile form to meet FDA and drug product criteria of osmolality, pH, viscosity, biocompatibility and permeability deemed appropriate for the particular product and clinical indication.

Example 3

Nanocrystal Manufacturing Process-Batch Process

The process described in this Example was applied to produce FP crystals in a size range of 400-600 nm. Particle size optimization using this process is a function of phase I and II composition, sonication output energy, flow rate of phase I, temperature of phase I and II. The flow rate of phase I for all batches (20-2000 g) was 1.43 ml/min.

The composition of phase I: FP: 0.45% w/w; TWEEN 80® (polysorbate 80): 7.67% w/w; PEG 400: 23.18% w/w, PPG400 (PPG=polypropylene glycol): 68.70% w/w. The composition of phase II: benzalkonium chloride: 0.020% w/w, methyl cellulose 15 cp 0.40% w/w, water (QS to 100%). The composition of phase III dispersion: FP: 0.225% w/w, TWEEN 80® (polysorbate 80): 3.796% w/w, PEG400: 11.577% w/w, PPG400: 34.41% w/w, benzalkonium chloride 0.01%, methyl cellulose (MC 15 cP): 0.2% w/w, water Q.S. to 100%. The volume ratio of Phase I to Phase II was 1:1 for this batch process.

The temperature of each phase I and II was 0-1° C. (ice water slurry). The sonication output energy was 25% using a ¾" probe and an OMNI® CELLRUPTOR® Sonicator. The pH of phase II was 5.5. Higher pH resulted in larger particles. It was also observed that at pHs<5, particle sizes were between 150-220 nm, but the drug began to degrade at the lower pHs.

Similar to Example 1, it was found that the size of the FP crystals was controlled by selecting proper stabilizers and pH values of the phase II solution. See, e.g., FIGS. 7 and 8.

Figure 11:
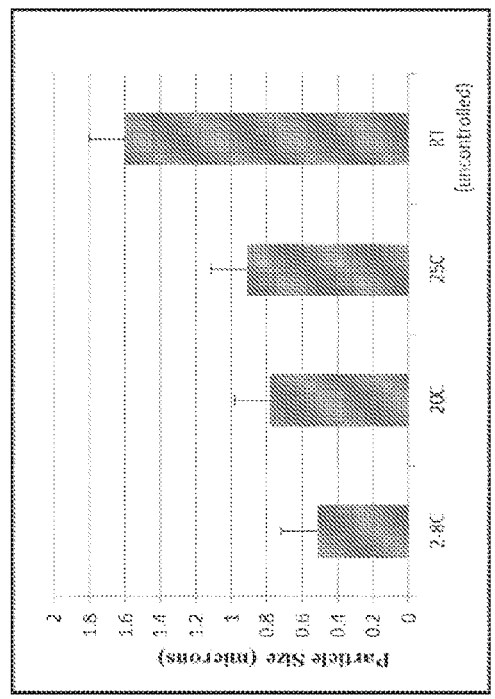
FIG. 11 is a plot showing the effect of temperature when mixing the phase I and phase II solutions on particle size of fluticasone propionate.

A particle size range of 400-600 nm was achieved with lower temperatures (FIG. 11). Particles produced at room temperature were large and aggregated, indicating soft amorphous regions.

Figure 12:
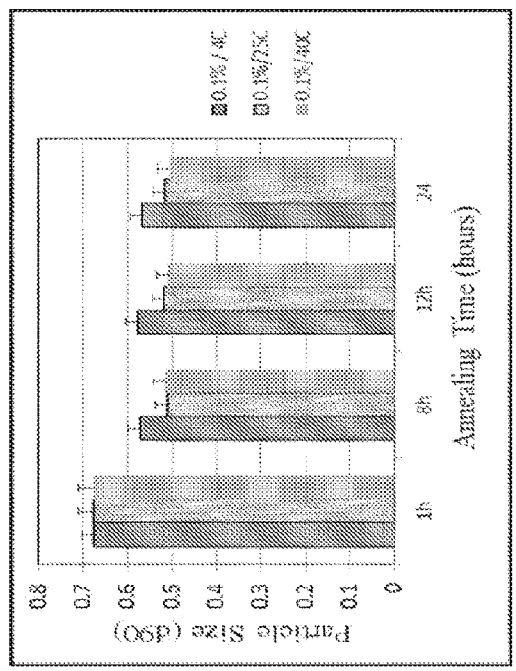
FIG. 12 is a plot showing the effect of annealing temperature and on particle size of fluticasone propionate with concentration of 0.1% in the phase III suspension.
Figures 13, 14:
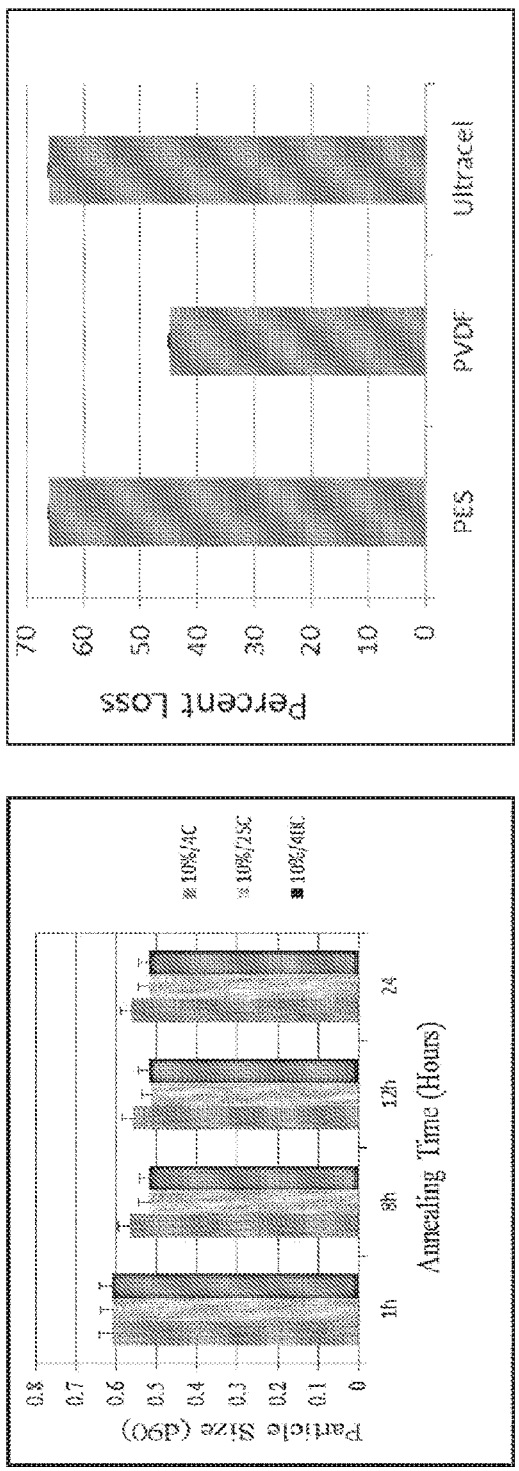
FIG. 13 is a plot showing the effect of annealing temperature and on particle size of fluticasone propionate with concentration of 10% in the phase III suspension.
FIG. 14 is a plot showing the effect of filter type on loss of drug crystals.
Figure 16:
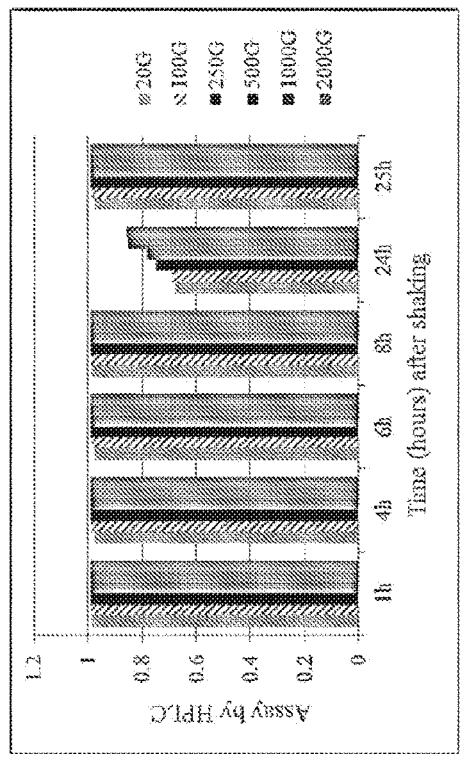
FIG. 16 is a plot showing the dispersibility of formulations as a function of batch scale (from left to right: 20 g, 100 g, 250 g, 1000 g, and 2000 g).

After fluticasone propionate crystals are prepared by sonocrystallization, the dispersion (phase III) was annealed at 25° C. The particles equilibrated to a steady particle size after at least 8 hours of annealing time (FIGS. 12 and 13). This annealing step unexpectedly, decreased the particle size. As shown in FIGS. 12 and 13, equilibrated particle size plateaus at 8 h and there is no statistical difference between different annealing temperatures, i.e., 4, 25 and 40° C. Further, the annealing effect is consistent for FP at concentrations of 0.1% and 10%.

Figure 15:
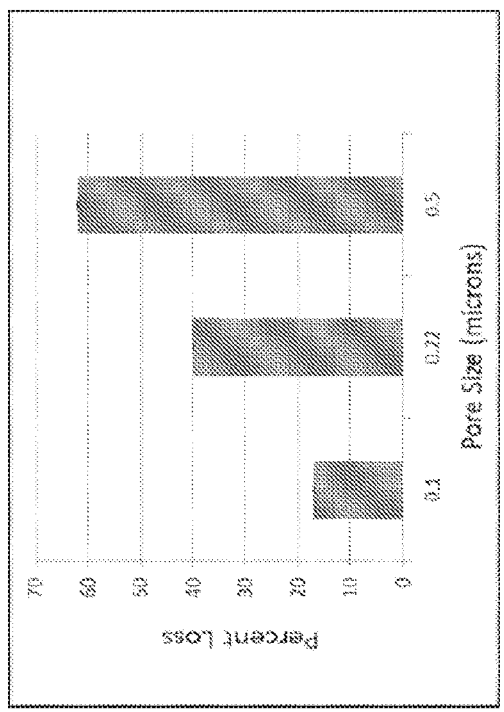
FIG. 15 is a plot showing the effect of filter pore size on loss of drug crystals.

The crystals produced by the above process were purified, either by tangential flow filtration or by continuous centrifugation. A lab scale PELLICON® XL50 filtration apparatus was used to develop the filtration conditions. The purpose of this step was to purify the crystals produced in the previous steps. FIGS. 14 and 15 showed that the drug loss using PVDF filters with a 0.1 micron pore size was minimal. Purification by centrifugation was accomplished by exchanging out the fluid with a solution of 0.1% w/w.

The final composition of fluticasone propionate was 0.0001-10% w/w, methyl cellulose 0.2% w/w (4000 cP), benzalkonium chloride 0.01% and water (Q.S.). The final formulation is flexible in that additional excipients can be added to the formulation, depending upon the indication.

Example 4

Dispersability of Nanocrystal from Batch Process

It was observed that the final compositions or formulations of FP produced in Example 3 remained dispersed over at least 8 hours. In particular, 5 ml of nanosuspension was placed in 10 ml glass screw-capped vials, all of which contained 0.1% FP nanosuspension in the final composition. Each vial was shaken 10 times top over bottom to disperse the sample well. After shaking, each vial was stored at 25° C. and sampled over time to 24 hours.

Each sample was redispersed after 24 hours and re-sampled (shown by the blue arrows in FIGS. 16 and 17). Sampling was performed by taking a 0.5 ml sample from the middle of the formulation. Samples were analyzed by assay by HPLC. As shown in FIGS. 16 and 17, the final formulations remain dispersed to at least 8 hours and re-disperse well on shaking. Also, concentrations 0.005%-10% FP all re-dispersed well, and re-dispersability was reproducible across the batch scales (20 g-2000 g). All concentrations were more than 80% dispersed at 24 hours at RT. All concentrations re-dispersed with shaking of vial, indicating a flocculated robust suspension. It was concluded that higher concentrations do not result in a faster rate of settling.

Example 5

Stability of Nanocrystal from Batch Process

It was also observed that the final compositions or formulations of FP were stable across all concentrations tested, i.e., 0.005%, 0.01%, 0.1%, and 10%. Samples were placed in 4° C., 25° C., 40° C. stability chambers. Stability timepoints: T=0 d, T=1 week, T=2 weeks, T=4 weeks.

Assay by HPLC showed that: 99-101% for 4° C., 25° C. and 106% for 40° C. There were no changes to impurities B, C and D in the samples tested from T=0 d. The pH (6.5-6.8) of the formulations tested did not change from T=0 d. Further, the FP particle size (505-620 nm) also did not change from T=0 d.

Example 6

Uniformity of Nanocrystals Composition

A new suspension formulation for fluticasone propionate (FP) containing sodium chloride, phosphate, methyl cellulose, TWEEN 80® (polysorbate 80), benzalkonium chloride and water was tested for content uniformity over time by sampling the top, middle and bottom of the suspension solution. The purpose was to determine the length of time the suspension particles remained equally distributed in solution after shaking.

About 20 ml of a 0.07% FP suspension was put into a vial and shaken 10 times up and down to suspend the FP particles. 200 μl samples were taken of the top, middle and bottom at 0, 0.5, 1, 3, 6.5 and 23 hours. All of the samples were analyzed by HPLC using a calibration curve. The samples were taken directly into an HPLC vial and diluted with 800 μl of diluent (75/25 acetonitrile/water). The weights of the 200 μl sample and 800 μl diluent were recorded and used in the final calculation of the amount of FP in each sample.

Results showed that there was little or no difference between the top, middle and bottom samples in the first 6.5 hours. The 23 hour sample however, visually had settled and was supported by the HPLC results.

Based on the dilution described above a three point calibration range was chosen from 0.056 to 0.45 mg/ml. See Table 11 below. Three standard solutions of FP were prepared from a 0.5787 mg/ml stock standard.

TABLE 11

Preparation of Standard Solutions

| Concentration (mg/g) | Wt of Stock (g) | Wt of Vehicle (g) (200 ul) | Weight of Diluent (g) | Total Weight of sample (g) |
|---|---|---|---|---|
| 0.05645 | 0.0822 | 0.1780 | 0.5825 | 0.8427 |
| 0.2813 | 0.4121 | 0.1891 | 0.2467 | 0.8479 |
| 0.4506 | 0.6579 | 0.1870 | 0 | 0.8449 |

A calibration curve was prepared using three known concentrations of a stock solution as described above and 200 ul of the blank vehicle to correct for any matrix affects that the vehicle may have on the standards.

Calculations for Concentrations were based on the formula:

(Wt of stock)×(Stock Standard)/(Total wt of sample)

The calibration curve is shown in Table 12 below. All of the standards are in mg of FP per grams of solution.

TABLE 12

Fluticasone Propionate Calibration Curve Data

| # injections | Standard Concentration (mg/g) | Area Counts | Average Area (injection 1, injection 2) | Slope | Intercept |
|---|---|---|---|---|---|
| 1 | 0.05645 | 3731.8 | 3729.45 | 65428.92758 | 37.85164626 |
| 2 | | 3727.1 | | | |
| 1 | 0.2813 | 18448 | 18447.35 | | |

TABLE 12-continued

Fluticasone Propionate Calibration Curve Data

| # injections | Standard Concentration (mg/g) | Area Counts | Average Area (injection 1, injection 2) | Slope | Intercept |
|---|---|---|---|---|---|
| 2 | | 18446.7 | | | |
| 1 | 0.4506 | 29517.1 | 29517.65 | | |
| 2 | | 29518.2 | | | |

Datafit: $R^2 = 1$

Using the calibration curve in Table 12, the time point samples were analyzed using the slope and intercept. Table 13 below shows the data obtained from the time-point sample analysis.

TABLE 13

Time Point analysis

| Sample (Hours) | Area (HPLC) | Con (mg/g) of HPLC Sample | Wt of HPLC Sample (g) | Wt of FP in HPLC Sample (mg) | Wt of 200 ul of layer (g) | Con of layer (mg/g) |
|---|---|---|---|---|---|---|
| 0 h-Top | 9310.8 | 0.1417 | 0.8393 | 0.119 | 0.1779 | 0.6686 |
| 0 h-Middle | 9842.3 | 0.1498 | 0.8574 | 0.128 | 0.1927 | 0.6667 |
| 0 h-Bottom | 10312.2 | 0.1570 | 0.8649 | 0.136 | 0.2007 | 0.6767 |
| 0.5 h-Top | 9233.2 | 0.1405 | 0.8397 | 0.118 | 0.1764 | 0.6690 |
| 0.5 h-Middle | 10364.8 | 0.1578 | 0.8659 | 0.137 | 0.2054 | 0.6654 |
| 0.5 h-Bottom | 10324.1 | 0.1572 | 0.8653 | 0.136 | 0.2015 | 0.6751 |
| 1 h-Top | 9142.1 | 0.1391 | 0.8329 | 0.116 | 0.1736 | 0.6676 |
| 1 h-Middle | 10089.1 | 0.1536 | 0.8611 | 0.132 | 0.2002 | 0.6608 |
| 1 h-Bottom | 10883.2 | 0.1658 | 0.877 | 0.145 | 0.2163 | 0.6721 |
| 3 h-Top | 9268.7 | 0.1411 | 0.8397 | 0.118 | 0.1787 | 0.6629 |
| 3 h-Middle | 9454.8 | 0.1439 | 0.8471 | 0.122 | 0.1874 | 0.6506 |
| 3 h-Bottom | 10351.5 | 0.1576 | 0.875 | 0.138 | 0.2136 | 0.6457 |
| 6.5 h-Top | 9588.2 | 0.1460 | 0.8504 | 0.124 | 0.1879 | 0.6606 |
| 6.5 h-Middle | 9555.9 | 0.1455 | 0.8553 | 0.124 | 0.1935 | 0.6430 |
| 65 h-Bottom | 10128.3 | 0.1542 | 0.8665 | 0.134 | 0.2051 | 0.6515 |
| 23 h-Top | 2479.1 | 0.0373 | 0.8478 | 0.032 | 0.1868 | 0.1693 |
| 23 h-Middle | 4041.1 | 0.0612 | 0.8507 | 0.052 | 0.1859 | 0.2800 |
| 23 h-Bottom | 27409.7 | 0.4183 | 0.867 | 0.363 | 0.2034 | 1.7832 |

Figure 18:
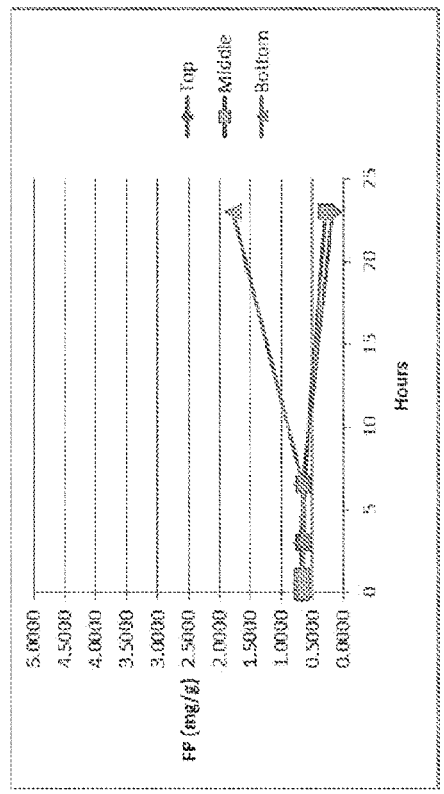
FIG. 18 is a plot showing the uniformity of formulation as a function of time.
Figure 17:
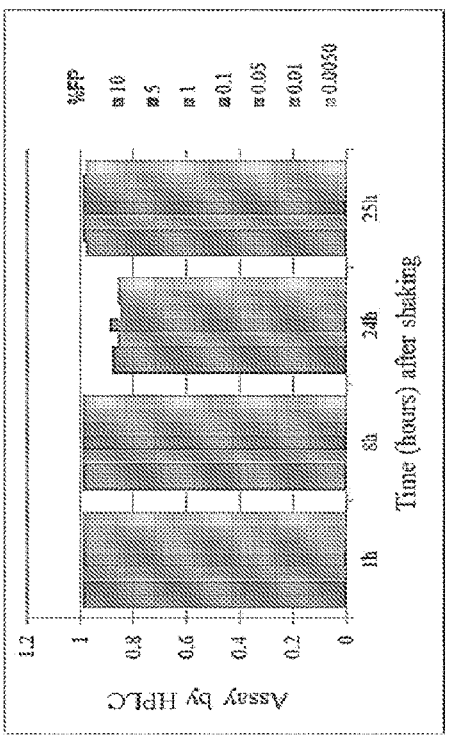
FIG. 17 is a plot showing the dispersibility of formulations as a function of FP concentration (from left to right: 10%, 5%, 1%, 0.1%, 0.05%, 0.01%, and 0.005%).

The data was also graphed over the entire time point range and was shown in FIG. 18.

Example 7

Nanocrystal Manufacturing Process-Flow Process

Nanosuspensions of fluticasone propionate at a particle size range of 400-600 nm were also prepared using a flow process scheme.

Figure 19:
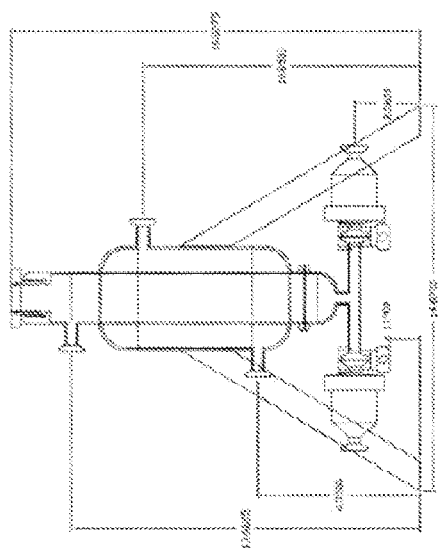
FIG. 19 is a scheme of a flow reactor.

Fluticasone propionate nanosuspensions were prepared using the flow reactor shown in FIG. 19. As shown in the flow schematic in FIG. 4, phase I and phase II were metered into the flow reactor.

The particle sizes of these nanosuspensions were measured with MALVERN® ZETASIZER® S90. Both Phase I and Phase II solutions, which were used for making nanosuspensions, were pumped continuously into the sonicator flow system. 25 batches of samples were prepared under a variety of conditions. The impact of the flow rates of both phases, the annealing temperature of Phase III, and the amplitude of sonicator on particle sizes, was analyzed. Most aspects of "batch process variables" as described in Examples 1 and 3 still applied, such as the temperature of mixing two phases, type and viscosity/molecular weight of the cellulosic stabilizer in phase II, pH of phase II, and the annealing temperature and time.

Materials and Equipment:
(A) Raw ingredients were listed in Table 14 below
(B) MALVERN® NANOSIZER® S90
(C) Flow Reactor
(D) Sonicator probe, size 25 mm. 1" with probe extender
(E) Pump I (NE-9000, New Era Pump Systems Inc.)
(F) Pump II (Console Drive, Cole-Palmer)

TABLE 14

| Excipients/drug | Manufacturer |
|---|---|
| Fluticasone | HOVIONE® |
| Methyl cellulose (15 cP) | SHINETSU® |
| Benzalkonium chloride (BKC) | SIGMA-ALDRICH® |
| Polypropylene glycol 400 | ALFA AESAR® |
| Polyethylene glycol 400 | SPECTRUM CHEMICAL® |
| TWEEN 80® (polysorbate 80) | SPECTRUM CHEMICAL® |

Both Phase I and Phase II solutions were prepared in advance before they were pumped into the flow system at 1:1 ratio. The preparation details and the compositions of both phases are described below, with 500 g batch as an example.

Preparation of Phase I (500 g Batch)

2.28 g of Fluticasone propionate was gradually added into a solution of 38.34 g of TWEEN 80® (polysorbate 80), 116 g of PEG 400, and 344 g of PPG 400. The solution of all components was vortexed and ultrasonicated using a standard sonication water bath until all of the solids went into solution.

| | (grams) | (%) |
|---|---|---|
| Fluticasone Propionate | 2.282 | 0.46 |
| TWEEN 80® (polysorbate 80) | 38.337 | 7.66 |
| PEG 400 | 115.994 | 23.17 |
| PPG 400 | 343.987 | 68.71 |

Preparation of Phase II (500 g Batch)

1 g of 10% benzalkonium chloride solution was added into 299 g of water and 200 g of 1% methyl cellulose (15 cP) mixture. The mixture was vortexed. The composition of Phase II was as follows: benzalkonium chloride 0.020%, methyl cellulose 15 cp 0.4%, water 99.58%.

Mixing Conditions of Phase I and Phase II (500 g for Each Phase; Total of 1000 g of Phase III)

The conditions for the mixing step are listed below:

Temperature of the mixture of Phase I and Phase II: 0~5° C.

Ultrasonicator tip size: 25 mm in diameter

Ultrasonicator amplitude: 25~75% (depending on the specific experiment)

Flow rate of Phase I: 12~700 ml/min (depending upon the specific experiment)

Flow rate of Phase II: 12~700 ml/min.

Chiller temperature: 0~−10° C.

Cooling air: 5 psi

Experiment duration time: 2~8 min.

Mixing Procedures (500 g Batch for Each Phase)

250 g Phase II was loaded into the sonicator. Chiller (0~−10° C.) and cooling air (5 psi) were then turned on. 500 g of Phase I was added into a 1000 ml beaker that sat in an ice/water mixture bath. The remaining 250 g of Phase II was added into another 1000 ml beaker that sat in an ice/water mixture bath. The temperature of each phase was stabilized for at least 30 minutes. The pump flow rates of each of the two phases were set as 12~700 ml/min. Then the ultrasonicator was turned on and amplitude adjusted. Turned on the pumps. Once both phases were pumped in, stopped the ultrasonication, pumps, and air generator.

25 batches of samples were prepared under a variety of conditions. Most batches have peak mean particle sizes below 1 micron, except three batches that were prepared at relatively high flow rates (e.g., 700 ml/min for each phase and 250 ml/min for each phase).

The Impact of Flow Rates of Both Phases on Particle Sizes

Figure 20:
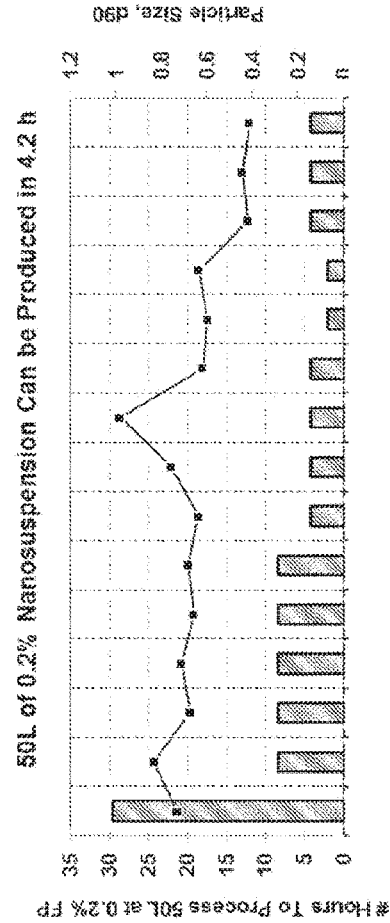
FIG. 20 is a plot showing the effect of flow rates on particle size of fluticasone propionate in the flow process.

Both phases were pumped at same actual flow rate (ratio of Phase I:II was 1). The particle sizes (represented by square dots in FIG. 20) were plotted against the final flow rates (represented by vertical bars in FIG. 20) of Phase III in FIG. 20. Three samples prepared with 200 ml/min have the smallest particle sizes about 400-600 nm.

Figure 4:
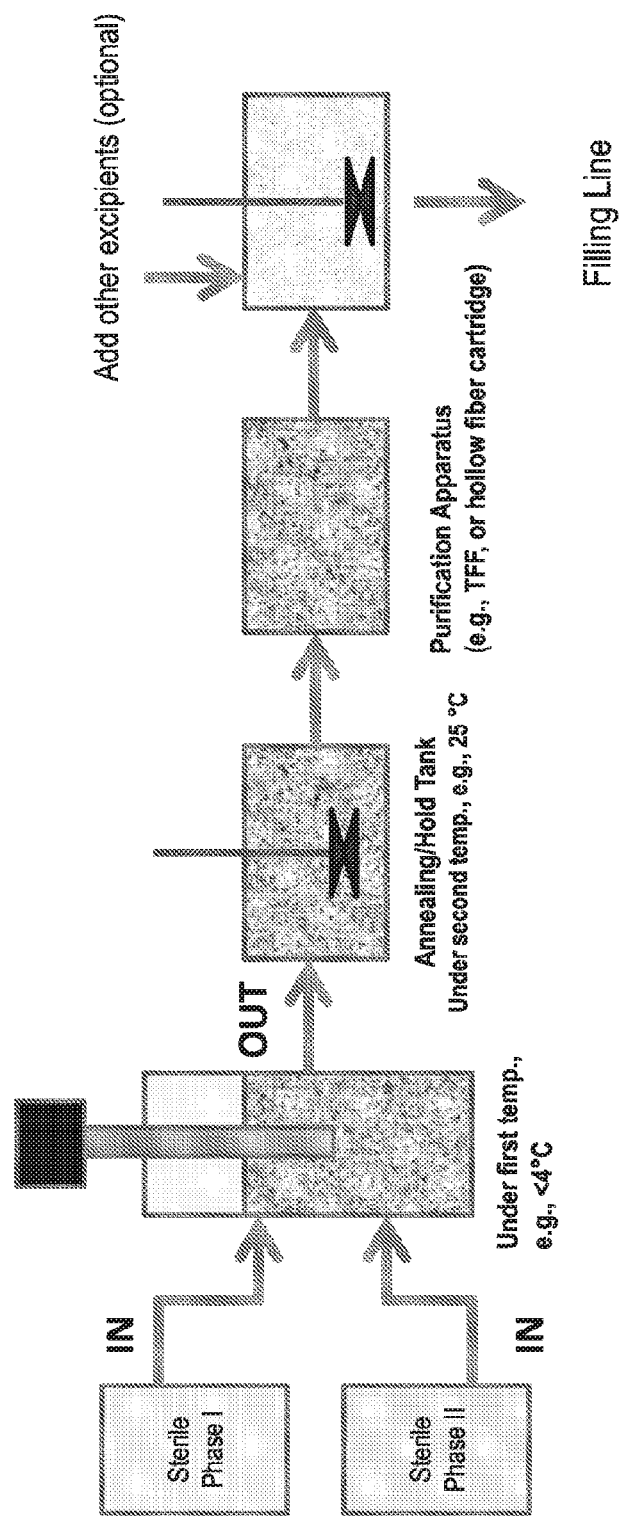
FIG. 4 is a scheme of another embodiment of the process of the invention (denoted as "flow process").

These experiments demonstrated that fluticasone propionate nanocrystals could be prepared using the flow process schematic shown in FIG. 4. Microscopic examination demonstrated plate-like morphology for the crystals. Preliminary stability studies on formulations prepared using the flow process (4 week stability at 25 and 40 C) showed stability of particle size and chemical integrity.

In general, trends were noted, as to the process variables that control particle size. Control of temperature of phase I and phase II to <2° C. led to consistent and robust production of uniformly sized particles. Other variables were the output energy of the sonication and flow rates of phase I and phase II. Flow rates appeared to be the controlling variable in generating particle sizes of uniform range. With the current sonicator probe design, the highest flow rates that achieved the particle size range of 400-600 nm was ~200 ml/min/pump, or 400 ml/min for phase III.

Example 8

Additional Characterization of Nanocrystals Manufactured by Batch Process

Nanocrystals of FP were prepared using a 1000 g batch process similar to that described in Example 1 or 3. The suspensions were collected into solids by centrifugation and dried in a vacuum oven for 12 hours. Two additional batches (i.e., b and c) were prepared using the same process.

Homogenized FP particles were prepared using a POLYTRON® (KINEMATICA AG), speed setting 4 in an aqueous dispersion. The samples were washed using a centrifugation process and dried in a vacuum oven.

Fluticasone propionate stock was used as received from the manufacturer.

Particle Size Assessment

Particle size of FP nanocrystals prepared by the batch process was measured by a MALVERN® ZETASIZER® S90. The particle sizes of batches (b) and (c) were measured by a MALVERN® MASTERSIZER S®. As shown in FIG. 21, the nanocrystals produced by the batch process produced a narrow distribution of crystals, within the size range 400-600 nm, whereas the stock FP material and the homogenized FP material had a broad particle size distribution (FIGS. 21B and 21C respectively).

Fluticasone Propionate Crystal Suspension is Highly Stable

Nanocrystals prepared by the batch process were tested on stability, to assess if the particle size distribution remained with a narrow range of 400-600 nm. The nanoparticles were formulated into a final vehicle that was comprised of 0.1% w/v FP, 0.90% w/v Sodium Chloride, 0.51% w/v Methyl Cellulose (MC 4000 cP), 0.10% w/v Sodium Phosphate, 0.20% w/v TWEEN 80° (polysorbate 80), 0.01% w/v Benzalkonium Chloride and 98.18% w/v water. The formulations were placed in stability incubators at 25° C. and 40° C.

Samples were measured for particle size, pH, osmolality and assay. All samples maintained pH, osmolality, particle size and assay [FP] over 75 days at 25° C. and 40° C. FIG. 22 shows stability of particle size over 75 days, even at 40° C.

This data suggest that fluticasone propionate prepared by the process of the invention is comprised of highly crystalline crystals and is of a stable morphological microstructure, evidenced by the absence of crystal growth over time (Ostwald Ripening).

Saturated Solubility and Rate of Dissolution

The saturated solubility of FP was measured by HPLC for the nanocrystals produced by the batch process of the invention, FP homogenized and FP stock material. The saturated solubility for all three materials was 40-45 µg/ml. In another study, the rate of dissolution of the nanocrystals (size range 400-600 nm) was compared to a batch that contained suspended and micronized fluticasone propionate in the size range 1-5 microns. The comparative rates of dissolution are shown in FIG. 23.

The purity of the fluticasone propionate nanocrystals was assessed and compared to the purity of the FP stock material as received from the manufacturer. Shown in FIG. 24A is the chromatogram of fluticasone propionate drug substance (retention time: 13.388 minutes) and its known impurities (shown at retention times 6.457 minutes and 9.720 minutes). Shown in FIG. 24B is the chromatogram of fluticasone propionate nanocrystals produced by the batch process. In comparison with the stock drug substance, fluticasone propionate nanocrystals produced by the batch process was of higher purity, with marked absence of the impurities at 6.457 and 9.720 minutes. Note that the scale for the HPLC chromatogram for fluticasone propionate crystals produced by the batch process was 0-500 mAU, compared to 0-1200 mAU for the stock material. Accordingly, it is concluded that the process of nanocrystallization and purification of the invention creates purer nanocrystals of fluticasone propionate.

Morphology of FP Nanocrystals

Shown in FIGS. 25A and B are optical micrographs (Model: OMAX, 1600×) of dried fluticasone propionate crystals prepared by the batch process and compared to FP, stock material. The appearance of the FP crystals produced by the nanocrystallization process is markedly differentiated from the fluticasone propionate drug substance, stock material. As seen in FIG. 25A, fluticasone propionate nanocrystals are rod-shaped, with a defined oriented geometry. In contrast, the stock material of fluticasone propionate did not appear to favor any specific shape or geometry.

The external appearance and morphology of FP crystals prepared by the batch process were compared to FP, stock material. Scanning Electron Micrographs were collected at 10,000× magnification using a HITACHI® SEM instrument. The experiments were performed at Microvision, Inc., Chelmsford, Mass.

Visually, the differences between the crystals produced by the batch process and the other samples are striking. The fluticasone propionate crystals prepared by the batch process were blade-like plates, or rods with a defined oriented geometry (FIGS. 26A and 26B). In contrast, the morphology of fluticasone propionate stock crystals appeared rounded, not plate-like or with angled edges as the fluticasone propionate crystals produced by the batch process (FIG. 27A).

FIG. 27B is the scanning electron micrograph of the homogenized particles of FP (top-down process). Visually, these particles appeared similar to the stock material.

Thermal Characteristics

To measure the thermal properties for each fluticasone propionate specimen, approximately 10 mg was collected from each specimen and placed in a clean alumina crucible. The table below summarizes the testing conditions and parameters for the simultaneous thermal analysis tests. The samples were (a) Fluticasone Propionate nanocrystals, and (b) Fluticasone Propionate, stock material. The specimens were tested under a heating rate of 10° C./min starting at 30° C. until reaching a final temperature of 350° C. This process was repeated for each specimen. The experiments were performed at EBATCO, LLC, Eden Prairie, Minn.

TABLE 15

Simultaneous Thermal Analysis Testing Conditions and Parameters

| Samples | Fluticasone Propionate Stock, Fluticasone Propionate Crystals produced by the batch process |
| --- | --- |
| Test instrument | STA 449 F3-JUPITER ® |
| Crucibles | Alumina ($Al_2O_3$) |
| Heating Rate | 10° C./min |
| Initial Temperature | 30° C. |
| Final Temperature | 350° C. |
| Purge Gas | Nitrogen, 20 mL/min |
| Protective Gas | Nitrogen, 30 mL/min |

Thermal analysis test results are shown for each sample, in Table 16 below. The softening temperature of a substance, also known as the glass transition temperature was significantly lower for the fluticasone propionate stock material (57.6° C.) compared to the fluticasone propionate crystals produced by the batch process. Additionally, the heat of melting for the fluticasone propionate crystals produced by the new process was significantly higher (54.21 J/g) than the FP stock material (48.44 J/g), indicating that the former was a more crystalline material, requiring more energy to break inter-molecular bonds such as ionic and hydrogen bonds.

TABLE 16

| Specimen | Mass Change (%) | Glass Transition Upper Limit (° C.) | Melting Temperature Range (° C.) | Latent Heat of Melting (J/g) |
| --- | --- | --- | --- | --- |
| FP nanocrystals | −46.12 | 63.5 | 10.1 | 54.21 |
| FP Stock Sample | −47.96 | 57.6 | 11.0 | 48.44 |

FIG. 28A shows the combined DSC/TGA of fluticasone propionate crystals produced by the batch process. In comparison with the thermal characteristics of fluticasone propionate stock material (FIG. 28B), the onset of melting of the FP nanocrystals was higher than the onset of melting of the fluticasone propionate stock: $onset_{melting}$ (FP nanocrystals from batch process) 299.5° C.>$onset_{melting}$ (FP, stock) 297.3° C. Additionally, as evidenced by thermo-gravimetric (TGA), the onset $temperature_{mass\ loss}$ (FP nanocrystals from batch process) 299° C. is higher than the onset $temperature_{mass\ loss}$ (FP, as is) 250° C. The data suggest that the fluticasone propionate crystals produced by the batch process have thermal behavior indicative of material more crystalline and ordered than the fluticasone propionate stock material.

Fluticasone Propionate Crystals Prepared by the Batch Process are not Solvates or Hydrates Theoretically, when solvents are entrapped in the crystal structure, they are termed "solvates". When the specific solvent is water, the crystals are termed "hydrates". Solvates and hydrates of a particular crystalline form display different properties such as dissolution, density, etc. Differential Scanning calorimetry (DSC) can be used to detect the presence of an entrapped solvent, which can be induced to escape from the crystal lattice when heated. For crystals prepared utilizing the batch process, there were no additional melt transitions (DSC) or multi-phasic mass loss (TGA) (FIG. 28A) denoting that the crystals were pure crystals, not solvates or hydrates. Fluticasone Propionate stock material was also not a solvate or a hydrate, but of crystalline structure, as expected (FIG. 28B).

Fluticasone Propionate Crystals Produced by Batch Process have Higher Bulk Tap Density Compared to Fluticasone Propionate Stock Material The tap density of dried fluticasone propionate crystals prepared by the batch process was 0.5786 $g/cm^3$. In contrast, the tap density of fluticasone propionate stock was 0.3278 $g/cm^3$. The data suggest that fluticasone propionate crystals produced by the batch process have a higher packing than the stock fluticasone propionate.

Fluticasone Propionate Crystals Produced by Batch Process are not Amorphous or Partially Amorphous It is to be noted that the fluticasone propionate crystals produced by the batch process do not display "cold crystallization", or crystallization or amorphous phases prior to melting. Presence of a single, sharp melt transition at 299.5° C. suggests lack of an amorphous or amorphic phase in the material. The sharpness of the melt transition (melting range 10° C.) also denotes a highly ordered microstructure. In contrast, fluticasone propionate stock material melted over a slight wider range (11.1° C.).

Fluticasone Propionate crystals produced by the batch process and fluticasone propionate stock material were compared with each other with respect to their infrared vibrational frequencies (FTIR), using a NICOLET® Fourier Transform Infrared Spectrophotometer. FTIR is utilized to confirm/verify identity of a known organic substance, since specific bonds and functional groups vibrate at known frequencies. The FTIR spectrum of fluticasone propionate crystals produced by the batch process did not show presence of any additional vibrational frequencies (FIG. 29), when compared to the known FTIR spectrum of fluticasone propionate (FIG. 30).

Crystal Structure of Fluticasone Propionate Produced by the Process of the Invention vs. the Two Known Forms of Fluticasone Propionate Polymorph 1 and polymorph 2 are the two crystal forms of fluticasone propionate published previously. See, e.g., U.S. Pat. No. 6,406,718 B1 and J. Cejka, B. Kratochvil and A. Jegorov. 2005. "Crystal Structure of Fluticasone Propionate", Z. Kristallogr. NCS 220 (2005) 143-144. From published literature, polymorph 1 is the most stable known form of fluticasone propionate, in that it is the most abundant. Polymorph 1 is formed by free crystallization from solvents of medium polarity (acetone, ethyl acetate and dichlorimethane). Polymorph 2 crystallizes from supercritical fluid and only described in U.S. Pat. No. 6,406,718 B1, with no other published accounts.

The crystal structure of polymorph 1 is provided in Cejka, et. al, with the following unit cell characteristics: $C_{25}H_{31}F_3O_5S$, monoclinic, $P12_11$ (no. 4), a=7.6496 Å, b=14.138 Å, c=10.9833 Å.

The crystal structure of polymorph 2 is provided in U.S. Pat. No. 6,406,718 B1 and Kariuki et al, 1999. Chem. Commun., 1677-1678. The unit cell lattice parameters are a=23.2434 Å, b=13.9783 Å and c=7.65 Å. The unit cell was described as orthorhombic. As noted in Kariuki et. al, there were striking similarities between the two crystal structures. For reference, the calculated XRPD powder patterns of polymorph 1 (red) and polymorph 2 (blue) are shown in FIG. 31B.

In the first set of studies to determine the crystal structure of fluticasone propionate nanocrystals prepared by the batch process to compare with the crystal structure of fluticasone propionate stock material, X-Ray Powder Diffraction (XRPD) patterns of both materials were collected by X-Ray Diffractometer (Shimadzu XRD 6000 Diffractometer operating at 40 KV and 30 mA. The samples were split and pulverized for analysis. The samples were scanned from 10 to 65 degrees two-theta 0.02° steps at 2 seconds per step. Diffracted x-rays were collimated using a 0.05° receiving slit and detected with a solid state scintillation detector. Peak intensity and resolution calibration were verified using solid quartz standard 640 d. These studies were performed at XRD Laboratories, IL.

The XRPD patterns of both Fluticasone Propionate crystals prepared by the batch process and Fluticasone Propionate stock material were compared with calculated XRPD patterns from the published crystal structures of Polymorph 1 and 2. An overlay of the XRPD patterns of Fluticasone Propionate stock and Fluticasone propionate Polymorph 1 indicated that the FP stock material existed as the polymorph 1, the most abundant and stable polymorph.

An overlay of XRPD patterns of FP crystals by homogenization (example of a "top-down" process) and the FP stock material demonstrated excellent "peak-to-peak" agreement between the patterns, even the intensities. It can be concluded that the Fluticasone Propionate homogenized sample is of an identical polymorph as Fluticasone Propionate Stock (polymorph 1). In contrast, the XRPD pattern of fluticasone propionate crystals (batch process) was overlaid (black) on that for published polymorph 1 (red) and polymorph 2 (blue), there were clear differences in the diffraction pattern, shown in FIG. 31B. Further experiments performed at Triclinic Labs, Inc. determined the unit cell structure of the crystals produced by the batch process and the microstructural differences with standard polymorph 1. The data suggest that fluticasone propionate crystals produced by the new process had a novel and differentiated microstructure than standard polymorph 1.

Unit Cell Structure of Fluticasone Propionate Nanocrystals Prepared by the Batch Process All samples were prepared by filling the sample holder cavity with powder and gently pressing the sample to give a flat reference surface. Any excess material was removed and returned to the original container. All measured data sets were pre-processed to remove background and scaled to a common area of 100000 counts over the common measurement range. Indexing is the determination of crystal unit cells using measured diffraction peak positions. Peak positions for the provided XRPD data files were initially determined using WINPLOT R®.

To model the peak intensity differences between the XRPD data sets (FP, batch process and Polymorph 1), a crystalline harmonic preferred orientation function was added to the crystal structure description, to test the hypothesis that the FP (batch process) were a novel crystalline habit. The allowed harmonic symmetries were 2/m and 'fiber' using 8 harmonic terms in the expansion. With the preferred orientation function added to the crystal structure description of standard polymorph 1, the XRPD patterns of standard polymorph 1 and fluticasone propionate crystals produced by the batch process could be matched. This proved that FP (batch process) was a novel crystalline habit of polymorph 1.

By definition, a crystalline habit of a known polymorph has different microstructure such as planes of orientation, etc. (Miller Indices) that can lead to a different shape and appearance, while having the same unit cell structure and type. In the case of fluticasone propionate produced by the batch process, the crystals had a different appearance (demonstrated by SEM in FIG. 26) than the stock material (FIG. 27).

The differences between the XRPD data collected on micronized and proprietary batches of FP crystals were essentially differences in diffraction peak intensity. Peaks with non-zero '1' Miller indices were seen to significantly increase in intensity for the proprietary material. Rietveld modeling of the proprietary material confirmed that within the reflection powder samples, the FP nanocrystals from the batch process were strongly aligned with the [001] (c-axis) crystallographic direction normal to the sample surface. This suggests that a well-defined crystalline habit is produced by the proprietary production method and that the habit is most likely plate or blade like in nature. The proprietary material packed differently in the XRPD sample holder, due to the consistent habit, leading to the observed preferred orientation (PO). On the other hand, the stock material did not exhibit any significant preferred orientation (PO).

The effective crystal structure derived for the proprietary material further suggests a blade or plate like habit with the crystallographic a-b plane lying almost parallel to the largest exposed surface. The effective crystal structure can be used to investigate the functional groups of the API exposed by the largest crystal face of the blade habit.

The unit cell structure of the fluticasone propionate crystals produced by the batch process is Monoclinic, P21, a=7.7116 Å, b=14.170 Å, c=11.306 Å, beta=98.285, volume 1222.6. In comparison, the crystal structure of polymorph 1 is provided in Cejka, et. al, with the following unit cell characteristics: $C_{25}H_{31}F_3O_5S$, monoclinic, $P12_11$ (no. 4), a=7.6496 Å, b=14.138 Å, c=10.9833 Å.

Thus, it can be stated that the fluticasone propionate (via batch process) is a novel crystalline habit which occupies a similar unit cell type as polymorph 1, which is the most stable and most abundant crystal state published to date. Since the most stable polymorphs have theoretically the highest melting point, it can be deduced that the novel crystalline habit (fluticasone propionate via the process of the invention) may be the most stable crystal structure of the drug substance discovered to date. As mentioned above, the melting point of the novel crystals was 299.5° C., as opposed to 297.3° C. for the stock material (polymorph 1), as shown in FIGS. 28A and 28B. Also, the existence of the novel crystalline habit in FP nanocrystals produced by the process of the invention was reproducible.

MAUD is able to produce 'pole-figures' for specific crystallographic directions based upon the preferred orientation parameters derived during the Rietveld modeling. For each crystallographic axis selected, the pole figure illustrates the angular distribution of that crystal axis about the surface of the reflection sample holder. For an ideal powder, all crystallographic axes will be randomly oriented giving a pole figure with a uniform color. For a single crystal sample, each crystallographic axis will be oriented in a single direction. If that direction is normal to the sample surface then the pole figure will show a single high intensity spot in the center of the plot. The pole figures derived from the XRPD data collected on the FP nanocrystals via batch process showed a single high intensity central pole for the [001] crystallographic axis. This is indicative of strong preferred orientation with the crystallographic c-axis being normal to the surface of the powder sample. One possible driving force for this strong preferred orientation occurs if the crystalline habit is plate like or blade like. When packed into a reflection holder and pressed flat, the flat surfaces of the crystal tend to align parallel with the sample surface (like sheets of paper). This suggests that for the FP nanocrystals from the batch process, the crystallographic c-axis is close to normal through the largest flat crystal face. In contrast, pole figures calculated for the FP stock material showed a general distribution of crystallographic orientations more typical of a close to randomly oriented sample.

Example 9

Triamcinolone Acetonide (TA) Crystal Manufacturing Process-Batch Process

Triamcinolone acetonide is a synthetic corticosteroid used to treat various skin conditions, relieve the discomfort of mouth sores and in nasal spray form as an over-the-counter relief for allergic and perennial allergic rhinitis. It is a more potent derivative of triamcinolone, being about 8 times as potent as prednisone. Its IUPAC name is (4aS,4bR,5S,6aS, 6bS,9aR,10aS,10bS)-4b-fluoro-6b-glycoloyl-5-hydroxy-4a, 6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one, with molecular formula of $C_{24}H_{31}FO_6$ and molecular mass of 434.5 g mol$^{-1}$.

Triamcinolone Acetonide Solubility

Triamcinolone Acetonide (TA), stock was used as received from the manufacturer. Solubility of Triamcinolone Acetonide (TA) was measured in propylene glycol, polypropylene glycol, TWEEN 20® (polysorbate 20), TWEEN 80® (polysorbate 80), PEG 400.

Initially, 5 mg of the TA was added to 10 g of solvent; the mixture was vortexed for 5 min, and sonicated for 10 min in a water bath. 1-5 mg of TA was added when the initial amount dissolved in the solvent completely—clear solution of TA in solvent. The process was continued until saturation solubility was reached. The solvent that provided the highest solubility was chosen for further development as Phase I.

The solubility of TA was evaluated in various pure non-aqueous systems in order to prepare Phase I. TA is practically insoluble in water. The solubility of TA in propylene glycol, polypropylene glycol, PEG 400, TWEEN 20® (polysorbate 20) and TWEEN 80® (polysorbate 80) was evaluated. Initially, 5 mg of TA was added to these solvents and the suspension was vortexed and sonicated for 15 min in a water bath at 37° C. When the API (i.e., TA) dissolved, 1 mg of drug was added to the vial. This process was continued until a preliminary estimation of the drug in all solvents was achieved. The solubility of TA in Propylene glycol, polypropylene glycol, PEG 400, TWEEN 20® (polysorbate 20) and TWEEN 80® (polysorbate 80) was 14, 8, 7, 5.5 and 4 mg/mL, respectively.

Preparation of TA nanocrystals

Phase I

This is the phase that the drug is solubilized in. Phase I was prepared with the highest concentration of API in a chosen solvent. Since propylene glycol exhibited as a better solvent, it was chosen for further development. The final composition of phase I: TA: 1.4% w/w, PG (PG=Propylene glycol). The batch size was 50 grams.

Phase II

The composition of phase II: Benzalkonium chloride: 0.0125% w/w, methyl cellulose 15 cp 0.257% w/w, water (QS to 100%). Since the TA degrades at higher pH (see, e.g., Ungphaiboon S et al. Am J Health Syst Pharm. 2005 Mar. 1; 62(5):485-91), 0.1% citric acid was added to lower the pH of the solvent. The final pH Phase II was 3.91. The batch size was 100 grams. Phase II was cooled down to 0° C. in ice-water slurry.

Generation of Phase III and Annealing

This procedure generates 150 grams of Phase III. The combination of phase I and phase II produces nanocrystals of API dispersed in a vehicle. This dispersion is Phase III.

Phase III was prepared by metering 50 g of Phase I into 100 g Phase II.

50 grams of Phase I was filled into a 60 ml syringe fitted with a needle that was 6 inches long and 18 gauge. 100 g of Phase II was poured into a 250 ml beaker and cooled to 0° C., using an ice-water slurry. Sonication was performed using Sonic Ruptor™ ultrasonic homogenizer (OMNI INTERNATIONAL®) at a setting of 20% intensity, using a titanium probe that was ¾ inches in diameter. The flow rate of Phase I was kept at 1.43 ml/min. Phase III was collected in a 250 ml pyrex beaker. The resultant Phase III was a milky-white dispersion. The dispersion was annealed at 25° C. for 4 hours in the 250 ml beaker, covered with parafilm. The composition of phase III dispersion: TA: 0.41% w/w, PG: 32.86% w/w, benzalkonium chloride 0.01%, methyl cellulose (MC 15 cP): 0.2% w/w, water 66.93% w/w.

Purification

This slurry was subsequently subjected to centrifugation (3×) at 10,000 rpm and 4° C. The following steps were performed:

The slurry was divided into 6 50 ml polypropylene centrifuge tubes at 25 ml each. To each tube was added 25 ml of the "wash" solution. The wash solution consisted of 0.01 w/w % benzalkonium chloride and 0.2% w/w TWEEN 80® (polysorbate 80) in distilled water. Thus, the dilution was 1:1.

The diluted slurry was centrifuged at 10,000 rpm and 4° C. for 90 minutes, using a THERMO-SCIENTIFIC® IEC CL31R MULTI-SPEED®.

After pelletizing, the pellets were re-dispersed with the wash solution, filled to the 50 ml mark. The dispersion was centrifuged as described previously.

After two washes, the pellets were consolidated into two 1.5 ml centrifuge tubes and re-dispersed with ~1 ml of the washing solution. The dispersion was centrifuged again using an EPPENDORF® Centrifuge 5415D at 12,000 RPM for 12 minutes.

The pellets were collected and consolidated into a 50 ml centrifuge tube and re-dispersed it in 40 ml of washing solution. Dispersion was achieved by vortexing and then sonicating it in water bath for 15 minutes at room temperature. The dispersion was centrifuged at 10,000 RPM for 10 minutes.

The supernatant was decanted and the pellet was dried for 72 hours at RT using vacuum oven (VWR International, Oregon, USA).

Example 10

Characterization of TA Crystals Manufactured by Process-Flow Process

Particle sizing was performed on the Phase III dispersion made in Example 9 above, after annealing. MALVERN® dynamic light scattering equipment (Model S90) was used to determine the nanocrystal size and size distribution. To measure the particle size, 40 microliters of the suspension was pipetted into 2960 microliters of 0.1% benzalkonium chloride (BKC). An intensity of $5 \times 10^4$-$1 \times 10^6$ counts/s was achieved. The particle size distribution of formulation was measured in triplicate. The average size of the TA particles from Example 9 was in the 300-400 nm size range (n=3). See FIG. 32.

Thermal Characteristics of TA Nanocrystals vs. TA Stock Material

Thermal properties of the TA particles from Example 9 were investigated using a SHIMADZU® DSC-60 and TGA-50.

Approximately 10 mg of sample was analyzed in an open aluminum pan, and heated at scanning rate of $10°$ C.·min$^{-1}$ from room temperature to 320° C. FIG. 33 shows the differential calorimetry scan of TA API. Peak of the heat of melting is at 289.42° C., with $\Delta H_m$=83.50 J/g. In comparison, peak of the heat of melting for the nanocrystals produced by the process described in Example 9 is at 275.78° C., with $\Delta H_m$=108.45 J/g (FIG. 34). The data suggest that TA nanocrystals are markedly more crystalline, evidenced by a higher heat of melting. Further, the large shift in melting point for the nanocrystals (compared to the API) suggests differences in the internal crystal structures.

FIGS. 35 and 36 are TGA scans of the TA stock material and the TA nanocrystals respectively. Comparatively, it is clear that the both these materials have very similar weight loss profiles when heated, indicating that the same molecular bonds are breaking as the substances are heated. However, as in the DSC profiles there are marked differences in the onset of each phase of weight loss between the materials, suggesting differences in crystal structure and morphology.

Morphology of TA Nanocrystals vs. TA Stock Material

Figure 37B:
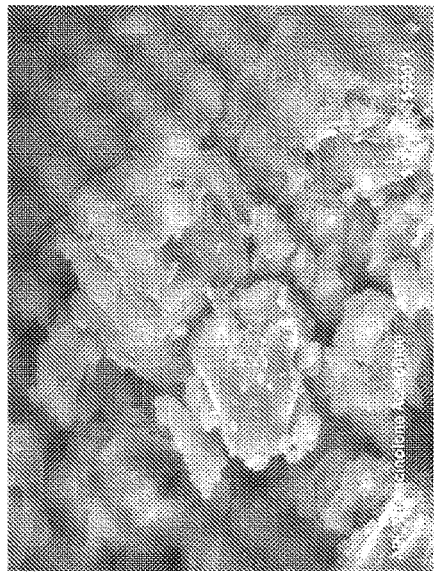
Figure 37D:
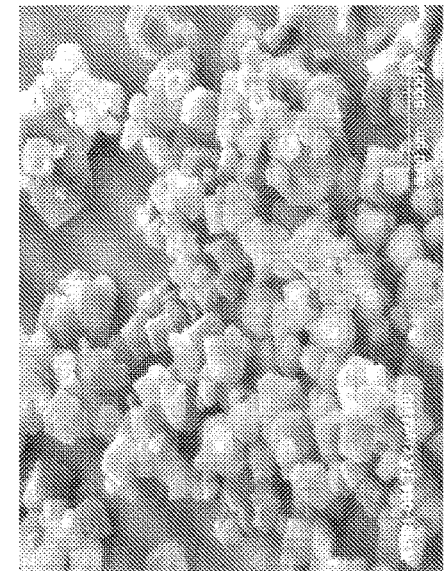
Figure 37A:
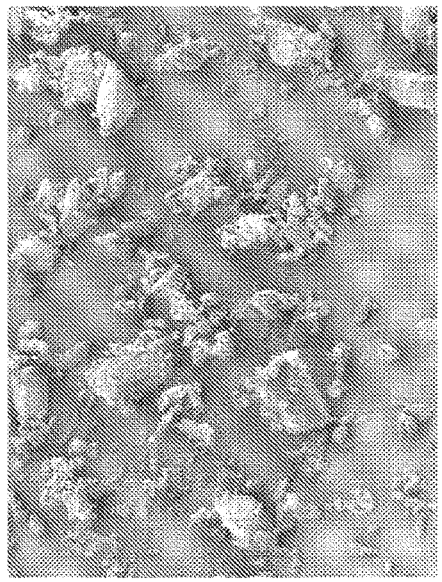
Figure 37C:
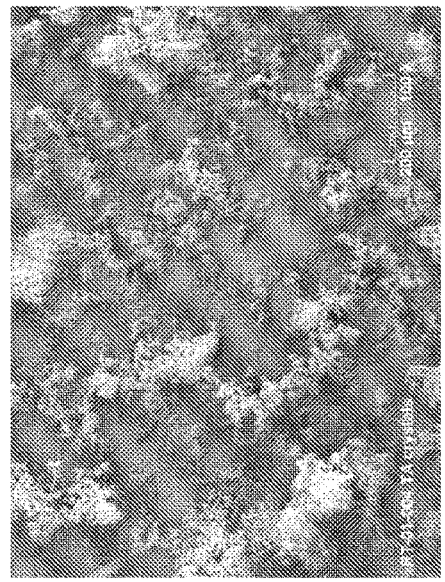
Figure 37E:
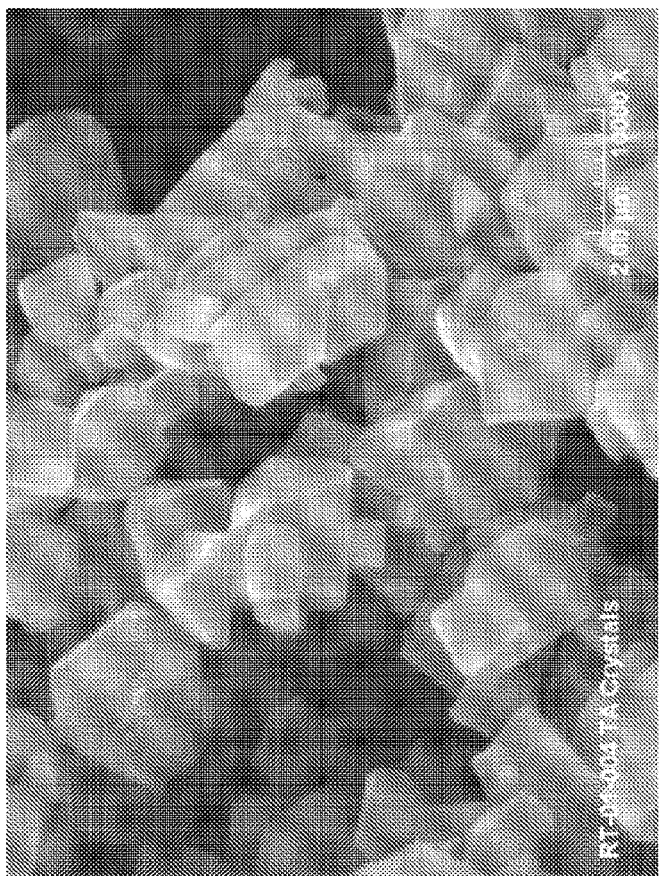

Morphology of the TA nanocrystals made in Example 9 was investigated with Scanning Electron Microscopy (SEM) (Amray 1000A upgraded with a PGT (PRINCETON GAMMA TECH®) Spirit EDS/Imaging system. Sample was argon sputter coated (HUMMER V® from ANATECH®) with gold (~200 Å). Sample was mounted on double side tape. FIGS. 37A and 37B are SEM images of the TA stock material, at two different magnifications. FIGS. 37C-E are SEM images of TA nanocrystals. As seen in the SEM images, the morphology of the nanocrystals prepared by the process of the invention is markedly different than that of the stock material from the manufacturer.

TA Nanocrystals Prepared by the Process of the Invention Maintain Their Purity and Integrity The measurement of triamcinolone acetonide was adapted from Matysová et al. (2003), "Determination of methylparaben, propylparaben, triamcinolone", and the only modification made was the increased run time to compensate for our longer column used for the assay. Samples were run at low concentrations in an effort to amplify any contaminant peaks vs. TA peaks (an effect seen in fluticasone analysis).

The resulting chromatograms were very clean, with a TA peak elution seen at 28.9 minutes. The conditions were:
HPLC System: AGILENT® 1100 with CHEMSTATION® Software
Column: PHENOMENEX LUNA®; C18, 5 µm pore size, 100 Å, Dimensions: 250×4.60 mm
Mobile Phase: 40/60 v/v Acetonitrile and HPLC grade water.
Injection Volume: 20 µL
Analysis Time: 30 Minutes
Detection Wavelength: 240 nm Comparison of the HPLC traces of the TA nanocrystals with those of the TA stock material demonstrated that the nanocrystals produced by the process of the invention did not degrade as a result of the process of the invention.

Crystal Structure of Triamcinolone Acetonide Produced by the Process of the Invention vs. the Triamcinolone Acetonide Stock Material The triamcinolone acetonide crystals (i.e., Form B) prepared by the method of this invention have a different crystalline habit from the stock material, as evidenced by the different XRPD patterns in FIG. 39. In other words, the triamcinolone molecules within the unit cell are packed differently from those of the stock material. Similar to fluticasone nanocrystals (Form A), this new morphic form of triamcinolone can have different physiological properties as compared to the triamcinolone stock material.

Example 11

Nanocrystal Manufacturing Process-Modified Flow and Purification Process

Experiments were designed to generate process conditions that would: (a) reproducibly generate nanocrystals of cumulants mean size as approximately 500 nm (±200 nm), (b) reproducibly generate stable crystals, with stability defined by chemical and physical stability and (c) reproducibly maintain crystal size after purification at high centrifugal forces.

Several modifications to the flow process described in Example 7 were made. In particular, a mixing step between crystal formation and annealing was added. Other steps that were added include: (a) dilution with a "washing solution" between the annealing and the centrifugation steps, (b) re-dispersion of the pellet in the washing solution for further purification, (c) collection of a pellet and its re-dispersion into the final formulation composition. Using this modified flow process, producing nanosuspension at 0.09% drug at 3500 g/min, commercially relevant volumes of nanosuspension can be manufactured. The flow reactor was equipped with sanitary fittings, designed to be autoclaved. The steps defined in FIG. 38 led to final production of highly pure drug crystals of cumulants mean size of 500 nm (±200 nm).

Role of the Probe Design

Scale-up experiments with the purpose of enhancing efficiency were performed with both a standard 1" sonicating probe with a single active tip at the bottom of the probe and a "bump-stick" probe with multiple sonicating tips on the wand.

Standard Probe Experiments:

Various combinations of fluticasone propionate percentage, flow rates, temperatures, and amplitude of sonication were tested to determine their effects on mean size of the crystals. Fluticasone propionate percentage ranged from 0.224% to 0.229%. The flow rate of phase I ranged from 0 to 825 mL/min. The flow rate of phase II ranged from 10 to 900 mL/min. The flow rate of phase III ranged from 25 to 1400 mL/min. The phase II/phase I flow rate ratio ranged was 1. The temperatures were 0-22° C. for phase I, 0-22° C. for phase II, 10-40° C. for phase III. The average phase III temperature ranged from 12.5 to 40° C. The amplitude of sonication ranged from 25% to 75% output. The resulting mean size (e.g., d50, or mass median diameter) of the crystals ranged from 0.413 µm to 7 µm.

The highest flow rate of phase I and phase II that yielded particles of size d50~500 nm, was 250 ml/min at all output energies (25% output, 75% output). Higher flow rates (at Phase II/Phase I ratio=1) at 700 ml/min for Phase I and Phase II led to large particle sizes>7 µm.

Experiments with the bump stick probe demonstrated that higher flow rates of Phase I and Phase II could be achieved, thus enhancing the efficiency of the flow process many-fold. Particle sizes of d50≤500 nm could be achieved when used in synergy with other parametric variables such as choice of buffer, pH of phase II, or sonication output energy. All other experiments described in this Example were performed with the bump stick probe.

Role of Buffer and pH in Phase II

The pH of the phase II affected the particle size. The pH of phase II was ~8, resulting in a pH of ~7 post-mixing of phase I and phase II. Ascorbic and Citrate buffers at pH 4 and pH 5 were investigated as buffers for phase II. Particle size was measured using a MALVERN® S90®. The MALVERN® S90® measures particle size by dynamic light scattering (DLS). For needle-shaped crystals as the proprietary fluticasone propionate crystals produced by this process, the most relevant value for particle size measured by DLS is the peak mean, or the cumulants mean. Thus, all particle size values are reported as the cumulants mean. An example is shown in Table 17.

TABLE 17

Particle Size (cumulants peak mean) as a Function of Ascorbic Acid Buffer, pH 5

| Time | Particle Size $(nm)_1$ | Particle Size $(nm)_2$ | Particle Size $(nm)_3$ |
|---|---|---|---|
| | 25° C. Annealing | | |
| t0 (post titration) | 748.90 | 768.10 | 678.60 |
| t1 (+98 hours) | 596 | 510.8 | 509.2 |
| | 40° C. Annealing | | |
| t0 (post titration) | 748.90 | 768.10 | 678.60 |
| t1 (+98 hours) | 596.9 | 441.8 | 766.3 |

Both 25° C. and 40° C. are suitable as annealing temperatures. Additional temperatures may also be suitable for annealing. Ascorbate buffer, pH 5 used in phase II generated particles between 500-800 nm (d50). Citrate buffer at pH 4 and pH 5 were investigated as the buffering agent in phase II in multiple flow reactor batches. Representative examples are shown in Tables 18-19.

TABLE 18

Particle Size (cumulants peak mean) as a Function of Citrate Buffer, pH 4

| Time | Particle Size $(nm)_1$ | Particle Size $(nm)_2$ | Particle Size $(nm)_3$ |
|---|---|---|---|
| t1 pre-mixing | 476.1 | 510.2 | 610.6 |
| t2 after 30 m mix | 588.5 | 617.1 | 465.7 |

TABLE 19

Particle Size $(d_{50})$ as a Function of Citrate Buffer, pH 5

| Time | Particle Size $(nm)_1$ | Particle Size $(nm)_2$ | Particle Size $(nm)_3$ |
|---|---|---|---|
| t0 pre-mixing | 630.4 | 625.6 | 654.5 |
| t1 after 30 m mix | 624.7 | 516.4 | 645.5 |

In general, both citrate and ascorbate buffers were suitable, and statistically, no differences were noted. Citrate buffer was selected as the buffer of choice due to its presence in multiple pharmaceutical formulations. pH 5 was selected as the pH of choice of phase II, due to slight increases in impurities shown in nanosuspensions prepared at pH 4 and annealed at 25° C. Nanosuspensions prepared in phase II at pH 5, citrate buffer showed no increase in impurities during annealing.

Role of Sonication Output Energy

The sonication output energy was investigated as a variable in the generation of nanocrystals of particle size with a cumulants mean value at 500 nm (±200 nm). To obtain detailed statistically meaningful data on particle size, a HORIBA® LA-950 Laser Diffraction Particle Sizer was utilized, which provides the statistical mean, median and mode of each batch analyzed.

Table 21 is an example of a batch prepared at 40% output energy, 1:4 Phase I: Phase II ratio. The composition of phase II was 0.4% 15 centipoise methyl cellulose (MC), 0.005% benzalkonium chloride, 0.1% PEG40 Stearate in citrate buffer, pH 5 and distilled water. The data shown in Tables 22-24 are representative of batches produced at 50%, 60% and 70% output energies, with all other parameters identical, or as similar as possible. Thus, the phase I, phase II and phase III compositions were the same, temperatures of each of the phases in each batch were similar, as well as the temperatures of annealing. The annealing temperature of the incubator ranged from 25-28° C., with a 65%-75% relative humidity. The flow rate of Phase III for each of the batches was 3250 g/min (±200 g/min). After production of the nanocrystals, each batch was mixed with a SCILOGIX® mixer at 250 RPM at room temperature. Batch sizes were approximately 3500 grams. Phase III composition of each batch is tabulated in Table 20.

TABLE 20

Phase III Composition with a 1:4 Phase I:Phase II Ratio

| Component | grams | % |
|---|---|---|
| Fluticasone Propionate | 3.15 | 0.09 |
| TWEEN 80 ® (polysorbate 80) | 53.13 | 1.52 |
| Polypropylene Glycol 400 | 481.67 | 13.762 |

TABLE 20-continued

Phase III Composition with a 1:4 Phase I:Phase II Ratio

| Component | grams | % |
|---|---|---|
| Polyethylene Glycol 400 | 162.05 | 4.63 |
| Methyl Cellulose 15 cP | 11.2 | 0.32 |
| PEG40 Stearate | 2.8 | 0.08 |
| Benzalkonium Chloride | 0.14 | 0.004 |
| Citrate Buffer (0.1M), pH 5 | 44.8 | 1.28 |
| Water | 2714.06 | 78.32 |

Particle size data was provided in terms of mean, median and mode. By definition, the mode particle size signifies the highest number of particles with that size, the median particle size signifies the number of particles that are in the "middle" of the distribution, and the mean particle size is the average of all sizes for the entire distribution. For a perfect monomodal Gaussian distribution, the mean, median and mode are all similar. In distributions that are skewed, these values differ widely. The mean, median and mode values are all within a 250 nm range, after at least 24 hours of annealing.

TABLE 21

Representative batch prepared with 40% output energy
1:4 Batch, pH 5, 40% amplitude

| | | Flow rate: | | Amp: 40% | | |
|---|---|---|---|---|---|---|
| Time | Mean (um) | Median (um) | Mode (um) | d90 (um) | d50 (um) | |
| t0 | 0.67215 | 0.44926 | 0.3638 | 1.4063 | 0.4493 | PEG- |
| (+) 30 min mix | 0.6827 | 0.44473 | 0.3632 | 1.4527 | 0.4447 | Stearate |
| (+)24 | 0.7038 | 0.44397 | 0.3629 | 1.5136 | 0.444 | 0.1% |

TABLE 22

Representative batch prepared with 50% output energy
1:4 batch 0.005% BKC, 0.1% PEG-Stearate, pH 5 phase II.
Phase III temp = 11.5; rate = 3495 g batch size; 50% AMP

| | | Flow rate: 3608 g/min | | Amp: 50% | | |
|---|---|---|---|---|---|---|
| Time (hrs) | Mean (um) | Median (um) | Mode (um) | d90 (um) | d50 (um) | |
| 0 | 0.59984 | 0.43397 | 0.3647 | 1.179 | 0.434 | PEG- |
| (+) 30 min mix | 0.56879 | 0.40337 | 0.3619 | 1.1672 | 0.4034 | Stearate |
| 96 | 0.61444 | 0.41099 | 0.3618 | 1.2931 | 0.411 | 0.1% |
| 112 | 0.64135 | 0.4125 | 0.3616 | 1.3758 | 0.4125 | |

TABLE 23

Representative batch prepared with 60% output energy
1:4 batch 0.005% BKC, 0.1% PEG-Stearate, pH 5.04 phase II.
13° C. Phase III - 3498 g batch. 60% Amp.

| | | Flow rate: | | Amp: 60% | | |
|---|---|---|---|---|---|---|
| Time | Mean (um) | Median (um) | Mode (um) | d90 (um) | d50 (um) | |
| t0 | 0.72887 | 0.54961 | 0.4781 | 1.3807 | 0.5496 | PEG- |
| (+) 30 min mix | 0.71239 | 0.51732 | 0.4172 | 1.429 | 0.5173 | Stearate |
| (+)24 | 0.69401 | 0.52177 | 0.418 | 1.3659 | 0.5218 | 0.1% |
| (+)48 | 0.76579 | 0.52094 | 0.4173 | 1.5413 | 0.5209 | |
| (+)144 | 0.6936 | 0.51772 | 0.4181 | 1.348 | 0.5177 | |
| (+)144 | 0.75277 | 0.52247 | 0.4176 | 1.5225 | 0.5225 | |

TABLE 24

Representative batch prepared with 70% output energy
1:4 batch 0.005% BKC, 0.1% PEG-Stearate, pH 5 phase II.
Phase III temp = 13; rate = 3470; g batch size; 70% Amp

| | | Flow rate: 3495 g/min | | Amp: 70% | | |
|---|---|---|---|---|---|---|
| Time | Mean (um) | Median (um) | Mode (um) | d90 (um) | d50 (um) | |
| t0 | 2.93615 | 0.43001 | 0.3631 | 2.9617 | 0.43 | PEG- |
| (+) 30 min mix | 0.65677 | 0.4636 | 0.38867 | 1.5569 | 0.3887 | Stearate |
| (+)96 | 0.52345 | 0.40234 | 0.363 | 1.0063 | 0.4023 | 0.1% |
| (+)112 | 0.5985 | 0.3935 | 0.3611 | 1.2603 | 0.3936 | |

TABLE 25

Representative batch prepared with 80% output energy
1:4 batch, pH 5, 80% amplitude

| | | Flow rate: | | Amp: 80% | | |
|---|---|---|---|---|---|---|
| Time | Mean (um) | Median (um) | Mode (um) | d90 (um) | d50 (um) | |
| t0 | 0.88407 | 0.34681 | 0.1836 | 2.2933 | 0.3468 | PEG- |
| (+) 30 min mix | 1.19832 | 0.56541 | 0.3645 | 2.8992 | 0.5654 | Stearate |
| (+)24 | 1.61358 | 0.57793 | 0.365 | 3.4731 | 0.5779 | 0.1% |

Thus, initial particle size (T=0 values) generated by crystallization in the presence of sonication is almost directly correlated to output energy, i.e. the higher the output energy, the smaller the statistical mode (the most frequently occurring size).

By annealing, the particles can settle into a lower energy state. The particles have high surface energy with increase in output energy, causing the particles to agglomerate. This is evidenced in Table 24, which describes particle size dynamics of a batch generated with 70% output energy. At T=0, the batch had a mean particle size of 2.93 microns and a mode value ("most frequent" value) of 0.3631 microns, indicating that even if most of the particles were <500 nm, there were some large particles in the distribution that skewed the mean. At T=96 hours of annealing at 25° C., the mean, median and mode were within 250 nm of each other, proving that the larger particles skewing the mean were agglomerates. Annealing the batch lowered the surface energy into an equilibrated ground state, thus de-aggregating the particles.

Particle Size Decreases with Annealing

Annealing has been shown to be a critical part of the batch process, as shown in previous data. Annealing of crystals generated by the continuous flow process has also proved to be a significant part of the process, as discussed in the previous section.

It was also demonstrated above that the kinetics of annealing is important. In various experiments, it did seem that particle sizes of batches annealed at 25° C., 40° C. and 60° C. did not significantly differ from each other in terms of particle sizes. However, annealing has another purpose. The crystallization can be "completed" by annealing, thus "hardening" the crystals. From this perspective, the higher the temperature of annealing without degradation, the more crystalline the particles will be.

Table 26 shows a batch prepared with the ascorbate-buffered phase II, pH 5, annealed at two different temperatures. These batches were prepared with ascorbic acid buffer, pH 5, phase I: phase II: 1:3, 60% output energy. The particle size was measured by the MALVERN® S90®. The same batch of particles annealed at two different temperatures show a different mean peak size, as measured by the instrument. However, both sets show decrease in particle size with annealing.

TABLE 26

Representative Batch Annealed at 25° C.

| | 25° C. Annealing | | |
|---|---|---|---|
| Time | Particle Size $d_{50}$ (nm)$_1$ | Particle Size $d_{50}$ (nm)$_2$ | Particle Size $d_{50}$ (nm)$_3$ |
| t0 (post titration) | 748.90 | 768.10 | 678.60 |
| t1 (+98 hours) | 596 | 510.8 | 509.2 |

TABLE 27

Representative Batch Annealed at 40° C.

| | 40° C. Annealing | | |
|---|---|---|---|
| Time | Particle Size (nm)$_1$ | Particle Size (nm)$_2$ | Particle Size (nm)$_3$ |
| t0 (post titration) | 748.90 | 768.10 | 678.60 |
| t1 (+98 hours) | 296.9 | 441.8 | 766.3 |

Role of Mixing Head Design

The design of the mixing head is important for mixing the nanosuspension right after crystallization in the flow reactor. The mixing heads were tested in multiple experiments. SILVERSON® mixing heads were evaluated. The medium and the low shear mixing heads (co-axial and paddle) provided the best particle sizes. The paddle mixer was selected as the mixing head of choice for all batches.

Role of Benzalkonium Chloride

Benzalkonium chloride is needed to generate particles with a statistical mode value of ~500 nm.

Table 28 is a representative batch that was prepared with no benzalkonium chloride in phase II. The mean, median and mode value variance was within 250 nm. The mode value was 1.07 microns. Since particle sizes of ~1 micron and greater were obtained for all batches produced with no benzalkonium chloride, it is deemed necessary for benzalkonium chloride to be present in phase II, in order to generate particles of sizes with a statistical mode of ~500 nm. Batches described in Tables 28, 29, 30A, and 30B were analyzed with the HORIBA® LA-950® Laser Diffraction Particle Size Analyzer.

TABLE 28

1:4 batch w/ no BAK; pH 5.21 phase II - 14° C.
phase III - 4346.87 g/min, 3332.6 g batch, 60% Amp.

| | Phase III Flow rate: 4346.87 g/min | | | | |
|---|---|---|---|---|---|
| Time | Mean (um) | Median (um) | Mode (um) | d90 (um) | d50 (um) |
| | 1.16041 | 0.85161 | 1.0782 | 2.3984 | 0.8516 |
| (+) 30 min mix | 1.22985 | 0.9466 | 1.2295 | 2.4875 | 0.9466 |
| (+) 60 hrs | 1.24168 | 0.93764 | 1.2274 | 2.5123 | 0.9376 |

Table 29 is a representative batch prepared with 20 ppm (0.002%) benzalkonium chloride in phase II. Phase II was also buffered with citrate, pH 5. The flow rate of phase III was 3250±200 nm. The batch was a 1:4 ratio batch. Thus, the BAK concentration in phase III was 16 ppm. The batch meets the T=0 particle size specification of statistical mode<500 nm (±200 nm).

TABLE 29

1:5 batch with 0.002% BKC, pH 5.0 Phase II;
11° C. Phase III; 3369.2 g batch; 60% Amp

| | Flow rate: 3369.5 g/min | | | Amp: 60% | |
|---|---|---|---|---|---|
| Time | Mean (um) | Median (um) | Mode (um) | d90 (um) | d50 (um) |
| 0 hrs | 0.54942 | 0.45566 | 0.416 | 0.9908 | 0.4557 |
| 0 hrs (+) 30 min mix | 0.41045 | 0.26352 | 0.2104 | 0.9282 | 0.2635 |
| (+) 15 hrs | 0.58982 | 0.46256 | 0.3658 | 1.1239 | 0.4626 |
| (+) 48 hrs | 0.7226 | 0.45139 | 0.3636 | 1.5348 | 0.4514 |
| (+) 72 hrs | 0.63121 | 0.43998 | 0.3628 | 1.2978 | 0.44 |

Table 30A and 30B are representative batches prepared with 50 ppm (0.005%) benzalkonium chloride in phase II. Phase II was also buffered with citrate, pH 5. The flow rate of phase III was 3250±200 nm. The batch was a 1:4 ratio batch. Thus, the BAK concentration in phase III was 40 ppm. The batches meet the T=0 particle size specification of statistical mode<500 nm (±200 nm). These batches also contained PEG40-stearate as a stabilizing molecule.

TABLE 30A

1:4 batch 0.005% BKC, 0.1% PEG40-Stearate, pH 5.04
phase II. 13° C. Phase III - 3498 g/min, 60% Amp.

| | Flow rate: 3250 | | | Amp: 60% | |
|---|---|---|---|---|---|
| Time | Mean (um) | Median (um) | Mode (um) | d90 (um) | d50 (um) |
| t0 | 0.72887 | 0.54961 | 0.4781 | 1.3807 | 0.5496 PEG- |
| (+) 30 min mix | 0.71239 | 0.51732 | 0.4172 | 1.429 | 0.5173 Stearate |
| (+)24 | 0.69401 | 0.52177 | 0.418 | 1.3659 | 0.5218 0.1% |
| (+)48 | 0.76579 | 0.52094 | 0.4173 | 1.5413 | 0.5209 |
| (+)144 | 0.6936 | 0.51772 | 0.4181 | 1.348 | 0.5177 |
| (+)144 | 0.65277 | 0.52247 | 0.4176 | 1.5225 | 0.5225 |

TABLE 30B

1:4 batch 0.005% BKC, 0.1% PEG-Stearate, pH 5 phase II. Phase
III temp = 11.5; rate = 3495 g/min; 50% AMP

| | Flow rate: 3608 g/min | | | Amp: 50% | |
|---|---|---|---|---|---|
| Time (hrs) | Mean (um) | Median (um) | Mode (um) | d90 (um) | d50 (um) |
| 0 | 0.59984 | 0.43397 | 0.3647 | 1.179 | 0.434 PEG- |
| (+) 30 min mix | 0.56879 | 0.40337 | 0.3619 | 1.1672 | 0.4034 Stearate |
| 96 | 0.61444 | 0.41099 | 0.3618 | 1.2931 | 0.411 0.1% |
| 112 | 0.64135 | 0.4125 | 0.3616 | 1.3758 | 0.4125 |

Role of PEG 40-Stearate 0.01% PEG40-stearate was used as the sole stabilizer in a citrate-buffered phase II, 1:3 Phase I/phase II ratio, 60% AMP. This data was analyzed by the MALVERN® S90®. The particle size shown is the cumulants mean. As shown in Table 31, the particle size specification of meeting the cumulants mean of 500 nm was met. The level of PEG40-stearate will vary depending on if a benzalkonium chloride-free batch is prepared.

TABLE 31

0.01% PEG-Stearate phase II, Mixed w/ paddle
mixer @ 250 rpm for 30 m. Final pH = 5.47

| | 25° C. Annealing | | |
|---|---|---|---|
| Time | Particle Size (nm)$_1$ | Particle Size (nm)$_2$ | Particle Size (nm)$_3$ |
| t0 | 556.1 | 665.1 | 582.2 |
| t1 + 68 hours | 554.7 | 863.7 | 426.6 |

Fluticasone Propionate Nanocrystals Purified by Continuous Flow Centrifugation

Continuous Flow Centrifugation was demonstrated as the preferred means of purifying the crystals. Through purification, the continuous phase of phase III is centrifuged out. The pellet is re-dispersed as a concentrate in the washing solution and the dispersion re-centrifuged. Continuous centrifugation was performed by a SORVALL® Contifuge or a BECKMAN COULTER® JI-30 with a JCF-Z® Rotor can be used.

In general, after the nanosuspension has been annealed overnight, the batch is then diluted 1:1 with 0.1% PEG40-Stearate, 0.1% TWEEN 80° (polysorbate 80) and 50 ppm Benzalkonium Chloride. Dilution of the nanosuspension lowers the viscosity of phase III to enable ease of centrifugation.

The BECKMAN® centrifuge is cooled to 4° C., and the suspension centrifuged at 1.6 L/min at 39,000 G. The supernatant appeared clear and devoid of particles. The particle size distributions are shown in Table 32. This batch had been prepared with no benzalkonium chloride. Thus, the particle size is larger than the usual 500 nm statistical mode. Surprisingly, after purification, the mode shifts to <500 nm. This shows that the centrifugation breaks down agglomerated particles. This is a way to eliminate large particles.

TABLE 32

1:4 batch w/ no BKC; pH 5.21 phase II - 14° C.
phase III - 4346.87 g/min, 3332.6 g batch. 60% Amp.

| | Flow rate: 4346.87 g/min | | | | |
|---|---|---|---|---|---|
| Time | Mean (um) | Median (um) | Mode (um) | d90 (um) | d50 (um) |
| | 1.16041 | 0.85161 | 1.0782 | 2.3984 | 0.8516 |
| (+) 30 min mix | 1.22985 | 0.9466 | 1.2295 | 2.4875 | 0.9466 |
| (+) 60 hrs | 1.24168 | 0.93764 | 1.2274 | 2.5123 | 0.9376 |
| purified after 60 hrs | 1.1979 | 0.73998 | 0.4747 | 2.6483 | 0.74 |

Flow process variables that play a role in particle size are temperatures of phase I and phase II, pH of phase II, composition of phase II, output energy, probe design, flow rate, ratio of phase II to phase I, annealing temperature, mixing conditions after particle production and composition of washing solution prior to purification. These results demonstrate for the first time that the manufacturing flow process produces commercial volumes of fluticasone propionate nanosuspension crystals and that the crystals can be purified using high flow continuous centrifugation.

Example 12

Formulations of FP Nanocrystals and Evaluation

Formulations containing fluticasone propionate nanocrystals with different FP contents (e.g., 0.25%±0.0375% (0.21-0.29%), 0.1%±0.015% (0.085-0.115%), and 0.05%±0.0075% (0.043-0.058%)) were prepared and evaluated. The following parameters of each formulation were evaluated: spreading of formulation on the skin (minimum contact angle preferred), chemical compatibility (of other ingredient) with FP, dose uniformity and redispersibility, stability of particle (e.g., unchanged size of particles preferred), and droplet size (function of viscosity and intermolecular surface tension, maximizing droplet size preferred).

Tables 33 and 34 below list the components of two different pharmaceutical formulations (each containing 0.25% FP) that were prepared for use in treating, e.g., blepharitis.

TABLE 33

| Formulation I | | |
|---|---|---|
| Ingredients | Composition (%) | Intended Function |
| Fluticasone Propionate | 0.250 | Active |
| Benzalkonium chloride | 0.005 | Preservative |
| Polysorbate 80 | 0.200 | Coating Dispersant |
| Glycerin | 1.000 | Tissue Wetting Agent |
| PEG stearate | 0.200 | Coating Dispersant |
| Methyl cellulose 4000 cP | 0.500 | Polymeric stabilizer |
| Sodium Chloride | 0.500 | Tonicity Adjustment |
| Dibasic sodium phosphate | 0.022 | Buffering Agent |
| Monobasic sodium phosphate | 0.040 | Buffering Agent |
| Water | 97.340 | |

TABLE 34

| Formulation II | | |
|---|---|---|
| Ingredients | Composition (%) | Intended Function |
| Fluticasone Propionate | 0.250 | Active |
| Benzalkonium chloride | 0.005 | Preservative |
| Glycerin | 1.000 | Tissue Wetting Agent |
| Tyloxapol | 0.200 | Coating Dispersant |
| Methyl cellulose 4000 cP | 0.500 | Polymeric stabilizer |
| Sodium Chloride | 0.500 | Tonicity Adjustment |
| Dibasic sodium phosphate | 0.022 | Buffering Agent |
| Monobasic sodium phosphate | 0.040 | Buffering Agent |
| Water | 97.483 | |

Formulation I, ingredients of which are listed in Table 33 above, was evaluated and had the following properties: Viscosity=45±4.1 cP; pH=6.8-7.2; osmolality=290-305 mOsm/kg; particle size: statistical mode: 400 nm, median: 514 nm, mean: 700 nm, d50: 400 nm, d90: 1.4 μm; and droplet size=40±2 μL. Further, Formulation I was redispersible upon shaking, exhibited uniform dose for at least one hour after shaking; and the particle size was stable for at least 21 days at a temperature between 25° C. and 40° C.

Formulation II, ingredients of which are listed in Table 34 above, was evaluated and had the following properties: Viscosity=46±3.2 cP; pH=6.8-7.2; osmolality=290-305 mOsm/kg; particle size: statistical mode: 410 nm, median: 520 nm, mean: 700 nm, d50: 520 nm, d90: 1.4 μm; and droplet size=40±2.3 μL. Further, Formulation II was redispersible upon shaking, exhibited uniform dose for at least one hour after shaking; and the particle size was stable for at least 18 days at a temperature between 25° C. and 40° C.

Average droplet sizes of other formulations having different FP contents (i.e., about 0.25%, 0.1%, 0.05%, and 0%) were tested are summarized in Table 35 below. The test was conducted using a 7 mL drop-tip eye-dropper bottle with a 5 mL fill and with drop-tip pointed vertically down. The amount of FP per droplet was determined by HPLC.

TABLE 35

| 0.25% FP | | 0.1% FP | | 0.05% FP | | 0% FP | |
|---|---|---|---|---|---|---|---|
| ave. droplet size (μL) | FP per drop (μg) | ave. droplet size (μL) | FP per drop (μg) | ave. droplet size (μL) | FP per drop (μg) | ave. droplet size (μL) | FP per drop (μg) |
| 41.17 | 102.925 ± 3.5766 | 39.54 | 39.54 ± 3.1263 | 40.65 | 20.325 ± 1.950 | 40.27 | 0 |

As shown in Table 35 above, the droplet size was consistent across all of the formulations tested.

To test drug delivery efficiency of different applicators, the 0.25 FP % Formulation I mentioned above was loaded to various applicators such as swabs and brushes (e.g. FOAMEC-1® swab, polyurethane swab, polyester swab, 25-3318-U swab, 25-3318-H swab, 25-3317-U swab, 25-803 2PD swab, 25-806 1-PAR swab, cotton swab, and LATISSE® (bimatoprost ophthalmic solution) brush), and then each FP-loaded applicator was swiped against a polypropylene membrane to determine how much FP was transferred onto the membrane.

More specifically, for each applicator, two drops of Formulation I were loaded on the applicator before swiping the applicator on a polypropylene membrane twice. The FP transferred onto membrane was then extracted with the mobile phase used for HPLC analysis to determine the amount of FP transferred onto the membrane. For each kind of applicator, the same measurement was repeated 3-8 times. It was observed that LATISSE® (bimatoprost ophthalmic solution) brushes demonstrated better drug delivery (i.e., about 56% FP transferred on average) to polypropylene membrane than the other applicators. Ranked the second was 25-3317-U swab (i.e., about 34% FP transferred on average). The average percentage of FP delivered to the polypropylene membranes by each of the other applicators tested is listed in Table 36 below.

TABLE 36

| Foamec-1 | Polyurethane | Polyester | 25-3318-U | 25-3318-H | 25-8032PD | 25-8061-PAR | Cotton swab |
|---|---|---|---|---|---|---|---|
| 6.9-22.17 | 1.06 | 0.41 | 13.92 | 18.71 | 14.39 | 1.03 | 0.94 |

It was also observed that polyester swabs and cotton swabs absorbed the formulation drops quickly; and when swiped on membrane, the FP was barely transferred. On the other hand, polyurethane swabs "beaded" the drops—drops fell off. It took two seconds for LATISSE® (bimatoprost ophthalmic solution) brush to absorb $1^{st}$ drop and 1.3 seconds for 25-3317-U swab to absorb $1^{st}$ drop. In terms of ease of use, LATISSE® (bimatoprost ophthalmic solution) brushes are easier to use compared to the other applicators tested.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

We claim:

1. Nanocrystals of fluticasone propionate polymorph 1 having a crystalline habit (Form A) characterized in that the [001] crystallographic axis is substantially normal to the surfaces that define the thickness of the nanocrystals, wherein the nanocrystals have a size distribution of about 100-1000 nm and a X-ray powder diffraction pattern with characteristic peaks at about 7.8, 15.7, 20.8, 23.7, 24.5, 32.5 degrees 2θ and additional peaks at about 9.9, 13.0, 14.6, 16.0, 16.9, 18.1, and 34.3 degrees 2θ.

2. Nanocrystals of fluticasone propionate of claim 1 having a thickness of about 5 nm to 500 nm.

3. Nanocrystals of fluticasone propionate of claim 1 having a purity of greater than 99% by weight.

4. Nanocrystals of fluticasone propionate of claim 1 having a size distribution of about 400-800 nm.

5. Nanocrystals of fluticasone propionate of claim 1 having a size distribution of about 400-600 nm.

6. Nanocrystals of fluticasone propionate according to claim 5 having a tap density of 0.5786 g/$cm^3$.

7. Pharmaceutical composition comprising nanocrystals of fluticasone propionate according to claim 1 and a pharmaceutical acceptable carrier.

8. Pharmaceutical composition according to claim 7 in the form of topical formulation comprising a suspension of nanocrystals of fluticasone propionate having a concentration of between 0.0001% to 10%.

9. Pharmaceutical composition according to claim 8 wherein the concentration fluticasone propionate nanocrystals is 0.001% to 5%.

10. Pharmaceutical composition according to claim 9 further containing about 0.002-0.01% of benzalkonium chloride, one or more coating dispersants, one or more tissue wetting agents, one or more polymeric stabilizers, one or more buffering agents, and one or more tonicity adjusting agents.

11. A topical formulation comprising a suspension of nanocrystals of fluticasone propionate according to claim 1 wherein the concentration of fluticasone propionate nanocrystals is 0.01%-1%; benzalkonium chloride 0.002-0.01%; polysorbate 80, 0.01-1%; PEG40 stearate 0.01-1%; glycerin 0.1-10%; methyl cellulose 4000 cP, 0.05-5%; sodium chloride 0.05-5%; dibasic sodium phosphate and monobasic sodium phosphate; water and the formulation has a pH of about 6.8-7.2.

12. A method for the amelioration or alleviation of sign or symptom of blepharitis comprising administering to a subject in need a therapeutically effective amount of the topical formulation of claim 9.

13. The method of claim 12 wherein the formulation is loaded onto an applicator and then delivered to the subject in need thereof by swiping the applicator against the lower eyelid and then the upper eyelid.

14. A method for the amelioration or alleviation of sign or symptom of blepharitis comprising administering to a subject in need a therapeutically effective amount of the topical formulation of claim 10.

15. The method of claim 14 wherein the formulation is loaded onto an applicator and then delivered to the subject in need thereof by swiping the applicator against the lower eyelid and then the upper eyelid.

16. A method for the amelioration or alleviation of sign or symptom of meibonian gland dysfunction comprising administering to a subject in need a therapeutically effective amount of the pharmaceutical composition of claim 8.

17. A method of ameliorating post-operative surgery ocular inflammation and post-operative surgery ocular pain comprising administering to a subject in need thereof an effective amount of the pharmaceutical composition of claim 8.

18. A method of manufacturing the nanocrystals of fluticasone propionate according to claim 1, comprising:
1) providing a sterile phase I solution comprising: fluticasone propionate at a concentration of 0.4% to 1.0%; polyethylene glycol (PEG) 400 at a concentration of about 20 to 35% (w/v); polypropylene glycol (PPG) 400 at a concentration of about 65% to 75%; and polysorbate 80 (Tween 80) at a concentration of 7.0% to 15% (w/v);
2) providing a sterile phase II solution comprising: water; methylcellulose having a viscosity of about 4 to 50 cP at a concentration of about 0.1% to 0.5%; benzalkonium chloride at a concentration of 0.005% to 0.15% (w/v); and the pH of phase II solution is 5.5;
3) mixing the phase I solution and the phase II solution to obtain a phase III mixture, wherein:
the phase I solution is mixed with the phase II solution at a flow rate of 0.5 to 1.4 ml/mim and the Phase II solution is stationary;
the volume ratio of the phase I solution and phase II solution is 1:1 to 1:3;
sonication is applied when mixing the sterile phase I and the sterile phase II and the mixing is performed at a the first temperature not greater than 8° C.;
4) annealing the phase III mixture at a temperature of between 10° C. and 40° C. for a period of time such as to produce a phase III suspension comprising a plurality of nanocrystals of fluticasone propionate; and
5) optionally purification of the nanocrystals by tangential flow filtration or by continuous centrifugation.

19. The method of claim 18, wherein:
the composition of the phase I is: fluticasone propionate 0.45%, polyethylene glycol (PEG) 400 23,18% (w/w), polypropylene glycol (PPG) 400 68.70, and polysorbate 80 (Tween 80) 7.67% (w/w);
the composition of the phase II is: benzalkonium chloride 0.020% w/w, methyl cellulose 15cP 0.40% w/w, water (Qs to 100%), and the pH is 5.5;
the phase I solution is mixed under sonification at a flow rate of 1.43 ml/min with the phase II;
the volume ratio of phase I to phase II is 1:1;
the temperature of each phase I and phase II is 0-1° C.;
the phase III dispersion is annealed at 25° C. for a period of at least 8 hours;
the crystals produced are purified by tangential flow filtration or by continuous centrifugation.

20. The method according to claim 18, wherein sonication is applied with an output power of about 10-75 watt.

* * * * *